US009181326B2

(12) United States Patent
Rush, II et al.

(10) Patent No.: US 9,181,326 B2
(45) Date of Patent: Nov. 10, 2015

(54) ANALYSIS OF UBIQUITINATED POLYPEPTIDES

(71) Applicant: Cell Signaling Technology, Inc., Danvers, MA (US)

(72) Inventors: John Edward Rush, II, Beverly, MA (US); Jing Li, Brighton, MA (US); Ailan Guo, Lexington, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

(21) Appl. No.: 13/856,933

(22) Filed: Apr. 4, 2013

(65) Prior Publication Data
US 2013/0245237 A1 Sep. 19, 2013

Related U.S. Application Data

(62) Division of application No. 12/967,284, filed on Dec. 14, 2010, now abandoned.

(60) Provisional application No. 61/286,486, filed on Dec. 15, 2009.

(51) Int. Cl.
*C07K 16/00* (2006.01)
*G01N 33/68* (2006.01)

(52) U.S. Cl.
CPC ............ *C07K 16/00* (2013.01); *G01N 33/6842* (2013.01); *G01N 2440/36* (2013.01)

(58) Field of Classification Search
None
See application file for complete search history.

(56) References Cited

U.S. PATENT DOCUMENTS

| 5,532,167 | A | 7/1996 | Cantley et al. | 436/89 |
| 5,538,897 | A | 7/1996 | Yates, III et al. | 436/89 |
| 5,593,844 | A | 1/1997 | Carlsson et al. | 435/7.1 |
| 5,716,836 | A | 2/1998 | Suiko | 435/240.27 |
| 5,759,787 | A | 6/1998 | Strulovici | 435/7.4 |
| 5,885,841 | A | 3/1999 | Higgs, Jr. et al. | 436/89 |
| 5,932,102 | A | 8/1999 | Wyllie et al. | 210/635 |
| 5,965,352 | A | 10/1999 | Stoughton et al. | 435/4 |
| 6,001,580 | A | 12/1999 | Tani et al. | 435/7.1 |
| 6,017,693 | A | 1/2000 | Yates, III et al. | 435/5 |
| 6,291,645 | B1 | 9/2001 | Shin et al. | 530/350 |
| 6,322,970 | B1 | 11/2001 | Little et al. | 435/6 |
| 6,379,970 | B1 | 4/2002 | Liebler et al. | 436/86 |
| 6,441,140 | B1 | 8/2002 | Comb et al. | 530/387.1 |
| 6,451,591 | B1 | 9/2002 | Edwards | 435/305.2 |
| 6,576,469 | B1 | 6/2003 | Struhl et al. | 435/483 |
| 6,579,720 | B1 | 6/2003 | Pidgeon et al. | 436/161 |
| 6,818,454 | B2 | 11/2004 | Goshe et al. | 436/173 |
| 6,982,318 | B1 | 1/2006 | Comb et al. | 530/387.1 |
| 7,198,896 | B2 | 4/2007 | Rush et al. | 435/6 |
| 7,259,022 | B2 | 8/2007 | Comb et al. | 436/547 |
| 7,300,753 | B2 | 11/2007 | Rush et al. | 435/6 |
| 7,344,714 | B2 | 3/2008 | Comb et al. | 424/139.1 |

| 2006/0148093 | A1 | 7/2006 | Gygi et al. | 436/173 |
| 2008/0008699 | A1 | 1/2008 | Li et al. | 424/130.1 |
| 2009/0022659 | A1* | 1/2009 | Olson et al. | 424/1.49 |
| 2009/0317409 | A1* | 12/2009 | Xu et al. | 424/184.1 |
| 2012/0149883 | A1 | 6/2012 | Gygi et al. | 530/388.1 |

FOREIGN PATENT DOCUMENTS

| WO | WO 99/19597 | 4/1999 | ............. E21B 10/18 |
| WO | WO 00/14536 | 3/2000 | ............. G01N 33/53 |
| WO | WO 01/27624 | 4/2001 | ........... G01N 33/543 |

OTHER PUBLICATIONS

Rudikoff et al (Proc Natl Acad Sci USA 1982 vol. 79 p. 1979-1983).*
al-Obeidi et al., "Protein tyrosine kinases: Structure, substrate specificity, and drug discovery," *Biopolymers*, vol. 47, pp. 197-223 (1998).
Alessi et al., "Mechanism of activation of protein kinase B by insulin and IGF-1," *The EMBO J.*, vol. 15, No. 23, pp. 6541-6551 (1996).
Alessi et al., "Molecular basis for the substrate specificity of protein kinase B; comparison with MAPKAP kinase-1 and p70 S6 kinase," *FEBS Lett.*, vol. 399, No. 3, pp. 333-338 (1996).
Bangalore et al., "Antiserum raised against a synthetic phosphotyrosine-containing peptide selectively recognized p185$^{new/erbB-2}$ and the epidermal growth factor receptor," *Proc. Natl. Acad. Sci. USA*, vol. 89, pp. 11637-11641 (1992).
Blaukat et al., "Determination of Bradykinin $B_2$ Receptor in Vivo Phosphorylation Sites and Their Role in Receptor Function," *J. Biol. Chem.*, vol. 276, No. 44, pp. 40431-40440 (2001).
Brumell et al., "Regulaton of Src Homology 2-containing Tyrosine Phosphatase 1 during Activation of Human Neutrophils," *J. Biol. Chem.*, vol. 272, No. 2, pp. 875-882 (1997).
Brunet et al., "Akt Promotes Cell Survival by Phosphorylating and Inhibiting a Forkhead Transcription Factor," *Cell*, vol. 96, pp. 857-868 (1999).
Burbelo et al., "14-3-3 Proteins: Hot numbers in signal transduction," *Curr. Biol.*, vol. 5, No. 2, pp. 95-96 (1995).
Cardone et al., "Regulation of Cell Death Protease Caspase-9 by Phosphorylation," *Science*, vol. 282, No. 5392, pp. 1318-1321 (1998).
Cantley, Cell Signaling Technology Inc.'s 2000-2001 Catalogue, p. 198.

(Continued)

*Primary Examiner* — Jacob Cheu

(57) ABSTRACT

The invention relates to antibody reagents that specifically bind to peptides carrying a ubiquitin remnant from a digested or chemically treated biological sample. The reagents allow the technician to identify ubiquitinated polypeptides as well as the sites of ubiquitination on them. The reagents are preferably employed in proteomic analysis using mass spectrometry. The antibody reagents specifically bind to the remnant of ubiquitin (i.e., a diglycine modified epsilon amine of lysine) left on a peptide which as been generated by digesting or chemically treating ubiquitinated proteins. The inventive antibody reagents' affinity to the ubiquitin remnant does not depend on the remaining amino acid sequences flanking the modified (i.e., ubiquitinated) lysine, i.e., they are context independent.

7 Claims, 2 Drawing Sheets

(56) References Cited

OTHER PUBLICATIONS

Chirica et al., "Fritless Capillary Columns for HPLC and CEC Prepared by Immobilizing the Stationary Phase in an Organic Polymer Matrix," *Anal. Chem.*, vol. 72, No. 15, pp. 3605-3610 (2000).
Conrads et al., "An enriched look at tryrosine phosphorylation," *Nat. Biotech.*, vol. 23, No. 1, pp. 36-37 (2005).
Cowley et al., "Activation of MAP kinase kinase is necessary and sufficient for PC12 differentiation and for transformation of NIH 3T3 cells," *Cell*, vol. 77, No. 6, pp. 841-852 (1994).
Czernik et al., "Production of phosphorylation state-specific antibodies." *Methods Enzymol.*, vol. 201, pp. 264-283 (1991).
Czernik et al., *Neuroprot.*, vol. 6, pp. 56-61 (1995).
Dalby et al., Identification of Regulatory Phosphoylation Sites in Mitogen-activated Protein Kinase (MAPK)-activated Protein Kinase-1a/p90$^{rsk}$ That Are Inducible by MAPK, *J. Biol. Chem.*, vol. 273, No. 3, pp. 1496-1505 (1998).
Datta et al., "Akt phosphorylation of BAD couples survival signals to the cell-intrinsic death machinery," *Cell* vol. 91, No. 2, pp. 231-241 (1997).
De Corte et al., "Identification of Tyr438 as the Major in vitro c-Src Phosphorylation Site in Human Gesolin: a Mass Spectrometric Approach," *Prot. Sci.*, vol. 8, pp. 234-241 (1999).
Dourtoglou et al., *Synthesis*, vol. 1984, pp. 572-574 (1984).
Erdument-Bromage et al., "Examination of Micro-Tip Reversed-Phase Liquid Chromatographic Extraction of Peptide Pools for Mass Spectrometric Analysis," *J. Chromatogr. A*, vol. 826, No. 2, pp. 167-181 (1998).
Fields et al., *Pept. Res.*, vol. 4, pp. 95-101 (1991).
Frackelton et al., "Generation of monoclonal antibodies against phosphotyrosine and their use for affinity purification of phosphotyrosine-containing proteins," *Method. Enzymol.*, vol. 201, pp. 79-92 (1991).
Franke et al., "PI3K: downstream AKTion blocks apoptosis." *Cell*, vol. 88, No. 4, pp. 435-437 (1997).
Fukunaga et al., "MNK1, a new MAP kinase-activated protein kinase, isolated by a novel expression screening method for identifying protein kinase substrates." *The EMBO J.*, vol. 16, No. 8, pp. 1921-1933 (1997).
Gaitlin et al., "Protein Identification at the Low Femtomole Level from Silver-Stained Gels Using a New Fritless Electrospray Interface for Liquid Chromatography-Microspray and Nanospray Mass Spectrometry," *Analytical Biochemistry*, vol. 263, pp. 93-101 (1998).
Gielbert et al., "Immunoaffinity Extraction Liquid Chromatography Mass Spectrometry with Monolithic Supports," Abstract MPA: 029, *50th ASMS Conference on Mass Spectometry and Allied Topics* (2002).
Glenney, *Method. Enzymol.*, vol. 201, pp. 92-100 (1991).
Godovac-Zimmermann et al., "Functional Proteomics of Signal Transduction by Membrane Receptors," *Electrophoresis*, vol. 20, No. 4, pp. 952-961 (1999).
Graves et al., "Protein Phosphorylation and Signal Transduction," *Pharmacol. Ther.*, vol. 82, Nos. 2-3, pp. 111-121 (1999).
Haley et al., "AACR Meeting Poster Presentation: Probing EGFr Signaling in HN5 Squamous Carcinoma Using the Quinazoline EGFr Inhibitor OSI-774 and Coupled Affinity Chromatography and Mass Spectrometry," www.aacr.org (2001).
Hamaguchi et al., "Phosphorylation of cellular proteins in Rous sarcoma virus-infected cells: analysis by use of anti-phosphotyrosine antibodies," *Molecular & Cellular Biology*, vol. 8, No. 8, pp. 3035-3042 (1988).
Heffetz et al., *Method. Enzymol.*, vol. 201, pp. 44-53 (1991).
Hoffman et al., "Site-specific immobilization of antibodies by their oligosaccharide moieties to new hydrazide derivatized solid supports," *J. Immun. Methods*, vol. 112, No. 1, pp. 113-120 (1988).
Hunter et al., "Oncogenic kinase signalling," *Nature*, vol. 411, pp. 355-365 (2001).
Huse et al., *Science*, vol. 246, pp. 1275-1281 (1989).
Imhof et al., *Curr. Biol.*, vol. 7, pp. 689-692 (1997).
Kalo et al., "Multiple In vivo Tyrosine Phosphorylation Sites in EphB Receptors," *Biochemistry*, vol. 38, No. 43, pp. 14396-14408 (1999).

Kamps, "Generation and Use of Anti-Phosphotyrosine Antibodies for Immunoblotting," *Methods in Enzymology*, vol. 201, pp. 101-111 (1991).
Kanner et al., "Immunoaffinity purification of tyrosine-phosphorylated cellular proteins," *J. Immunol. Methods*, vol. 120, No. 1, pp. 115-124 (1989).
Karin, *Curr. Opin. Cell Biol.*, vol. 6, pp. 415-424 (1994).
Kearney et al., "A New Mouse Myeloma Cell Line that Has Lost Immunoglobulin Expression but Permits the Construction of Antibody-Secreting Hybrid Cell Lines," *J. Immunol.*, vol. 123, No. 4, pp. 1548-1550 (1979).
Kemp et al., "Protein kinase recognition sequence motifs," *Trends Biochem. Sci.*, vol. 15, No. 9, pp. 342-346 (1990).
Keranen et al., *Curr. Biol.*, vol. 5, pp. 1395-1403 (1995).
Knorr et al., *Peptides*, vol. 1988, pp. 37-39 (1989).
Knorr et al., *Tetra. Lett.*, vol. 30, pp. 1927-1930 (1989).
Kozma et al., "Comparison of three methods for detecting tyrosine-phosphorylated proteins," *Methods Enzymol.*, vol. 201, pp. 28-43 (1991).
Kushima et al., "Characterization of HPC-1 antigen, an isoform of syntaxin-1, with the isoform-specific monoclonal antibody, 14D8," *J. Mol. Neurosci.*, vol. 8, No. 1, pp. 19-26 (1997).
Lewis et al., "Signal transduction through MAP kinase cascades," *Adv. Cancer Res.*, vol. 74, pp. 49-139 (1998).
Mann et al., "Analysis of Proteins and Proteomes by Mass Spectrometry," *Annu. Rev. Biochem.*, vol. 70, pp. 437-473 (2001).
Mann et al., "Analysis of protein phosphorylation using mass spectrometry: deciphering the phosphoproteome," *Trends in Biotechnology*, vol. 20, No. 6, pp. 261-268 (2002).
Mann et al., "Quantitative Proteomics," *Nat. Biotech.*, vol. 17, pp. 954-955 (1999).
Marcus et al., "Identification of platelet proteins separated by two-dimensional gel electrophoresis and analyzed by matrix assisted laser desorption/ionization-time of flight-mass spectrometry and detection of tyrosine-phosphorylated proteins Proteomics and 2-DE," *Electrophoresis*, vol. 21, No. 9, pp. 2622-2636 (2000).
Miceli et al., "Two-stage selection of sequences from a random phage display library delineates both core residues and permitted structural range within an epitope," *J. Immun. Methods*, vol. 167, Nos. 1-2, 3, pp. 279-287 (1994).
Montminy, "Transcriptional Regulation by Cyclic AMP," *Annu. Rev. Biochem.*, vol. 66, pp. 807-822 (1997).
Muslin et al., *Cell*, vol. 84, pp. 889-897 (1996).
New England BioLabs, Inc./Cell Signaling Technology, Inc., "General Phospho-Ser/Thr/Tyr Antibodies," *CST 2002 Catalog*, URL:http//www.neb.ca/detail.php?id=9920, 10 pages (Feb. 1, 2002).
Nishilawa et al., "Determination of the Specific Substrate Sequence Motifs of Protein Kinase C Isozymes," *J. Biol. Chem.*, vol. 272, No. 2, pp. 952-960 (1990).
Novagen, Novagen Technical Bulletin, pET System Manual, 9th Edition (2000).
Ouyang et al., "Multi-site Phosphotyping of the ErbB-2 Oncoprotein in Human Breast Cancer," *Molecular Diagnosis: A Journal Devoted to the Understanding of Human Disease Through the Clinical Application of Molecular Biology*, vol. 6, No. 1, pp. 17-25 (2001).
Pandey et al., "Identification of a novel immunoreceptor tyrosine-based activation motif-containing molecule, STAM2, by mass spectrometry and its involvement in growth factor and cytokine receptor signaling pathways," *J. Biol. Chem.*, vol. 49, pp. 38633-38639 (2000).
Pap et al., "Role of Glycogen Synthase Kinase-3 in the Phosphatidylinositol 3-Kinase/Akt Cell Survival Pathway," *J. Biol. Chem.*, vol. 273, No. 32, pp. 19929-19932 (1998).
Patterson et al., *Cell Biology: A Laboratory Handbook*, vol. 3, pp. 249-257, Academic Press (1994).
Patton, "Detection technologies in proteome analysis," *J. Chromatog. B*, vol. 771, Nos. 1-2, pp. 3-31 (2002).
Peng et al., *Science*, vol. 277, pp. 1501-1508 (1997).
Peters et al., "Exploring the Phosphoproteome with Mass Spectrometry," *Mini-Rev. Med. Chem.*, vol. 4, No. 3, pp. 313-324 (2004).
Posewitz et al., "Immobilized Gallium(III) Affinity Chromatography of Phosphopeptides," *Anal. Chem.*, vol. 71, No. 14, pp. 2883-2892 (1999).

(56) References Cited

OTHER PUBLICATIONS

Prat et al., "Bradykinin $B_1$ Receptor Expression and Function on T Lymphocytes in Active Mutiple Sclerosis," *Neurology*, vol. 53, pp. 2087-2092 (1999).
Quadroni et al., "Proteomics in Functional Genomics," *Review*, vol. 88, pp. 199-213 (2000).
Raggiaschi et al., "Phosphoproteome Analysis," *Biosci. Reports*, vol. 25, Nos. 1-2, pp. 33-44 (2005).
Raska et al., "Direct MALDI-MS/MS of Peptides Bound to Affinity Media," Abstract WPA 034, *50th ASMS Conference on Mass Spectometry and Allied Topics* (2002).
Reichmann et al., "Reshaping human antibodies for therapy," *Nature*, vol. 332, pp. 323-327 (1988).
Reinders et al., "State-of-the-art in phosphoproteomics," *Proteomics*, vol. 5, No. 16, pp. 4052-4061 (2005).
Rosenberg et al., "Characterization of a Distinct Binding Site for the Prokaryotic Chaperone, GroEL, on a Human Granulocyte Ribonuclease," *J. Biol. Chem.*, vol. 268, No. 6, pp. 4499-4503 (1993).
Ross et al., "Phosphotyrosine-containing proteins isolated by affinity chromatography with antibodies to synthetic hapten," *Nature*, vol. 294, pp. 654-656 (1981).
Shriver-Lake et al., "Antibody Immobilization using Heterobifunctional Crosslinkers," *Biosensors & Bioelectronics*, vol. 12, No. 11, pp. 1101-1106 (1997).
Songyang et al., "Use of an oriented peptide library to determine the optimal substrates of protein kinases," *Curr. Bio.*, vol. 4, No. 11, pp. 973-982 (1994).
Songyang et al., "A structural basis for substrate specificities of protein Ser/Thr-kinases: Primary sequence preference of casein kinase I and II, NIMA, phosphorylase kinase, CaM kinase II, CDK5 and Erk1," *Mol. Cell. Biol.*, vol. 16, pp. 6486-6493 (1996).
Steen et al., "Detection of Tyrosine Phosphorylated Peptides by Precursor Ion Scanning Quadrupole TOF Mass Spectrometry in Positive Ion Mode," *Anal. Chem.*, vol. 73, No. 7, pp. 1440-1448 (2001).
Struhl, "Histone acetylation and transcriptional regulatory mechanisms," *Genes & Dev.*, vol. 12, pp. 599-606 (1998).
Stukenberg et al., "Systematic identification of mitotic phosphoproteins," *Current Biology*, vol. 7, No. 5, pp. 338-348 (1997).
Suzuki et al., "Antibody specific for the Thr-286-autophosphorylated α subunit of $Ca^{2+}$/ calmodulin-dependent protein kinase II," *Proc. Natl. Acad. Sci. USA*, vol. 89, pp. 109-113 (1992).
Tomaino et al., "Phosphopeptide Detection by a Data-dependent, Neutral-loss Driven $MS^3$ Scan Usin Ion Trap Mass Spectrometry," *50th ASMS Conference on Mass Spectrometry and Allied Topics*, Abstract ThOE 3:00 (2002).
Verhoeven et al., "Reshaping human antibodies: Grafting an antilysozyme activity," *Science*, vol. 239, pp. 1534-1536 (1988).
Wang, "Generation and use of anti-phosphotyrosine antibodies raised against bacterially expressed abl protein," *Methods Enzymol.*, vol. 201, pp. 53-65 (1991).
Westendorf, "Cloning of cDNAs for M-phase phosphoproteins recognized by the MPM2 monoclonal antibody and determination of the phosphorylated epitope," *Proc. Natl. Acad. Sci.* USA, vol. 91, pp. 714-718 (1994).
Wettenhall et al., "Solid-phase sequencing of 32p labeled phosphopeptides," *Methods Enzymol.*, vol. 201, pp. 186-199 (1991).
White et al., "Preparation and use of anti-phosphotyrosine antibodies to study structure and function of insulin receptor," *Methods Enzymol.*, vol. 201, pp. 65-79 (1991).
Wirth et al., "The rat liver epithelial (RLE) cell nuclear protein database," *Electrophoresis*, vol. 14, No. 11, pp. 1199-1215 (1993).
Yaffe et al., "The Structural Basis for 14-3-3: Phosphopeptide Binding Specificity," *Cell*, vol. 91, pp. 961-971 (1997).
Yaffe et al., "Sequence-specific and phosphorylation-dependent proline isomerization: a potential mitotic regulatory mechanism," *Science*, vol. 278, No. 5345, pp. 1957-1960 (1997).
Yaffe et al., "A motif-based profile scanning approach for genome-wide prediction of signaling pathways," *Nature Biotech.*, vol. 19, pp. 348-353 (2001).
Yanagida et al., "Matrix Assisted Laser Desorption/Ionization-Time of Flight-Mass Spectrometry Analysis of Proteins Detected by Anti-Phosphotyrosine Antibody on Two-Dimensional Gels of Fibrolast Cell Lysates After Tumor Necrosis Factor-α Stimulation," *Electrophoresis*, vol. 21, No. 9, pp. 1890-1898 (2000).
Yates, III. et al., "SEQUEST," www.scripps.edu, 1 page (1999).
Yu et al., "Epitope mapping of monoclonal antibodies by mass spectrometry: identification of protein antigens in complex biological systems," *J. Am. Soc. Mass. Spectrom.*, vol. 9, No. 3, pp. 208-215 (1998).
Zha et al., "Serine Phosphorylation of Death Agonist Bad in Response to Survival Factor Results in Binding to 14-3-3 Not BCL-X," *Cell*, vol. 87, No. 4, pp. 619-628 (1996).
*Antibodies: A Laboratory Manual*, Chapter 5, pp. 72-77, Cold Spring Harbor Laboratory Press, eds. Harlow et al. (1988).
*Antibodies: A Laboratory Manual*, Cold Spring Harbor Laboratory Press, eds. Harlow et al. (1988).
*Current Protocols in Immunology*, Unit 9.3: Selection of Immunogenic Peptides for Antisera Production 9.31-9.3.3 (1991).
*Monoclonal Antibodies, Hybridomas: A New Dimension in Biological Analyses*, Kennett et al. (eds), Plenum Press (1980).
"Protein Phosphorylation, Part B: Analysis of Protein Phosphorylation, Protein Kinase Inhibitors and Protein Phosphatases," *Methods Enzym.*, vol. 201, pp. 3-547, eds. Hunter et al. (1991).
Protein Phosphorylation: A Practical Approach, ed. Hardie, p. 267, IRL Press (1993).
Sigma 1998 Catalog, pp. 1305 and 1309.
Upstate Biotechnology 1998 Catalog, p. 17.
Zymed Laboratories 1996-1997 General Catalog, p. 80.
United States Patent and Trademark Office, Office Action dated Dec. 4, 2012 pertaining to U.S. Appl. No. 12/967,284, 43 pages.

* cited by examiner

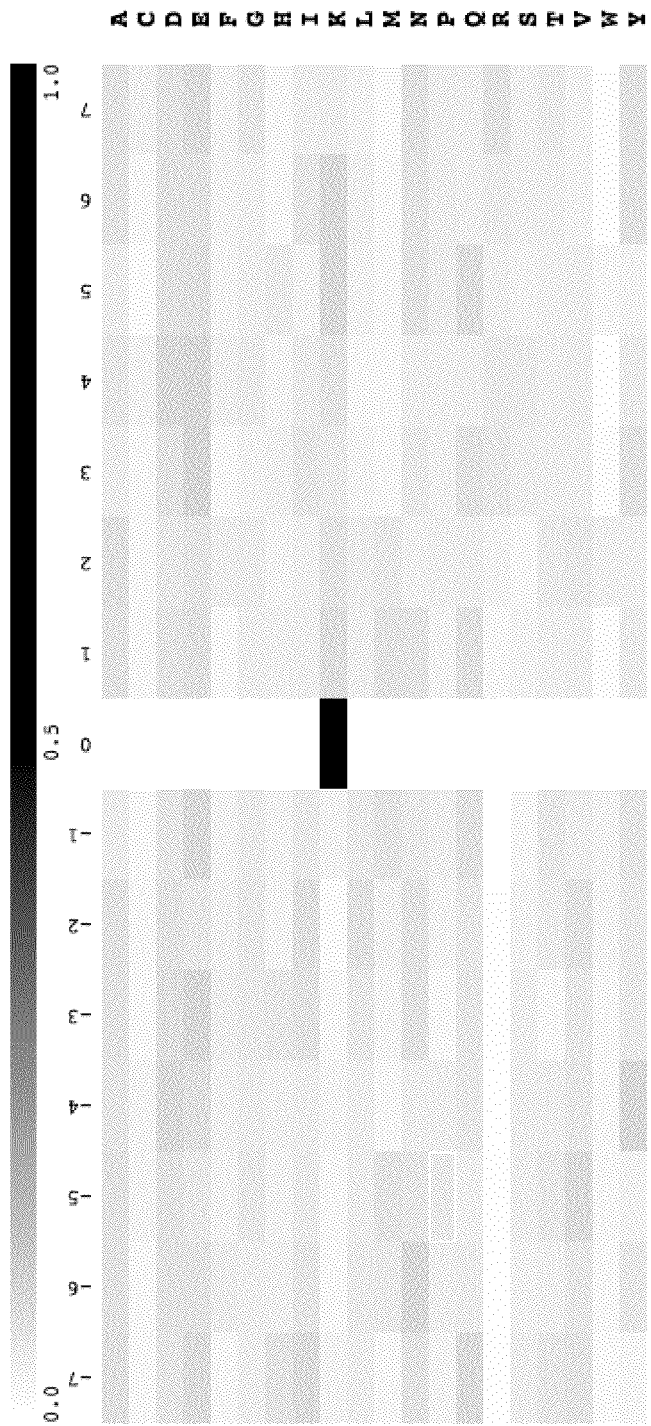
Figure 2: Heat map of ubiquitination peptides from MS

SEQUENCE LISTING

```
<160> NUMBER OF SEQ ID NOS: 602

<210> SEQ ID NO 1
<211> LENGTH: 471
<212> TYPE: PRT
<213> ORGANISM: Artificial Sequence
<220> FEATURE:
<223> OTHER INFORMATION: Synthetic Peptide

<400> SEQUENCE: 1

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Thr Ser Leu Thr Leu Thr Cys Thr Ala Ser Gly Phe Thr Ile Ser
        35                  40                  45

Ser Asn Tyr Tyr Ile Tyr Trp Val Arg Gln Ala Pro Gly Lys Gly Leu
    50                  55                  60

Glu Trp Ile Ala Cys Ile Tyr Gly Gly Ser Ser Gly Thr Thr Leu Tyr
65                  70                  75                  80

Ala Ser Trp Ala Lys Gly Arg Phe Thr Ile Ser Lys Thr Ser Ser Thr
                85                  90                  95

Thr Val Thr Leu Lys Met Pro Ser Leu Thr Ala Ala Asp Thr Ala Thr
            100                 105                 110

Tyr Phe Cys Ala Arg Asp Phe Arg Gly Ala Asp Tyr Ser Ser Tyr Asp
        115                 120                 125

Arg Ile Trp Asp Thr Arg Leu Asp Leu Trp Gly Gln Gly Thr Leu Val
    130                 135                 140

Thr Val Ser Ser Gly Gln Pro Lys Ala Pro Ser Val Phe Pro Leu Ala
145                 150                 155                 160
```

Pro Cys Cys Gly Asp Thr Pro Ser Ser Thr Val Thr Leu Gly Cys Leu
            165                 170                 175

Val Lys Gly Tyr Leu Pro Glu Pro Val Thr Val Thr Trp Asn Ser Gly
            180                 185                 190

Thr Leu Thr Asn Gly Val Arg Thr Phe Pro Ser Val Arg Gln Ser Ser
        195                 200                 205

Gly Leu Tyr Ser Leu Ser Ser Val Val Ser Val Thr Ser Ser Ser Gln
    210                 215                 220

Pro Val Thr Cys Asn Val Ala His Pro Ala Thr Asn Thr Lys Val Asp
225                 230                 235                 240

Lys Thr Val Ala Pro Ser Thr Cys Ser Lys Pro Thr Cys Pro Pro Pro
                245                 250                 255

Glu Leu Leu Gly Gly Pro Ser Val Phe Ile Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Asp Asp Pro Glu Val Gln Phe Thr Trp Tyr Ile Asn
    290                 295                 300

Asn Glu Gln Val Arg Thr Ala Arg Pro Pro Leu Arg Glu Gln Gln Phe
305                 310                 315                 320

Asn Ser Thr Ile Arg Val Val Ser Thr Leu Pro Ile Ala His Gln Asp
                325                 330                 335

Trp Leu Arg Gly Lys Glu Phe Lys Cys Lys Val His Asn Lys Ala Leu
            340                 345                 350

Pro Ala Pro Ile Glu Lys Thr Ile Ser Lys Ala Arg Gly Gln Pro Leu
        355                 360                 365

Glu Pro Lys Val Tyr Thr Met Gly Pro Pro Arg Glu Glu Leu Ser Ser
    370                 375                 380

Arg Ser Val Ser Leu Thr Cys Met Ile Asn Gly Phe Tyr Pro Ser Asp
385                 390                 395                 400

Ile Ser Val Glu Trp Glu Lys Asn Gly Lys Ala Glu Asp Asn Tyr Lys
                405                 410                 415

Thr Thr Pro Ala Val Leu Asp Ser Asp Gly Ser Tyr Phe Leu Tyr Ser
            420                 425                 430

Lys Leu Ser Val Pro Thr Ser Glu Trp Gln Arg Gly Asp Val Phe Thr
        435                 440                 445

Cys Ser Val Met His Glu Ala Leu His Asn His Tyr Thr Gln Lys Ser
    450                 455                 460

Ile Ser Arg Ser Pro Gly Lys
465                 470

<210> SEQ ID NO 2
<211> LENGTH: 238
<212> TYPE: PRT
<213> ORGANISM: Artificial Sequence
<220> FEATURE:
<223> OTHER INFORMATION: Synthetic Peptide

<400> SEQUENCE: 2

Met Asp Met Arg Ala Pro Thr Gln Leu Leu Gly Leu Leu Leu Leu Trp
1               5                   10                  15

Leu Pro Gly Val Thr Phe Ala Ala Val Leu Thr Gln Thr Pro Ser Pro
            20                  25                  30

Val Ser Ala Ala Val Gly Gly Thr Val Ser Ile Ser Cys Gln Ser Ser
        35                  40                  45

```
Glu Asn Val Tyr Asn Lys Asn Trp Leu Ser Trp Tyr Gln Gln Lys Pro
 50                  55                  60
Gly Gln Pro Pro Lys Leu Ile Gln Lys Ala Ser Thr Leu Ala Ser
 65                  70                  75                  80
Gly Val Pro Ser Arg Phe Lys Gly Ser Gly Ser Gly Thr Gln Phe Thr
                 85                  90                  95
Leu Thr Ile Ser Asp Leu Glu Cys Ala Asp Ala Ala Thr Tyr Tyr Cys
                100                 105                 110
Ala Gly Asp Tyr Gly Gly Thr Gly Asp Ala Phe Val Phe Gly Gly Gly
            115                 120                 125
Thr Glu Val Val Val Lys Gly Asp Pro Val Ala Pro Thr Val Leu Ile
        130                 135                 140
Phe Pro Pro Ala Ala Asp Gln Val Ala Thr Gly Thr Val Thr Ile Val
145                 150                 155                 160
Cys Val Ala Asn Lys Tyr Phe Pro Asp Val Thr Val Thr Trp Glu Val
                165                 170                 175
Asp Gly Thr Thr Gln Thr Thr Gly Ile Glu Asn Ser Lys Thr Pro Gln
            180                 185                 190
Asn Ser Ala Asp Cys Thr Tyr Asn Leu Ser Ser Thr Leu Thr Leu Thr
        195                 200                 205
Ser Thr Gln Tyr Asn Ser His Lys Glu Tyr Thr Cys Lys Val Thr Gln
    210                 215                 220
Gly Thr Thr Ser Val Val Gln Ser Phe Asn Arg Gly Asp Cys
225                 230                 235

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 3

Gly Phe Thr Ile Ser Ser Asn Tyr Tyr Ile Tyr Trp Val
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 4

Cys Ile Tyr Gly Gly Ser Ser Gly Thr Thr Leu Tyr Ala Ser Trp Ala
1               5                   10                  15
Lys Gly

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

Asp Phe Arg Gly Ala Asp Tyr Ser Ser Tyr Asp Arg Ile Trp Asp Thr
1               5                   10                  15
Arg Leu Asp Leu
```

```
                    20

<210> SEQ ID NO 6
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 6

Asp Phe Arg Gly Ala Asp Tyr Ser Ser Tyr Asp Arg Ile Trp Asp Thr
1               5                   10                  15

Arg Leu Asp Leu
            20

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Lys Ala Ser Thr Leu Ala Ser
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Ala Gly Asp Tyr Gly Gly Thr Gly Asp Ala Phe Val
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Met Gln Ile Phe Val Lys Thr Leu Thr Gly Lys
1               5                   10

<210> SEQ ID NO 10
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 10

Thr Leu Thr Gly Lys Thr Ile Thr Leu Glu Val Glu Pro Ser Asp Thr
1               5                   10                  15

Ile Glu Asn Val Lys
            20

<210> SEQ ID NO 11
<211> LENGTH: 23
<212> TYPE: PRT
<213> ORGANISM: Artificial Sequence
<220> FEATURE:
```

<223> OTHER INFORMATION: Synthetic Peptide

<400> SEQUENCE: 11

Thr Leu Thr Gly Lys Thr Ile Thr Leu Glu Val Glu Pro Ser Asp Thr
1               5                   10                  15
Ile Glu Asn Val Lys Ala Lys
            20

<210> SEQ ID NO 12
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 12

Thr Ile Thr Leu Glu Val Glu Pro Ser Asp Thr Ile Glu Asn Val Lys
1               5                   10                  15
Ala Lys Ile Gln Asp Lys Glu Gly Ile Pro Pro Asp Gln Gln Arg
            20                  25                  30

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Ala Lys Ile Gln Asp Lys Glu Gly Ile Pro Pro Asp Gln Gln Arg
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Ala Lys Ile Gln Asp Lys Glu Gly Ile Pro Pro Asp Gln Gln Arg
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 15

Ile Gln Asp Lys Glu Gly Ile Pro Pro Asp Gln Gln Arg
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Ala Lys Ile Gln Asp Lys Glu Gly Ile Pro Pro Asp Gln Gln Arg
1               5                   10                  15

```
<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Ala Lys Ile Gln Asp Lys Glu Gly Ile Pro Pro Asp Gln Gln Arg
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 18

Leu Ile Phe Ala Gly Lys Gln Leu Glu Asp Gly Arg
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 19

Leu Ile Phe Ala Gly Lys Gln Leu Glu Asp Gly Arg Thr Leu Ser Asp
1               5                   10                  15

Tyr Asn Ile Gln Lys
            20

<210> SEQ ID NO 20
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 20

Leu Ile Phe Ala Gly Lys Gln Leu Glu Asp Gly Arg Thr Leu Ser Asp
1               5                   10                  15

Tyr Asn Ile Gln Lys Glu Ser Thr Leu His Leu Val Leu Arg
            20                  25                  30

<210> SEQ ID NO 21
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 21

Thr Leu Ser Asp Tyr Asn Ile Gln Lys Glu Ser Thr Leu His Leu Val
1               5                   10                  15

Leu Arg

<210> SEQ ID NO 22
<211> LENGTH: 14
<212> TYPE: PRT
<213> ORGANISM: Artificial Sequence
<220> FEATURE:
<223> OTHER INFORMATION: Synthetic Peptide
```

<400> SEQUENCE: 22

Met Ser Leu Lys Gly Thr Thr Val Thr Pro Asp Lys Arg Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 23

Met Ser Leu Lys Gly Thr Thr Val Thr Pro Asp Lys Arg
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 24

Met Ser Leu Lys Gly Thr Thr Val Thr Pro Asp Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Met Ser Leu Lys Gly Thr Thr Val Thr Pro Asp Lys Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 26

Met Ser Leu Lys Gly Thr Thr Val Thr Pro Asp Lys Arg Lys
1               5                   10

<210> SEQ ID NO 27
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 27

Met Gln Glu Asp Ile Glu Met Thr Lys Thr Gln Ser Ile Tyr Asp Asp
1               5                   10                  15

Lys Asn His Arg
            20

<210> SEQ ID NO 28
<211> LENGTH: 19
<212> TYPE: PRT
<213> ORGANISM: Artificial Sequence

```
<220> FEATURE:
<223> OTHER INFORMATION: Synthetic Peptide

<400> SEQUENCE: 28

Lys Ala Ser Gly Pro Pro Val Ser Glu Leu Ile Thr Lys Ala Val Ala
1               5                   10                  15

Ala Ser Lys

<210> SEQ ID NO 29
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 29

Lys Ala Leu Ala Ala Ala Gly Tyr Asp Val Glu Lys
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 30

Lys Ala Leu Ala Ala Ala Gly Tyr Asp Val Glu Lys Asn Asn Ser Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31

Ala Leu Ala Ala Ala Gly Tyr Asp Val Glu Lys Asn Asn Ser Arg
1               5                   10                  15

<210> SEQ ID NO 32
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 32

Lys Thr Ser Gly Pro Pro Val Ser Glu Leu Ile Thr Lys Ala Val Ala
1               5                   10                  15

Ala Ser Lys

<210> SEQ ID NO 33
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 33

Thr Ser Gly Pro Pro Val Ser Glu Leu Ile Thr Lys Ala Val Ala Ala
1               5                   10                  15

Ser Lys
```

-continued

<210> SEQ ID NO 34
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 34

Val Thr Ile Ala Gln Gly Gly Val Leu Pro Asn Ile Gln Ala Val Leu
1               5                   10                  15

Leu Pro Lys Lys Thr Glu Ser His His Lys
            20                  25

<210> SEQ ID NO 35
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 35

Val Thr Ile Ala Gln Gly Gly Val Leu Pro Asn Ile Gln Ala Val Leu
1               5                   10                  15

Leu Pro Lys Lys Thr Glu Ser His His Lys
            20                  25

<210> SEQ ID NO 36
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 36

Val Thr Ile Ala Gln Gly Gly Val Leu Pro Asn Ile Gln Ala Val Leu
1               5                   10                  15

Leu Pro Lys Lys
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 37

Val Thr Ile Ala Gln Gly Gly Val Leu Pro Asn Ile Gln Ala Val Leu
1               5                   10                  15

Leu Pro Lys Lys
            20

<210> SEQ ID NO 38
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 38

Val Thr Ile Ala Gln Gly Gly Val Leu Pro Asn Ile Gln Ala Val Leu
1               5                   10                  15

Leu Pro Lys Lys Thr Glu Ser His His Lys Pro Lys
            20                  25

```
<210> SEQ ID NO 39
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 39

Val Thr Ile Ala Gln Gly Gly Val Leu Pro Asn Ile Gln Ala Val Leu
1               5                   10                  15

Leu Pro Lys Lys Thr Glu Ser Gln Lys
            20                  25

<210> SEQ ID NO 40
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 40

Val Thr Ile Ala Gln Gly Gly Val Leu Pro Asn Ile Gln Ala Val Leu
1               5                   10                  15

Leu Pro Lys Lys Thr Glu Ser Gln Lys
            20                  25

<210> SEQ ID NO 41
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 41

Gly Val Thr Ile Ala Ser Gly Gly Val Leu Pro Asn Ile His Pro Glu
1               5                   10                  15

Leu Leu Ala Lys Lys
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 42

Gly Val Thr Ile Ala Ser Gly Gly Val Leu Pro Asn Ile His Pro Glu
1               5                   10                  15

Leu Leu Ala Lys Lys Arg
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 43

Gly Val Thr Ile Ala Ser Gly Gly Val Leu Pro Asn Ile His Pro Glu
1               5                   10                  15

Leu Leu Ala Lys Lys Arg
```

```
<210> SEQ ID NO 44
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 44

Val Thr Ile Ala Gln Gly Gly Val Leu Pro Asn Ile Gln Ala Val Leu
1               5                  10                  15

Leu Pro Lys Lys Thr Glu Thr His His Lys
            20                  25

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 45

Lys Ser Ser Ala Thr Val Gly Pro Lys
1               5

<210> SEQ ID NO 46
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 46

Leu Leu Gly Gly Val Thr Ile Ala Gln Gly Gly Val Leu Pro Asn Ile
1               5                  10                  15

Gln Ala Val Leu Leu Pro Lys Lys
            20

<210> SEQ ID NO 47
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 47

Asn Asp Glu Glu Leu Asn Lys Leu Leu Gly Gly Val Thr Ile Ala Gln
1               5                  10                  15

Gly Gly Val Leu Pro Asn Ile Gln Ala Val Leu Leu Pro Lys Lys
            20                  25                  30

<210> SEQ ID NO 48
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 48

Ala Val Thr Lys Tyr Thr Ser Ser Lys
1               5

<210> SEQ ID NO 49
<211> LENGTH: 14
```

```
<212> TYPE: PRT
<213> ORGANISM: Artificial Sequence
<220> FEATURE:
<223> OTHER INFORMATION: Synthetic Peptide

<400> SEQUENCE: 49

Val Leu Lys Gln Val His Pro Asp Thr Gly Ile Ser Ser Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 50

His Ala Val Ser Glu Gly Thr Lys Ala Val Thr Lys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 51

Ala Val Thr Lys Tyr Thr Ser Ala Lys
1               5

<210> SEQ ID NO 52
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 52

Val Thr Ile Ala Gln Gly Gly Val Leu Pro Asn Ile Gln Ala Val Leu
1               5                   10                  15

Leu Pro Lys Lys Thr Glu Ser His Lys
            20                  25

<210> SEQ ID NO 53
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 53

Val Thr Ile Ala Gln Gly Gly Val Leu Pro Asn Ile Gln Ala Val Leu
1               5                   10                  15

Leu Pro Lys Lys Thr Glu Ser His Lys
            20                  25

<210> SEQ ID NO 54
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 54

Ile Thr Ile Thr Asn Asp Lys Gly Arg
```

```
<210> SEQ ID NO 55
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 55

Leu Ile Tyr Ser Gly Lys Gln Met Asn Asp Glu Lys
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 56

Asp Thr Gly Lys Thr Pro Val Glu Pro Glu Val Ala Ile His Arg
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 57

Ser Ser His Pro Ser Glu Pro Pro Lys Glu Ala Ser Gly Thr Asp Val
1               5                   10                  15

Arg

<210> SEQ ID NO 58
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 58

Glu Ala Phe Ser Ser Val Ile Ile Lys Glu Pro Gln Ile Glu Pro Thr
1               5                   10                  15

Ala Asp Leu Thr Gly Ile Thr Asn Gln Leu Ile Thr Cys Lys
            20                  25                  30

<210> SEQ ID NO 59
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 59

Val Gly Ile Asn Tyr Gln Pro Pro Thr Val Val Pro Gly Gly Asp Leu
1               5                   10                  15

Ala Lys Val Gln Arg
            20

<210> SEQ ID NO 60
<211> LENGTH: 21
<212> TYPE: PRT
```

```
<213> ORGANISM: Artificial Sequence
<220> FEATURE:
<223> OTHER INFORMATION: Synthetic Peptide

<400> SEQUENCE: 60

Thr Leu Thr Gly Lys Thr Ile Thr Leu Glu Val Glu Pro Ser Asp Thr
1               5                   10                  15

Ile Glu Asn Val Lys
            20

<210> SEQ ID NO 61
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 61

Met Gln Ile Phe Val Lys Thr Leu Thr Gly Lys
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 62

Ala Lys Ile Gln Asp Lys Glu Gly Ile Pro Pro Asp Gln Gln Arg
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 63

Ala Lys Ile Gln Asp Lys Glu Gly Ile Pro Pro Asp Gln Gln Arg
1               5                   10                  15

<210> SEQ ID NO 64
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 64

Ile Gln Asp Lys Glu Gly Ile Pro Pro Asp Gln Gln Arg
1               5                   10

<210> SEQ ID NO 65
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 65

Ala Lys Ile Gln Asp Lys Glu Gly Ile Pro Pro Asp Gln Gln Arg
1               5                   10                  15

<210> SEQ ID NO 66
```

```
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 66

Leu Ile Phe Ala Gly Lys Gln Leu Glu Asp Gly Arg
1               5                   10

<210> SEQ ID NO 67
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 67

Leu Ile Phe Ala Gly Lys Gln Leu Glu Asp Gly Arg Thr Leu Ser Asp
1               5                   10                  15

Tyr Asn Ile Gln Lys
            20

<210> SEQ ID NO 68
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 68

Leu Ile Phe Ala Gly Lys Gln Leu Glu Asp Gly Arg Thr Leu Ser Asp
1               5                   10                  15

Tyr Asn Ile Gln Lys Glu Ser Thr Leu His Leu Val Leu Arg
            20                  25                  30

<210> SEQ ID NO 69
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 69

Thr Leu Ser Asp Tyr Asn Ile Gln Lys Glu Ser Thr Leu His Leu Val
1               5                   10                  15

Leu Arg

<210> SEQ ID NO 70
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 70

Cys Pro Gly Leu Leu Thr Pro Ser Gln Ile Lys Pro Gly Thr Tyr Lys
1               5                   10                  15

Leu Phe Phe Asp Thr Glu Arg
            20

<210> SEQ ID NO 71
<211> LENGTH: 19
<212> TYPE: PRT
<213> ORGANISM: Artificial Sequence
```

```
<220> FEATURE:
<223> OTHER INFORMATION: Synthetic Peptide

<400> SEQUENCE: 71

Ser Met Leu Glu Ala His Gln Ala Lys His Val Lys Gln Leu Leu Ser
1               5                   10                  15

Lys Pro Arg

<210> SEQ ID NO 72
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 72

Asn Leu Leu Ser Val Ala Tyr Lys Asn Val Val Gly Ala Arg
1               5                   10

<210> SEQ ID NO 73
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 73

Lys Gly Glu Ser Val Met Val Val Pro Thr Leu Ser Glu Glu Glu Ala
1               5                   10                  15

Lys Gln Cys Phe Pro Lys
            20

<210> SEQ ID NO 74
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 74

Lys Gly Glu Ser Val Met Val Val Pro Thr Leu Ser Glu Glu Glu Ala
1               5                   10                  15

Lys Gln Cys Phe Pro Lys
            20

<210> SEQ ID NO 75
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 75

Gly Val Phe Thr Lys Glu Leu Pro Ser Gly Lys
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 76

Thr Val Val Gly Lys Glu Glu Glu Gly Ser Asp Pro Glu Lys
```

```
1               5                   10
```

<210> SEQ ID NO 77
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 77

```
Thr Val Val Gly Lys Glu Glu Glu Gly Ser Asp Pro Glu Lys Ala Leu
1               5                   10                  15

Arg
```

<210> SEQ ID NO 78
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 78

```
Ser Glu Gly Lys Gln Asp Ala Leu Glu Glu Phe Lys
1               5                   10
```

<210> SEQ ID NO 79
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 79

```
Glu Ile Leu Glu Lys Ala Gly Gln Ile Thr Asn Glu Ala Leu Ser Asn
1               5                   10                  15

Ile Arg
```

<210> SEQ ID NO 80
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 80

```
Met Leu Thr Gly Phe Ala Ser Gln Asp Lys Glu Ile Leu Glu Lys Ala
1               5                   10                  15

Gly Gln Ile Thr Asn Glu Ala Leu Ser Asn Ile Arg
            20                  25
```

<210> SEQ ID NO 81
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 81

```
Met Leu Thr Gly Phe Ala Ser Gln Asp Lys Glu Ile Leu Glu Lys Ala
1               5                   10                  15

Gly Gln Ile Thr Asn Glu Ala Leu Ser Asn Ile Arg
            20                  25
```

<210> SEQ ID NO 82

```
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 82

Lys Ile Gln Val Gln Asn Met Lys Asn Lys
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 83

Ile Gln Val Gln Asn Met Lys Asn Lys
1               5

<210> SEQ ID NO 84
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 84

Phe Leu Leu Lys Ser Cys Pro Leu Leu Thr Lys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 85

Gly Lys Tyr Lys Glu Glu Thr Ile Glu Lys
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 86

Arg Ser Lys Ala Glu Glu Leu Gly Leu Pro Ile Leu Gly Val Leu Arg
1               5                   10                  15

<210> SEQ ID NO 87
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 87

Ile Gln Pro Gln Gln Val Ala Val Trp Pro Thr Leu Val Asp Ile Asn
1               5                   10                  15

Ser Leu Asp Ser Leu Thr Glu Ala Tyr Lys Leu Arg
            20                  25
```

```
<210> SEQ ID NO 88
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 88

Val Tyr Asp Lys Val Gln Asn Glu Ala Lys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 89

Asn Gln Cys Val Lys Glu Ala Ile Leu Glu Asp Leu Gln Lys
1               5                   10

<210> SEQ ID NO 90
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 90

Phe Phe Gln Thr Gln Ile Lys Ser Leu Tyr Glu Ser Ile Glu Glu
1               5                   10                  15

<210> SEQ ID NO 91
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 91

Asp Leu Thr Asp Tyr Leu Met Lys Ile Leu Thr Glu Arg
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 92

Glu Ile Thr Ala Leu Ala Pro Ser Thr Met Lys Ile Lys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 93

His Val Ala Asp Glu Met Leu Lys Asp Met Lys Lys
1               5                   10
```

```
<210> SEQ ID NO 94
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 94

Ile Lys Met Val Ala Thr Gly Val Cys Arg
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 95

Ile Cys Lys His Pro Glu Ser Asn Phe Cys Ser Arg
1               5                   10

<210> SEQ ID NO 96
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 96

Ile Asp Gly Ala Ser Pro Leu Asp Lys Val Cys Leu Ile Gly Cys Gly
1               5                   10                  15

Phe Ser Thr Gly Tyr Gly Ser Ala Val Lys
            20                  25

<210> SEQ ID NO 97
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 97

Ile Asp Gly Ala Ser Pro Leu Asp Lys Val Cys Leu Ile Gly Cys Gly
1               5                   10                  15

Phe Ser Thr Gly Tyr Gly Ser Ala Val Lys Val Ala Lys
            20                  25

<210> SEQ ID NO 98
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 98

Thr Trp Lys Gly Ala Ile Phe Gly Gly Phe Lys
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 99
```

```
Leu Val Ala Asp Phe Met Ala Lys Lys
1               5

<210> SEQ ID NO 100
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 100

Ala Ala Thr Phe Phe Gly Cys Ile Gly Ile Asp Lys Phe Gly Glu Ile
1               5                   10                  15

Leu Lys

<210> SEQ ID NO 101
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 101

Glu Gln Gly Phe Glu Thr Lys Asp Ile Lys
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 102

Thr Gly Cys Thr Phe Pro Glu Lys Pro Asp Phe His
1               5                   10

<210> SEQ ID NO 103
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 103

Glu Lys Gln Trp Val Asp Gln Ser Ser Pro Val Leu Leu Asp Asn Pro
1               5                   10                  15

Val Leu Gly Ser Met Ala Lys
            20

<210> SEQ ID NO 104
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 104

Tyr Ile Ser Gly Ser Ser Phe Lys Asp His Pro Asp Phe Pro Phe Trp
1               5                   10                  15

Asp Glu Tyr

<210> SEQ ID NO 105
<211> LENGTH: 22
```

```
<212> TYPE: PRT
<213> ORGANISM: Artificial Sequence
<220> FEATURE:
<223> OTHER INFORMATION: Synthetic Peptide

<400> SEQUENCE: 105

Val Pro Lys Asp Glu Gln Gly Ser Ala Ala Asp Ser Glu Asp Ser Pro
1               5                   10                  15

Thr Ile Glu Ala Val Arg
            20

<210> SEQ ID NO 106
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 106

Cys Val Leu Ile Phe Gly Val Pro Ser Arg Val Pro Lys Asp Glu Gln
1               5                   10                  15

Gly Ser Ala Ala Asp Ser Glu Asp Ser Pro Thr Ile Glu Ala Val Arg
            20                  25                  30

<210> SEQ ID NO 107
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 107

Ala Ala Leu Leu Lys His Gly Leu Gly Asn Arg
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 108

Val Gly Thr Lys Cys Cys Thr Leu Pro Glu Asp Gln Arg
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 109

Arg Lys Pro Val Leu Thr Ser Gln Leu Glu Arg
1               5                   10

<210> SEQ ID NO 110
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 110

Ala Asn Asn Thr Thr Tyr Gly Leu Ala Ala Gly Leu Phe Thr Lys Asp
```

```
                1               5                   10                  15

Leu Asp Lys

<210> SEQ ID NO 111
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 111

Arg Ala Asn Asn Thr Thr Tyr Gly Leu Ala Ala Gly Leu Phe Thr Lys
1               5                   10                  15

Asp Leu Asp Lys
            20

<210> SEQ ID NO 112
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 112

Ile Phe Val Glu Glu Ser Ile Tyr Glu Glu Phe Val Lys
1               5                   10

<210> SEQ ID NO 113
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 113

Ala Asn Asn Thr Thr Tyr Gly Leu Ala Ala Gly Val Phe Thr Lys Asp
1               5                   10                  15

Leu Asp Lys

<210> SEQ ID NO 114
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 114

Thr Val Ala Met Gln Ile Ser Gln Lys Asn Ser
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 115

Leu Leu Asn Lys Leu Ala Asp Leu Met Glu Arg Asp Arg
1               5                   10

<210> SEQ ID NO 116
<211> LENGTH: 11
<212> TYPE: PRT
<213> ORGANISM: Artificial Sequence
```

```
<220> FEATURE:
<223> OTHER INFORMATION: Synthetic Peptide

<400> SEQUENCE: 116

Leu Leu Asn Lys Leu Ala Asp Leu Met Glu Arg
1               5                   10

<210> SEQ ID NO 117
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 117

Leu Ile Lys Glu Ala Ala Gly Lys
1               5

<210> SEQ ID NO 118
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 118

Trp Gly Asn Lys Gly Phe Phe Val Gln Pro Thr Val Phe Ser Asn Val
1               5                   10                  15

Thr Asp Glu Met Arg
            20

<210> SEQ ID NO 119
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 119

Trp Gly Asn Lys Gly Phe Phe Val Gln Pro Thr Val Phe Ser Asn Val
1               5                   10                  15

Thr Asp Glu Met Arg
            20

<210> SEQ ID NO 120
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 120

Ile Ala Lys Glu Glu Ile Phe Gly Pro Val Gln Gln Ile Met Lys
1               5                   10                  15

<210> SEQ ID NO 121
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 121

Leu Gln Ser Leu Leu Lys Gly Gln Lys
1               5
```

<210> SEQ ID NO 122
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 122

Phe Gln Asp Glu Glu Glu Val Phe Glu Trp Asn Asn Glu Val Lys Gln
1               5                   10                  15

Gly Leu Ser Ser Ser Ile Phe Thr Lys
            20                  25

<210> SEQ ID NO 123
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 123

Ile Lys Val Glu Asn Thr Glu Glu Asn Arg Arg
1               5                   10

<210> SEQ ID NO 124
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 124

Gly Ile Val Val Gly Ile Lys Leu Asp Gln Gly Gly Ala Pro Leu Ala
1               5                   10                  15

Gly Thr Asn Lys
            20

<210> SEQ ID NO 125
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 125

Gly Ile Val Val Gly Ile Lys Leu Asp Gln Gly Gly Ala Pro Leu Ala
1               5                   10                  15

Gly Thr Asn Lys Glu Thr Thr Ile Gln Gly Leu Asp Gly Leu Ser Glu
            20                  25                  30

Arg

<210> SEQ ID NO 126
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 126

Leu Asp Gln Gly Gly Ala Pro Leu Ala Gly Thr Asn Lys Glu Thr Thr
1               5                   10                  15

Ile Gln Gly Leu Asp Gly Leu Ser Glu Arg
            20                  25

<210> SEQ ID NO 127
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 127

Ala Thr Gln Glu Ala Phe Met Lys Arg
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 128

Phe Ser Lys Ser Ala Asp Glu Arg
1               5

<210> SEQ ID NO 129
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 129

Phe Leu Asn Lys Ser Ser Glu Asp Asp Gly Ala Ser Glu Arg
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 130

Ala Ile Asn Glu Ala Tyr Lys Glu Asp Tyr His Lys
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 131

Ala Ala Ile Glu His Ile Lys Gln Lys
1               5

<210> SEQ ID NO 132
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 132

Leu Gly Lys Glu Val Gln Ala Ala Gln Ala Arg
1               5                   10

-continued

```
<210> SEQ ID NO 133
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 133

Ser Lys Met Glu Glu Gln Thr Gln Gln Ile Arg
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 134

Gly Met Lys Glu Val Leu Asp Gln Ser Gly Pro Arg
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 135

Ile Val Asn Lys Ile Pro Gln Ala Thr Arg
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 136

Gly Gly Val Glu Lys Gly Pro Ala Ala Leu Arg
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 137

Tyr Phe Ser Met Thr Glu Val Asp Lys Leu Gly Ile Gly Lys
1               5                   10

<210> SEQ ID NO 138
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 138

Gln Phe Cys Phe Asn Cys Gly Glu Asn Trp His Asp Pro Val Lys Cys
1               5                   10                  15

Lys
```

<210> SEQ ID NO 139
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 139

His Leu Trp Asn Val Asp Val Gln Gly Ser Lys Ala Tyr Ser Arg
1               5                   10                  15

<210> SEQ ID NO 140
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 140

Glu Gly Ala Lys Tyr Val Ser His Gly Ala Thr Gly Lys
1               5                   10

<210> SEQ ID NO 141
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 141

Tyr Val Ser His Gly Ala Thr Gly Lys Gly Asn Asp Gln Val Arg
1               5                   10                  15

<210> SEQ ID NO 142
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 142

His Cys Ile Gln Lys Ser Gln Glu Arg Val Glu Gly Lys
1               5                   10

<210> SEQ ID NO 143
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 143

His Cys Ile Gln Lys Ser Gln Glu Arg
1               5

<210> SEQ ID NO 144
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 144

Lys Val Glu Leu Trp Lys Glu Gln Phe Phe Glu Asn Tyr Tyr Gly Gln
1               5                   10                  15

Ser Ser Gly Leu Ser Leu Glu Asp Ser Gln Lys 20                  25

<210> SEQ ID NO 145
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 145

Val Gln Gln Leu Val Ala Lys Glu Leu Gly Gln Ile Gly Thr Arg
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 146

Glu His Ile Ala Ala Ser Val Ser Ile Pro Ser Glu Lys Gln Arg
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 147

Thr His Gly Arg Ala Lys Ser Tyr Lys Cys Gly Glu Cys Gly Lys
1               5                   10                  15

<210> SEQ ID NO 148
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 148

Leu Ile Val Asn Lys Asn Ala Gly Glu Thr Leu Leu Gln Arg
1               5                   10

<210> SEQ ID NO 149
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 149

Trp Asp Ile Gln Lys Tyr Ala Arg
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 150

Leu Val Ala Ser Lys Thr Asp Gly Lys
1               5

<210> SEQ ID NO 151
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 151

Gly Ser Ser Leu Pro Gly Lys Pro Ser Ser Pro His Ser Gly Gln Asp
1               5                   10                  15

Pro Pro Ala Pro Pro Val Asp
            20

<210> SEQ ID NO 152
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 152

Asp Ile Lys His Asp Pro Ser Leu Gln Pro Trp Ser Ala Ser Tyr Asp
1               5                   10                  15

Pro Gly Ser Ala Lys
            20

<210> SEQ ID NO 153
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 153

Asp Ile Lys His Asp Pro Ser Leu Gln Pro Trp Ser Ala Ser Tyr Asp
1               5                   10                  15

Pro Gly Ser Ala Lys Thr Ile Leu Asn Asn Gly Lys
            20                  25

<210> SEQ ID NO 154
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 154

Thr Asp Gln Gly Ile Lys Asn Leu Pro Val Gly Glu Ala Gly Arg
1               5                   10                  15

<210> SEQ ID NO 155
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 155

Phe Leu Ser Asp Lys Trp Met Leu Gln Lys
1               5                   10

<210> SEQ ID NO 156
<211> LENGTH: 8
<212> TYPE: PRT

```
<213> ORGANISM: Artificial Sequence
<220> FEATURE:
<223> OTHER INFORMATION: Synthetic Peptide

<400> SEQUENCE: 156

Leu Ala Cys Lys Glu Ala Val Arg
1               5

<210> SEQ ID NO 157
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 157

Asp Asp Lys His Gly Ser Tyr Glu Asn Ala Val His Ser Gly Ala Leu
1               5                   10                  15

Asp Asp

<210> SEQ ID NO 158
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 158

Val Asp Gln Ile Ile Met Ala Lys Pro Ala Gly Gly Pro Lys Pro Pro
1               5                   10                  15

Ser Gly Lys Lys Asp Trp Asp Asp Asp Gln Asn Asp
            20                  25

<210> SEQ ID NO 159
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 159

Pro Ala Gly Gly Pro Lys Pro Pro Ser Gly Lys Lys Asp Trp Asp Asp
1               5                   10                  15

Asp Gln Asn Asp
            20

<210> SEQ ID NO 160
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 160

Val Asp Gln Ile Ile Met Ala Lys Pro Ala Gly Gly Pro Lys Pro Pro
1               5                   10                  15

Ser Gly Lys Lys Asp Trp Asp Asp Asp Gln Asn Asp
            20                  25

<210> SEQ ID NO 161
<211> LENGTH: 12
<212> TYPE: PRT
<213> ORGANISM: Artificial Sequence
<220> FEATURE:
<223> OTHER INFORMATION: Synthetic Peptide
```

<400> SEQUENCE: 161

Ser Ile Gln Lys Leu Leu Glu Trp Glu Asn Asn Arg
1               5                   10

<210> SEQ ID NO 162
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 162

Arg Thr Thr His Gly Phe Lys Met Ser Lys Ile Tyr Lys
1               5                   10

<210> SEQ ID NO 163
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 163

Ser Thr Gly Pro Gly Thr Gly Thr Gly Thr Ala Tyr Asp Arg Lys Asp
1               5                   10                  15

Tyr Val

<210> SEQ ID NO 164
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 164

Leu His Ile Val Lys Val Val Ala Lys
1               5

<210> SEQ ID NO 165
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 165

Ala His Ile Ala Gln Leu Cys Glu Lys Ala Gly Leu Leu Gln Arg
1               5                   10                  15

<210> SEQ ID NO 166
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 166

Ala Val Asn Tyr Phe Ser Lys Val Lys
1               5

<210> SEQ ID NO 167
<211> LENGTH: 12
<212> TYPE: PRT
<213> ORGANISM: Artificial Sequence
<220> FEATURE:

<223> OTHER INFORMATION: Synthetic Peptide

<400> SEQUENCE: 167

Val Lys Gln Leu Pro Leu Val Lys Pro Tyr Leu Arg
1               5                   10

<210> SEQ ID NO 168
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 168

Glu Pro Leu Phe Gly Ile Ser Thr Gly Asn Ile Ile Thr Gly Leu Ala
1               5                   10                  15

Ala Gly Ala Lys Ser Tyr Lys
            20

<210> SEQ ID NO 169
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 169

Ser Tyr Lys Met Ser Met Ala Asn Arg
1               5

<210> SEQ ID NO 170
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 170

Gln Leu Phe Ser Asp Lys Leu Asn Glu Ile Asn Glu Lys Ile Ala Pro
1               5                   10                  15

Ser Phe Ala Val Glu Ser Met Glu Asp Ala Leu Lys
            20                  25

<210> SEQ ID NO 171
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 171

Thr Ser Ala Cys Phe Glu Pro Ser Leu Asp Tyr Met Val Thr Lys Ile
1               5                   10                  15

Pro Arg

<210> SEQ ID NO 172
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 172

Ser Ile Phe Ser Ala Val Leu Asp Glu Leu Lys Val Ala Gln Ala Pro
1               5                   10                  15

Trp Lys

<210> SEQ ID NO 173
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 173

Glu Val Glu Met Asp Ala Val Gly Lys Glu Gly Arg
1               5                   10

<210> SEQ ID NO 174
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 174

Ser Phe Pro Phe Val Ser Lys Thr Leu Gly Val Asp Phe Ile Asp Val
1               5                   10                  15

Ala Thr Lys

<210> SEQ ID NO 175
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 175

Tyr Leu Glu Ser Val Arg Pro Leu Met Lys Glu Gly Asp Phe Gln Arg
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 176

Val Leu Ala Ala Cys Leu Thr Glu Lys Gly Ala Glu Gln Leu Arg
1               5                   10                  15

<210> SEQ ID NO 177
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 177

Leu Ser His Ser Ile Glu Lys Leu Trp Asp Gln Thr Ser Ser Glu Val
1               5                   10                  15

Lys Glu Val Tyr Asp Lys Asn Phe Leu Asp Ser Tyr Ile Lys
            20                  25                  30

<210> SEQ ID NO 178
<211> LENGTH: 27
<212> TYPE: PRT
<213> ORGANISM: Artificial Sequence
<220> FEATURE:

<223> OTHER INFORMATION: Synthetic Peptide

<400> SEQUENCE: 178

Ala Val Val Leu Pro Ile Ser Leu Ala Thr Thr Phe Lys Gln Asp Phe
1               5                   10                  15

Pro Gly Gln Ser Ser Gly Phe Glu Tyr Ser Arg
            20                  25

<210> SEQ ID NO 179
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 179

Asn Cys Leu Glu Lys Ala Val Ala Ala Leu Asp Gly Ala Lys
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 180

Met Ser Glu Asp Lys Pro Gln Asp Tyr Lys Lys
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 181

Met Ser Glu Asp Lys Pro Gln Asp Tyr Lys Lys
1               5                   10

<210> SEQ ID NO 182
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 182

Met Glu Ile Val Asp His Ala Leu His Ala Leu Thr Asp Glu Val Ile
1               5                   10                  15

Ile Pro His Ser Gly Trp Glu Arg Glu Pro Asn Glu Asp Cys Lys Pro
            20                  25                  30

Arg

<210> SEQ ID NO 183
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 183

Met Glu Ile Val Asp His Ala Leu His Ala Leu Thr Asp Glu Val Ile
1               5                   10                  15

```
Ile Pro His Ser Gly Trp Glu Arg Glu Pro Asn Glu Asp Cys Lys Pro
            20                  25                  30

Arg

<210> SEQ ID NO 184
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 184

Ser Ala Leu Arg Gln Glu Lys Ala Leu Ser Ala Ile Ala Glu Leu Leu
1               5                   10                  15

Thr Ser Glu His Glu Arg
            20

<210> SEQ ID NO 185
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 185

Leu Ser Pro Glu Tyr Lys Gln Asn Glu Ile Asn Lys
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 186

Ser Pro Gly Thr Gly Ala Gly Leu Ala Glu Lys Ser Asp Arg
1               5                   10

<210> SEQ ID NO 187
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 187

Arg Ser Pro Gly Thr Gly Ala Gly Leu Ala Glu Lys Ser Asp Arg
1               5                   10                  15

<210> SEQ ID NO 188
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 188

Tyr Glu Lys Glu Val His His Asp Ile Arg
1               5                   10

<210> SEQ ID NO 189
<211> LENGTH: 19
<212> TYPE: PRT
<213> ORGANISM: Artificial Sequence
```

```
<220> FEATURE:
<223> OTHER INFORMATION: Synthetic Peptide

<400> SEQUENCE: 189

Val Tyr Asp Leu Thr Lys Phe Leu Glu Glu His Pro Gly Gly Glu Glu
1               5                   10                  15

Val Leu Arg

<210> SEQ ID NO 190
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 190

Leu Trp Tyr Thr Val Asp Lys Ala Pro Asp Ala Trp Asp Tyr Ser Gln
1               5                   10                  15

Gly Phe Val Asn Glu Glu Met Ile Arg
            20                  25

<210> SEQ ID NO 191
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 191

Ile Gly Ser Thr Pro Val Val Leu Ser Gly Leu Asn Thr Ile Lys
1               5                   10                  15

Gln Ala Leu Val Arg
            20

<210> SEQ ID NO 192
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 192

Tyr Leu Pro Asn Pro Ala Leu Lys Arg
1               5

<210> SEQ ID NO 193
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 193

Thr Val Gln Glu His Tyr Gln Asp Phe Asn Lys Asn Ser Ile Gln Asp
1               5                   10                  15

Ile Thr Ser Ala Leu Phe Lys
            20

<210> SEQ ID NO 194
<211> LENGTH: 16
<212> TYPE: PRT
<213> ORGANISM: Artificial Sequence
<220> FEATURE:
<223> OTHER INFORMATION: Synthetic Peptide
```

```
<400> SEQUENCE: 194

His Ser Glu Asn Tyr Lys Asp Asn Gly Gly Leu Ile Pro Glu Glu Lys
1               5                   10                  15

<210> SEQ ID NO 195
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 195

Asp Thr Ser Leu Asn Gly Phe His Ile Pro Lys Glu Arg
1               5                   10

<210> SEQ ID NO 196
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 196

Asp Ser His Lys Leu Glu Asp Phe Met Ile Gln Lys Val Lys
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 197

Val Lys Gln Asn Gln Ser Thr Leu Asp Pro Asn Ser Pro Arg
1               5                   10

<210> SEQ ID NO 198
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 198

Leu Ser Gly Lys Leu Pro Pro Gly Pro Thr Pro Leu Pro Phe Val Gly
1               5                   10                  15

Asn Phe Leu Gln Leu Asn Thr Glu Gln Met Tyr Asn Ser Leu Met Lys
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 199

Leu Ser Gly Lys Leu Pro Pro Gly Pro Thr Pro Leu Pro Phe Val Gly
1               5                   10                  15

Asn Phe Leu Gln Leu Asn Thr Glu Gln Met Tyr Asn Ser Leu Met Lys
            20                  25                  30

<210> SEQ ID NO 200
<211> LENGTH: 32
```

```
<212> TYPE: PRT
<213> ORGANISM: Artificial Sequence
<220> FEATURE:
<223> OTHER INFORMATION: Synthetic Peptide

<400> SEQUENCE: 200

Leu Ser Gly Lys Leu Pro Pro Gly Pro Thr Pro Leu Pro Phe Val Gly
 1               5                  10                  15

Asn Phe Leu Gln Leu Asn Thr Glu Gln Met Tyr Asn Ser Leu Met Lys
            20                  25                  30

<210> SEQ ID NO 201
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 201

His Leu Pro Gly Pro Gln Gln Gln Ala Phe Lys Glu Leu Gln Gly Leu
 1               5                  10                  15

Glu Asp Phe Ile Thr Lys
            20

<210> SEQ ID NO 202
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 202

Asn Arg Gln Pro Lys Tyr Glu Asp Arg
 1               5

<210> SEQ ID NO 203
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 203

Met Lys Met Pro Tyr Thr Glu Ala Val Ile His Glu Ile Gln Arg
 1               5                  10                  15

<210> SEQ ID NO 204
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 204

Phe Phe Ser Asn Pro Lys Asp Phe Asn Pro Lys
 1               5                  10

<210> SEQ ID NO 205
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 205

Glu Leu Gln Gly Leu Glu Asp Phe Ile Thr Lys Lys
```

```
<210> SEQ ID NO 206
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 206

Thr Lys Met Pro Tyr Thr Asp Ala Val Ile His Glu Ile Gln Arg
1               5                   10                  15

<210> SEQ ID NO 207
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 207

Lys Ser Asp Tyr Phe Met Pro Phe Ser Thr Gly Lys Arg
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 208

Ser Asp Tyr Phe Met Pro Phe Ser Thr Gly Lys Arg
1               5                   10

<210> SEQ ID NO 209
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 209

Lys Pro Thr Val Val Leu His Gly Tyr Glu Ala Val Lys Glu Ala Leu
1               5                   10                  15

Val Asp His Gly Glu Glu Phe Ala Gly Arg
            20                  25

<210> SEQ ID NO 210
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 210

Gly Thr Thr Val Ile Thr Ser Leu Ser Ser Val Leu His Asp Ser Lys
1               5                   10                  15

Glu Phe Pro Asn Pro Glu Met Phe Asp Pro Gly His Phe Leu Asn Gly
            20                  25                  30

Asn Gly Asn Phe Lys
        35

<210> SEQ ID NO 211
<211> LENGTH: 37
```

```
<212> TYPE: PRT
<213> ORGANISM: Artificial Sequence
<220> FEATURE:
<223> OTHER INFORMATION: Synthetic Peptide

<400> SEQUENCE: 211

Gly Thr Thr Val Val Thr Ser Leu Thr Ser Val Leu His Asp Ser Lys
1               5                   10                  15

Glu Phe Pro Asn Pro Glu Leu Phe Asp Pro Gly His Phe Leu Asp Ala
            20                  25                  30

Asn Gly Asn Phe Lys
        35

<210> SEQ ID NO 212
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 212

Asp Phe Ile Asp Tyr Tyr Leu Ile Lys Gln Lys
1               5                   10

<210> SEQ ID NO 213
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 213

Tyr Ile Asp Leu Gly Pro Asn Gly Val Val His Glu Val Thr Cys Asp
1               5                   10                  15

Thr Lys Phe Arg
            20

<210> SEQ ID NO 214
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 214

Gly Lys Gly Ile Gly Phe Ser His Gly Asn Val Trp Lys
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 215

Val Gln Glu Glu Ala Gln Trp Leu Met Lys Glu Leu Lys Lys
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Synthetic Peptide
```

```
<400> SEQUENCE: 216

Val Gln Glu Glu Ala Gln Trp Leu Met Lys Glu Leu Lys Lys
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 217

Val Gln Glu Glu Ala Gln Trp Leu Met Lys Glu Leu Lys
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 218

Val Gln Glu Glu Ala Gln Trp Leu Met Lys Glu Leu Lys
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 219

Val Gln Glu Glu Ala Gln Trp Leu Met Lys Glu Leu Lys
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 220

Val Gln Glu Glu Ala Gln Trp Leu Met Lys Glu Leu Lys Lys
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 221

Ile Lys Glu His Glu Glu Ser Leu Asp Val Thr Asn Pro Arg
1               5                   10

<210> SEQ ID NO 222
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 222
```

```
Lys Pro Thr Val Val Leu His Gly Tyr Glu Ala Val Lys Glu Ala Leu
1               5                   10                  15

Val Asp His Gly Asp Val Phe Ala Gly Arg
            20                  25
```

<210> SEQ ID NO 223
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 223

```
Phe Leu Lys Asp Val Thr Gln Gln Lys
1               5
```

<210> SEQ ID NO 224
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 224

```
Phe Leu Lys Asp Val Thr Gln Gln Lys Lys
1               5                   10
```

<210> SEQ ID NO 225
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 225

```
His Gln Lys Ser Leu Asp Leu Ser Asn Pro Gln Asp Phe Ile Asp Tyr
1               5                   10                  15

Phe Leu Ile Lys
            20
```

<210> SEQ ID NO 226
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 226

```
Gly Ser Ile Leu Ile Pro Asn Met Ser Ser Val Leu Lys Asp Glu Thr
1               5                   10                  15

Val Trp Glu Lys Pro Leu Arg
            20
```

<210> SEQ ID NO 227
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 227

```
Gly Thr Thr Leu Ile Pro Asn Leu Ser Ser Val Leu Lys Asp Glu Thr
1               5                   10                  15

Val Trp Glu Lys Pro Leu Arg
```

20

<210> SEQ ID NO 228
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 228

Gly Thr Thr Leu Ile Cys Asn Leu Ser Ser Val Leu Lys Asp Glu Thr
1               5                   10                  15

Val Trp Glu Lys Pro Leu Arg
            20

<210> SEQ ID NO 229
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 229

Ser Leu Thr Lys Leu Ala Lys
1               5

<210> SEQ ID NO 230
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 230

Ile Val Val Leu His Gly Tyr Lys Ala Val Lys
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 231

Arg Ile Val Val Leu His Gly Tyr Lys Ala Val Lys
1               5                   10

<210> SEQ ID NO 232
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 232

Ala Val Lys Glu Val Leu Leu Asn His Lys Asn Glu Phe Ser Gly Arg
1               5                   10                  15

<210> SEQ ID NO 233
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 233

```
Glu Val Leu Leu Asn His Lys Asn Glu Phe Ser Gly Arg
1               5                   10
```

<210> SEQ ID NO 234
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 234

```
Gly Asp Ile Pro Val Phe Gln Glu Tyr Lys Asn Lys
1               5                   10
```

<210> SEQ ID NO 235
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 235

```
Asn Lys Gly Ile Ile Phe Asn Asn Gly Pro Thr Trp Lys
1               5                   10
```

<210> SEQ ID NO 236
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 236

```
Gly Ile Ile Phe Asn Asn Gly Pro Thr Trp Lys Asp Val Arg
1               5                   10
```

<210> SEQ ID NO 237
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 237

```
Asp Trp Gly Met Gly Lys Gln Gly Asn Glu Ala Arg
1               5                   10
```

<210> SEQ ID NO 238
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 238

```
Asp Trp Gly Met Gly Lys Gln Gly Asn Glu Ala Arg
1               5                   10
```

<210> SEQ ID NO 239
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 239

Glu Ala His Phe Leu Val Glu Glu Leu Lys Lys
1               5                   10

<210> SEQ ID NO 240
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 240

Thr Lys Gly Gln Pro Phe Asp Pro Thr Phe Leu Ile Gly Cys Ala Pro
1               5                   10                  15

Cys Asn Val Ile Ala Asp Ile Leu Phe Asn Lys
            20                  25

<210> SEQ ID NO 241
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 241

Ala Lys Glu His Leu Lys Ser Leu Asp Ile Asn Cys Pro Arg
1               5                   10

<210> SEQ ID NO 242
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 242

Glu His Leu Lys Ser Leu Asp Ile Asn Cys Pro Arg
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 243

Asp Val Thr Asp Cys Leu Leu Ile Glu Met Glu Lys Glu Lys
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 244

Tyr Ser Asp Tyr Phe Lys Ala Phe Ser Ala Gly Lys
1               5                   10

<210> SEQ ID NO 245
<211> LENGTH: 13
<212> TYPE: PRT
<213> ORGANISM: Artificial Sequence
<220> FEATURE:
<223> OTHER INFORMATION: Synthetic Peptide

```
<400> SEQUENCE: 245

Tyr Ser Asp Tyr Phe Lys Ala Phe Ser Ala Gly Lys Arg
1               5                   10

<210> SEQ ID NO 246
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 246

Ser Leu Val Asp Pro Lys Asp Ile Asp Leu Ser Pro Val Thr Ile Gly
1               5                   10                  15

Phe Gly Ser Ile Pro Arg
            20

<210> SEQ ID NO 247
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 247

Lys Gln Gly Ile Pro Gly Pro Thr Pro Leu Pro Phe Leu Gly Thr Val
1               5                   10                  15

Leu Asn Tyr Tyr Lys
            20

<210> SEQ ID NO 248
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 248

Phe Cys Lys Lys Asp Val Glu Leu Asn Gly Val Tyr Ile Pro Lys
1               5                   10                  15

<210> SEQ ID NO 249
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 249

Glu Asn Lys Gly Ser Ile Asp Pro Tyr Leu Tyr Met Pro Phe Gly Ile
1               5                   10                  15

Gly Pro Arg

<210> SEQ ID NO 250
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 250

Glu Asn Lys Gly Ser Ile Asp Pro Tyr Leu Tyr Met Pro Phe Gly Ile
1               5                   10                  15

Gly Pro Arg
```

<210> SEQ ID NO 251
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 251

Phe Ser Lys Glu Asn Lys Gly Ser Ile Asp Pro Tyr Leu Tyr Met Pro
1               5                   10                  15

Phe Gly Ile Gly Pro Arg
            20

<210> SEQ ID NO 252
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 252

Val Met Gln Asn Phe Ser Phe Gln Pro Cys Gln Glu Thr Gln Ile Pro
1               5                   10                  15

Leu Lys Leu Ser Arg
            20

<210> SEQ ID NO 253
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 253

Phe Ser Lys Glu Asn Lys
1               5

<210> SEQ ID NO 254
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 254

Phe Ser Lys Glu Asn Lys Gly Ser Ile Asp Pro Tyr Val Tyr Leu Pro
1               5                   10                  15

Phe Gly Ile Gly Pro Arg
            20

<210> SEQ ID NO 255
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 255

Gln Gly Ile Leu Gln Pro Glu Lys Pro Ile Val Leu Lys
1               5                   10

<210> SEQ ID NO 256
<211> LENGTH: 17
<212> TYPE: PRT

```
<213> ORGANISM: Artificial Sequence
<220> FEATURE:
<223> OTHER INFORMATION: Synthetic Peptide

<400> SEQUENCE: 256

Gln Gly Ile Leu Gln Pro Glu Lys Pro Ile Val Leu Lys Val Val Pro
1               5                   10                  15

Arg

<210> SEQ ID NO 257
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 257

Glu Phe Gly Pro Val Gly Ile Met Ser Lys Ala Ile Ser Ile Ser Lys
1               5                   10                  15

Asp Glu Glu Trp Lys Arg
            20

<210> SEQ ID NO 258
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 258

Asn Val Leu Val Lys Glu Cys Phe Ser Val Phe Thr Asn Arg Arg
1               5                   10                  15

<210> SEQ ID NO 259
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 259

Ala Leu Leu Ser Pro Thr Phe Thr Ser Gly Lys Leu Lys
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 260

Gln Gly Leu Leu Gln Pro Glu Lys Pro Ile Val Leu Lys
1               5                   10

<210> SEQ ID NO 261
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 261

Lys Gln Gly Ile Pro Gly Pro Lys Pro Leu Pro Phe Leu Gly Thr Val
1               5                   10                  15
```

```
Leu Asn Tyr Tyr Lys
        20

<210> SEQ ID NO 262
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 262

Gln Gly Ile Pro Gly Pro Lys Pro Leu Pro Phe Leu Gly Thr Val Leu
1               5                   10                  15

Asn Tyr Tyr Lys
        20

<210> SEQ ID NO 263
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 263

Asn Val Leu Val Lys Glu Cys Phe Ser Val Phe Thr Asn Arg
1               5                   10

<210> SEQ ID NO 264
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 264

Leu Lys Glu Met Phe Pro Val Ile Glu Gln Tyr Gly Asp Ile Leu Val
1               5                   10                  15

Lys Tyr Leu Arg
        20

<210> SEQ ID NO 265
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 265

Glu Met Phe Pro Val Ile Glu Gln Tyr Gly Asp Ile Leu Val Lys Tyr
1               5                   10                  15

Leu Arg

<210> SEQ ID NO 266
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 266

Leu Lys Glu Met Phe Pro Val Ile Glu Gln Tyr Gly Asp Ile Leu Val
1               5                   10                  15

Lys Tyr Leu Arg
        20
```

```
<210> SEQ ID NO 267
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 267

Leu Lys Glu Met Phe Pro Val Ile Glu Gln Tyr Gly Asp Ile Leu Val
1               5                   10                  15

Lys

<210> SEQ ID NO 268
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 268

Leu Lys Glu Met Phe Pro Val Ile Glu Gln Tyr Gly Asp Ile Leu Val
1               5                   10                  15

Lys

<210> SEQ ID NO 269
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 269

Asp Ser Ile Glu Phe Phe Lys Lys
1               5

<210> SEQ ID NO 270
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 270

Gly Leu Trp Lys Phe Asp Met Glu Cys Tyr Glu Lys
1               5                   10

<210> SEQ ID NO 271
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 271

Leu Ala Lys Gln Ala Cys Gln Leu Ala His Asp His Thr Asp Gly Val
1               5                   10                  15

Ile Lys

<210> SEQ ID NO 272
<211> LENGTH: 21
<212> TYPE: PRT
<213> ORGANISM: Artificial Sequence
<220> FEATURE:
<223> OTHER INFORMATION: Synthetic Peptide
```

```
<400> SEQUENCE: 272

Tyr Leu Gln Asp Asn Pro Ala Ser Gly Glu Lys Phe Ala Tyr Val Pro
1               5                   10                  15

Phe Gly Ala Gly Arg
            20

<210> SEQ ID NO 273
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 273

Leu Asp Phe Asn Pro Asp Arg Tyr Leu Gln Asp Asn Pro Ala Ser Gly
1               5                   10                  15

Glu Lys Phe Ala Tyr Val Pro Phe Gly Ala Gly Arg
            20                  25

<210> SEQ ID NO 274
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 274

Ser Ile Asp Pro Ser Asp Gly Asn Thr Thr Glu Asn Ile Asn Lys Thr
1               5                   10                  15

Phe Asn Lys

<210> SEQ ID NO 275
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 275

Val Val Gln Glu Asp Tyr Val Leu Lys Met Ala Ser Gly Gln Glu Tyr
1               5                   10                  15

Gln Ile Arg

<210> SEQ ID NO 276
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 276

Gln Ala Thr Val Gly Asp Val Asn Thr Asp Arg Pro Gly Leu Leu Asp
1               5                   10                  15

Leu Lys Gly Lys
            20

<210> SEQ ID NO 277
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 277
```

```
Gln Met Gly Gln Pro Cys Asp Ala Tyr Gln Lys Arg
1               5                   10
```

<210> SEQ ID NO 278
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 278

```
Ala Leu Tyr Lys Ala Ile Ser Val Pro Arg
1               5                   10
```

<210> SEQ ID NO 279
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 279

```
Trp Gln Leu Asp Lys Ile Lys
1               5
```

<210> SEQ ID NO 280
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 280

```
Val Lys His Phe Glu Ala Arg
1               5
```

<210> SEQ ID NO 281
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 281

```
Ser Gly Ala Val Gln Lys Cys Ser Ala Cys Arg
1               5                   10
```

<210> SEQ ID NO 282
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 282

```
Val Ala Glu Leu Met Gly Gln Lys Leu Pro Ser Phe Gly Pro Tyr Leu
1               5                   10                  15

Glu Gln Arg
```

<210> SEQ ID NO 283
<211> LENGTH: 15
<212> TYPE: PRT
<213> ORGANISM: Artificial Sequence
<220> FEATURE:
<223> OTHER INFORMATION: Synthetic Peptide

```
<400> SEQUENCE: 283

Leu Gly Asp Lys Val Gln Phe Cys His Thr Asp Asp Asn Gln Lys
1               5                   10                  15

<210> SEQ ID NO 284
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 284

Ile Ser Ile Gly Lys Lys
1               5

<210> SEQ ID NO 285
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 285

Tyr Phe Asp Pro Ala Asn Gly Lys Phe Ser Lys
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 286

Phe Ser Lys Ser Ala Asn Ser Pro Asp Gly Lys
1               5                   10

<210> SEQ ID NO 287
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 287

Thr Glu Pro Thr Ala Gln Gln Asn Leu Ala Leu Gln Leu Ala Glu Lys
1               5                   10                  15

Leu Gly Ser Leu Val Glu Asn Asn Glu Arg
            20                  25

<210> SEQ ID NO 288
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 288

Glu Gln Pro Glu Lys Glu Pro Glu Leu Gln Gln Tyr Val Pro Gln Leu
1               5                   10                  15

Gln Asn Asn Thr Ile Leu Arg
            20

<210> SEQ ID NO 289
<211> LENGTH: 14
```

-continued

```
<212> TYPE: PRT
<213> ORGANISM: Artificial Sequence
<220> FEATURE:
<223> OTHER INFORMATION: Synthetic Peptide

<400> SEQUENCE: 289

Gln Ser Val Tyr Glu Glu Lys Leu Lys Gln Phe Glu Glu Arg
1               5                   10

<210> SEQ ID NO 290
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 290

Glu Asn Met Tyr Ala Val Gln Thr Leu Lys Asp Phe Gln Tyr Val Asp
1               5                   10                  15

Arg Asp Gly Lys Asp Gln Gly Val Asn Val Arg
            20                  25

<210> SEQ ID NO 291
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 291

Cys Phe Gly Gly Leu Gln Lys Val Phe Glu His Ser Ser Val Glu Leu
1               5                   10                  15

Lys

<210> SEQ ID NO 292
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 292

Tyr Gln Leu Gln Ser Gln Glu Asn Phe Glu Pro Phe Met Lys Ala Ile
1               5                   10                  15

Gly Leu Pro Glu Asp Leu Ile Gln Lys
            20                  25

<210> SEQ ID NO 293
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 293

Ala Ile Gly Leu Pro Glu Asp Leu Ile Gln Lys Gly Lys
1               5                   10

<210> SEQ ID NO 294
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 294
```

```
Gly Lys Asp Ile Lys Gly Val Ser Glu Ile Val His Glu Gly Lys
1               5                   10                  15
```

<210> SEQ ID NO 295
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 295

```
Asp Ile Lys Gly Val Ser Glu Ile Val His Glu Gly Lys
1               5                   10
```

<210> SEQ ID NO 296
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 296

```
Gly Val Ser Glu Ile Val His Glu Gly Lys Lys
1               5                   10
```

<210> SEQ ID NO 297
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 297

```
Val Lys Ala Val Val Lys Leu Glu Gly Asp Asn Lys
1               5                   10
```

<210> SEQ ID NO 298
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 298

```
Ala Val Val Lys Leu Glu Gly Asp Asn Lys
1               5                   10
```

<210> SEQ ID NO 299
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 299

```
Met Val Thr Thr Phe Lys Gly Ile Lys
1               5
```

<210> SEQ ID NO 300
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 300

```
Trp Glu Glu Ile Gln Lys His Asn Leu Arg
1               5                   10

<210> SEQ ID NO 301
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 301

Phe Leu Lys Pro Leu Leu Ile Gly Glu Leu Ala Pro Glu Glu Pro Ser
1               5                   10                  15

Leu Asp Arg

<210> SEQ ID NO 302
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 302

Arg Pro Met Gly Gln Met Arg Pro Asp Asn Ser Lys Pro Pro Val Tyr
1               5                   10                  15

Gly Ala Cys Arg
            20

<210> SEQ ID NO 303
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 303

Ala Lys Ile Arg Gly Ser Tyr Leu Thr Val Thr Leu Gln Arg Pro Thr
1               5                   10                  15

Lys

<210> SEQ ID NO 304
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 304

Gln Ile Leu Glu Glu Asn Tyr Gly Gln Lys Asp Pro Glu Lys Val Ala
1               5                   10                  15

Arg

<210> SEQ ID NO 305
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 305

Gln Ile Leu Glu Glu Asn Tyr Gly Gln Lys Asp Pro Glu Lys Val Ala
1               5                   10                  15

Arg
```

<210> SEQ ID NO 306
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 306

```
Val Leu Val Ile Gly Leu Gly Asn Ser Gly Cys Asp Ile Ala Ala Glu
1               5                   10                  15

Leu Ser His Val Ala Gln Lys Val Thr Ile Ser Ser Arg
            20                  25
```

<210> SEQ ID NO 307
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 307

```
Asn Asn Tyr Met Glu Lys Gln Met Asn Gln Arg
1               5                   10
```

<210> SEQ ID NO 308
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 308

```
Ser Lys Ala Glu Glu Val Val Ser Phe Val Lys Lys Asn Val Leu Val
1               5                   10                  15

Thr Gly Gly Phe Phe Gly Gly Phe Leu Leu Gly Met Ala Ser
            20                  25                  30
```

<210> SEQ ID NO 309
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 309

```
Thr Phe Thr Thr Gln Glu Thr Ile Thr Asn Ala Glu Thr Ala Lys Glu
1               5                   10                  15

Trp Phe Leu Glu Ala Ala Lys Asp Pro Ser Ala Val Ala Lys
            20                  25                  30
```

<210> SEQ ID NO 310
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 310

```
Gly Ala Ala Gln Asn Ile Ile Pro Ala Ser Thr Gly Ala Ala Lys Ala
1               5                   10                  15

Val Gly Lys
```

<210> SEQ ID NO 311
<211> LENGTH: 12

```
<212> TYPE: PRT
<213> ORGANISM: Artificial Sequence
<220> FEATURE:
<223> OTHER INFORMATION: Synthetic Peptide

<400> SEQUENCE: 311

Leu Glu Lys Pro Ala Lys Tyr Asp Asp Ile Lys Lys
1               5                   10

<210> SEQ ID NO 312
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 312

Thr Leu Lys Asn Gly Thr Thr Thr Ala Cys Tyr Phe Gly Thr Ile His
1               5                   10                  15

Thr Asp Ser Ser Leu Ile Leu Ala Glu Ile Thr Asp Lys Phe Gly Gln
                20                  25                  30

Arg

<210> SEQ ID NO 313
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 313

Val Ser Lys Ala Ser Ala Asp Leu Met Ser Tyr Cys Glu Glu His Ala
1               5                   10                  15

Arg

<210> SEQ ID NO 314
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 314

Lys Asp Pro Asn Lys Leu Val Leu Cys Glu Val Phe Lys
1               5                   10

<210> SEQ ID NO 315
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 315

Tyr Ala Leu Lys Glu Arg
1               5

<210> SEQ ID NO 316
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 316
```

Val Leu Lys Ser His Gly Gln Asp Tyr Leu Val Gly Asn Arg
1               5                   10

<210> SEQ ID NO 317
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 317

Ser Asp Gly Ser Leu Met Phe Gln Gln Val Pro Met Val Glu Ile Asp
1               5                   10                  15

Gly Met Lys Leu Val Gln Thr Lys
            20

<210> SEQ ID NO 318
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 318

Ser Asp Gly Ser Leu Met Phe Gln Gln Val Pro Met Val Glu Ile Asp
1               5                   10                  15

Gly Met Lys Leu Val Gln Thr Lys
            20

<210> SEQ ID NO 319
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 319

Ser Asp Gly Ser Leu Met Phe Gln Gln Val Pro Met Val Glu Ile Asp
1               5                   10                  15

Gly Met Lys Leu Val Gln Thr Lys
            20

<210> SEQ ID NO 320
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 320

Ile Ser Ala Tyr Met Lys Ser Ser Arg
1               5

<210> SEQ ID NO 321
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 321

Phe Lys Leu Gly Leu Asp Phe Pro Asn Leu Pro Tyr Leu Ile Asp Gly
1               5                   10                  15

Ser His Lys

<210> SEQ ID NO 322
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 322

Leu Gly Leu Asp Phe Pro Asn Leu Pro Tyr Leu Ile Asp Gly Ser His
1               5                   10                  15

Lys Ile Thr Gln Ser Asn Ala Ile Leu Arg
            20                  25

<210> SEQ ID NO 323
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 323

Ala Leu Pro Gly His Leu Lys Pro Phe Glu Thr Leu Leu Ser Gln Asn
1               5                   10                  15

Gln Gly Gly Lys
            20

<210> SEQ ID NO 324
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 324

Ala Lys Asp Met Pro Pro Leu Met Asp Pro Ala Leu Lys
1               5                   10

<210> SEQ ID NO 325
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 325

Ala Met Leu Glu Ala His Pro Lys Val Val Ala His Tyr Pro Val Glu
1               5                   10                  15

Val Arg

<210> SEQ ID NO 326
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 326

Ala Met Leu Glu Ala His Pro Lys Val Val Ala His Tyr Pro Val Glu
1               5                   10                  15

Val Arg

<210> SEQ ID NO 327
<211> LENGTH: 14
<212> TYPE: PRT

```
<213> ORGANISM: Artificial Sequence
<220> FEATURE:
<223> OTHER INFORMATION: Synthetic Peptide

<400> SEQUENCE: 327

Ser His Tyr Lys Val Gly Glu Asn Ala Asp Ser Gln Ile Lys
1               5                   10

<210> SEQ ID NO 328
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 328

Val Thr Ile Ala Gln Gly Gly Val Leu Pro Asn Ile Gln Ala Val Leu
1               5                   10                  15

Leu Pro Lys Lys Thr Glu Ser His His Lys Pro Lys
            20                  25

<210> SEQ ID NO 329
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 329

Lys Ser Ser Ala Thr Val Gly Pro Lys Ala Pro Ala Val Gly Lys
1               5                   10                  15

<210> SEQ ID NO 330
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 330

Pro Glu Pro Ala Lys Ser Ala Pro Ala Pro Lys
1               5                   10

<210> SEQ ID NO 331
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 331

Ser Asn Ile Lys Ala Ala Trp Gly Lys
1               5

<210> SEQ ID NO 332
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 332

Ala Ala Trp Gly Lys Ile Gly Gly His Gly Ala Glu Tyr Gly Ala Glu
1               5                   10                  15

Ala Leu Glu Arg
            20
```

<210> SEQ ID NO 333
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 333

Met Phe Ala Ser Phe Pro Thr Thr Lys Thr Tyr Phe Pro His Phe Asp
1               5                   10                  15

Val Ser His Gly Ser Ala Gln Val Lys
            20                  25

<210> SEQ ID NO 334
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 334

Met Phe Ala Ser Phe Pro Thr Thr Lys Thr Tyr Phe Pro His Phe Asp
1               5                   10                  15

Val Ser His Gly Ser Ala Gln Val Lys
            20                  25

<210> SEQ ID NO 335
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 335

Thr Tyr Phe Pro His Phe Asp Val Ser His Gly Ser Ala Gln Val Lys
1               5                   10                  15

Gly His Gly Lys
            20

<210> SEQ ID NO 336
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 336

Val Ala Asp Ala Leu Ala Ser Ala Ala Gly His Leu Asp Asp Leu Pro
1               5                   10                  15

Gly Ala Leu Ser Ala Leu Ser Asp Leu His Ala His Lys Leu Arg
            20                  25                  30

<210> SEQ ID NO 337
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 337

Lys Val Ala Asp Ala Leu Ala Ser Ala Ala Gly His Leu Asp Asp Leu
1               5                   10                  15

Pro Gly Ala Leu Ser Ala Leu Ser Asp Leu His Ala His Lys Leu Arg

```
                20                  25                  30
```

<210> SEQ ID NO 338
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 338

```
Ser Ala Val Ser Cys Leu Trp Ala Lys Val Asn Pro Asp Glu Val Gly
1               5                   10                  15

Gly Glu Ala Leu Gly Arg
            20
```

<210> SEQ ID NO 339
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 339

```
Tyr Phe Asp Ser Phe Gly Asp Leu Ser Ser Ala Ser Ala Ile Met Gly
1               5                   10                  15

Asn Pro Lys Val Lys
            20
```

<210> SEQ ID NO 340
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 340

```
Asn Leu Asp Asn Leu Lys Gly Thr Phe Ala Ser Leu Ser Glu Leu His
1               5                   10                  15

Cys Asp Lys Leu His Val Asp Pro Glu Asn Phe Arg
            20                  25
```

<210> SEQ ID NO 341
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 341

```
Ala Ala Val Ser Cys Leu Trp Gly Lys Val Asn Ser Asp Glu Val Gly
1               5                   10                  15

Gly Glu Ala Leu Gly Arg
            20
```

<210> SEQ ID NO 342
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 342

```
Tyr Phe Asp Ser Phe Gly Asp Leu Ser Ser Ala Ser Ala Ile Met Gly
1               5                   10                  15
```

Asn Ala Lys Val Lys
        20

<210> SEQ ID NO 343
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 343

Val Ile Thr Ala Phe Asn Asp Gly Leu Asn His Leu Asp Ser Leu Lys
1               5                   10                  15

Gly Thr Phe Ala Ser Leu Ser Glu Leu His Cys Asp Lys Leu His Val
            20                  25                  30

Asp Pro Glu Asn Phe Arg
        35

<210> SEQ ID NO 344
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 344

Ile Leu Pro Ser Val Ser His Lys Pro Phe Glu Ser Ile Asp Gln Gly
1               5                   10                  15

His Val Thr His Asn Trp Asp Glu Val Gly Pro Asp Pro Asn Gln Leu
            20                  25                  30

Arg

<210> SEQ ID NO 345
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 345

Phe Gln Gly Lys Leu Phe Ala Cys Lys
1               5

<210> SEQ ID NO 346
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 346

Met Phe Val Gly Gly Leu Ser Trp Asp Thr Ser Lys Lys
1               5                   10

<210> SEQ ID NO 347
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 347

Met Phe Val Gly Gly Leu Ser Trp Asp Thr Ser Lys Lys
1               5                   10

```
<210> SEQ ID NO 348
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 348

Val Ala Gln Pro Lys Glu Val Tyr Gln Gln Gln Tyr Gly Ser Gly
1               5                   10                  15

Gly Arg

<210> SEQ ID NO 349
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 349

Glu Val Val Ser His Val Ile Lys Gln Gly Lys
1               5                   10

<210> SEQ ID NO 350
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 350

Ile Val Arg Glu Pro Trp Val Glu Gln Asp Lys Phe Gly Lys
1               5                   10

<210> SEQ ID NO 351
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 351

Ile Val Arg Glu Pro Trp Val Glu Gln Asp Lys Phe Gly Lys Val Lys
1               5                   10                  15

<210> SEQ ID NO 352
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 352

Val Lys Phe Ala Val Leu Gln Thr Tyr Gly Asp Thr Thr His Thr Leu
1               5                   10                  15

Val Glu Lys

<210> SEQ ID NO 353
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 353
```

Ile Val Arg Glu Pro Trp Val Glu Gln Asp Lys Phe Gly Lys Val Lys
1               5                   10                  15

<210> SEQ ID NO 354
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 354

Ser Ile Val Val Thr Asn Tyr Glu Glu Ser Ile Lys Met Pro Ile Asn
1               5                   10                  15

Glu Pro Ala Pro Gly Arg
            20

<210> SEQ ID NO 355
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 355

Lys Lys Ser Gln Ile Gln Glu Tyr Val Asp Tyr Asn Gly Gly Ala Gly
1               5                   10                  15

Val Gln His Ile Ala Leu Lys
            20

<210> SEQ ID NO 356
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 356

Lys Lys Ser Gln Ile Gln Glu Tyr Val Asp Tyr Asn Gly Gly Ala Gly
1               5                   10                  15

Val Gln His Ile Ala Leu Lys
            20

<210> SEQ ID NO 357
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 357

Ser Gln Ile Gln Glu Tyr Val Asp Tyr Asn Gly Gly Ala Gly Val Gln
1               5                   10                  15

His Ile Ala Leu Lys Thr Glu Asp Ile Ile Thr Ala Ile Arg
            20                  25                  30

<210> SEQ ID NO 358
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 358

Glu Arg Gly Thr Glu Phe Leu Ala Ala Pro Ser Ser Tyr Tyr Lys Leu
1               5                   10                  15

Leu Arg

<210> SEQ ID NO 359
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 359

His Asn His Gln Gly Phe Gly Ala Gly Asn Phe Asn Ser Leu Phe Lys
1               5                   10                  15

Ala Phe Glu Glu Glu Gln Ala Leu Arg
            20                  25

<210> SEQ ID NO 360
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 360

Asn Leu Gly Glu Ile Leu Lys Ala Ala Gly Cys Asp Phe Asn Asn Val
1               5                   10                  15

Val Lys

<210> SEQ ID NO 361
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 361

Val Gln Val Glu Tyr Lys Gly Glu Thr Lys
1               5                   10

<210> SEQ ID NO 362
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 362

Leu Ser Lys Glu Asp Ile Glu Arg
1               5

<210> SEQ ID NO 363
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 363

Met Val Gln Glu Ala Glu Lys Tyr Lys Ala Glu Asp Glu Lys
1               5                   10

<210> SEQ ID NO 364
<211> LENGTH: 16
<212> TYPE: PRT
<213> ORGANISM: Artificial Sequence
<220> FEATURE:

<223> OTHER INFORMATION: Synthetic Peptide

<400> SEQUENCE: 364

Met Val Gln Glu Ala Glu Lys Tyr Lys Ala Glu Asp Glu Lys Gln Arg
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 365

Met Val Gln Glu Ala Glu Lys Tyr Lys Ala Glu Asp Glu Lys Gln Arg
1               5                   10                  15

<210> SEQ ID NO 366
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 366

Ile Leu Asp Lys Cys Asn Glu Ile Ile Ser Trp Leu Asp Lys Asn Gln
1               5                   10                  15

Thr Ala Glu Lys Glu Glu Phe Glu His Gln Gln Lys
            20                  25

<210> SEQ ID NO 367
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 367

Ile Leu Asp Lys Cys Asn Glu Ile Ile Ser Trp Leu Asp Lys Asn Gln
1               5                   10                  15

Thr Ala Glu Lys Glu Glu Phe Glu His Gln Gln Lys Glu Leu Glu Lys
            20                  25                  30

<210> SEQ ID NO 368
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 368

Ile Pro Lys Ile Gln Lys
1               5

<210> SEQ ID NO 369
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 369

Ser Glu Glu Gly Leu Gln Lys Val Val Ser Arg
1               5                   10

```
<210> SEQ ID NO 370
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 370

Ile Lys Glu Glu Tyr Glu Val Ala Glu Met Gly Ala Pro His Gly Ser
1               5                   10                  15

Ala Ser Val Arg
            20

<210> SEQ ID NO 371
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 371

Ile Lys Glu Glu Tyr Glu Val Ala Glu Met Gly Ala Pro His Gly Ser
1               5                   10                  15

Ala Ser Val Arg
            20

<210> SEQ ID NO 372
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 372

Lys Lys Thr Ser Glu Glu Ile Leu Gln His Leu Gln Asn Ile Val Asp
1               5                   10                  15

Phe Gly Lys Asn Val Met Lys
            20

<210> SEQ ID NO 373
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 373

Ala Trp Val Asn Gln Leu Glu Thr Gln Thr Gly Glu Ala Ser Lys Leu
1               5                   10                  15

Pro Tyr Asp Val Thr Thr Glu Gln Ala Leu Thr Tyr Pro Glu Val Lys
            20                  25                  30

<210> SEQ ID NO 374
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 374

Thr Pro Glu Glu Gly Lys Gln Ser Gln Ala Val Ile Glu Asp Ala Arg
1               5                   10                  15

<210> SEQ ID NO 375
<211> LENGTH: 10
```

```
<212> TYPE: PRT
<213> ORGANISM: Artificial Sequence
<220> FEATURE:
<223> OTHER INFORMATION: Synthetic Peptide

<400> SEQUENCE: 375

Asn Ile Glu Val Pro Phe Lys Pro Ala Arg
1               5                   10

<210> SEQ ID NO 376
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 376

Val Ser Thr Asn Gly Ser Glu Asp Pro Glu Val Ala Ala Ser Gly Glu
1               5                   10                  15

Asn Lys Arg

<210> SEQ ID NO 377
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 377

Phe Ile Tyr Gly Asn Gln Asp Leu Phe Ala Thr Ser Gln Asn Lys Glu
1               5                   10                  15

Phe Asp Pro Leu Gly Pro Leu Pro Pro Gly Trp Glu Lys Arg
            20                  25                  30

<210> SEQ ID NO 378
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 378

Val Thr Phe Asn Ser Ala Leu Ala Gln Lys Glu Ala Lys
1               5                   10

<210> SEQ ID NO 379
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 379

Gly Lys Asn Cys Glu Leu Leu Leu Val Val Pro Glu Glu Val Glu Ala
1               5                   10                  15

His Gln Ser Trp Arg
            20

<210> SEQ ID NO 380
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 380
```

```
Ile Glu Glu His Asn Ala Lys Gln Pro Leu Pro Gln Lys
1               5                   10
```

<210> SEQ ID NO 381
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 381

```
Ala Val Ala Lys Gln Gln Asn Val Gln Ser Thr Ser Gln Asp Glu Lys
1               5                   10                  15
```

<210> SEQ ID NO 382
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 382

```
Thr Tyr Ser Ala Lys Leu Asp Asn Ala Arg
1               5                   10
```

<210> SEQ ID NO 383
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 383

```
Lys Glu Ser Asp Leu Ser Gly Ala Gln Ile Lys Leu Arg
1               5                   10
```

<210> SEQ ID NO 384
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 384

```
Ile Pro Glu Lys Glu Pro Pro Pro Tyr Leu Pro Ala
1               5                   10
```

<210> SEQ ID NO 385
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 385

```
Val Ile Asp Leu Val Asn Lys Glu Asp Val Gln Ile Ser Thr Thr Gln
1               5                   10                  15

Val Ala Glu Ile Val Ala Thr Leu Glu Lys Glu Glu Lys
            20                  25
```

<210> SEQ ID NO 386
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 386

Leu Leu Glu Glu Ala Leu Lys Lys
1               5

<210> SEQ ID NO 387
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 387

Met Gln Ala Asn Asn Ala Lys Ala Val Ser Ala Arg Thr Glu Ala Ile
1               5                   10                  15

Lys Ala Leu Val Lys
            20

<210> SEQ ID NO 388
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 388

Ser Tyr Leu Leu Glu Lys Ile Lys Glu His Glu Glu Ser Leu Asp Val
1               5                   10                  15

Thr Asn Pro Arg
            20

<210> SEQ ID NO 389
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 389

Lys His Met Pro Tyr Thr Asn Ala Met Val His Glu Val Gln Arg
1               5                   10                  15

<210> SEQ ID NO 390
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 390

Tyr Val Asp Leu Gly Pro Thr Ser Leu Val His Glu Val Thr Cys Asp
1               5                   10                  15

Thr Lys Phe Arg
            20

<210> SEQ ID NO 391
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 391

Asp Gln Pro Gln His Leu Glu Lys Ile Thr Cys Gln Gln Arg
1               5                   10

<210> SEQ ID NO 392
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 392

Thr Leu Leu Lys Glu Ile Cys Leu Arg Asn
1               5                   10

<210> SEQ ID NO 393
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 393

Thr Ala Ala Lys Gly Glu Ala Thr Ala Glu Arg Pro Gly Glu Ala Ala
1               5                   10                  15

Val Ala Ser Ser Pro Ser Lys
            20

<210> SEQ ID NO 394
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 394

Gln Asp Pro Asn Ala Lys Val Ala Cys Glu Thr Val Cys Lys
1               5                   10

<210> SEQ ID NO 395
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 395

Asp Thr Ile Lys His Ile Gly Tyr Asp Asp Ser Ala Lys
1               5                   10

<210> SEQ ID NO 396
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 396

His Ile Gly Tyr Asp Asp Ser Ala Lys Gly Phe Asp Phe Lys
1               5                   10

<210> SEQ ID NO 397
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 397

```
Glu Leu Leu Glu Val Val Asn Lys Asn Phe Asp Leu Arg Pro Gly Val
1               5                   10                  15

Ile Val Arg

<210> SEQ ID NO 398
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 398

Asp Leu Asp Leu Lys Lys Pro Ile Tyr Gln Lys
1               5                   10

<210> SEQ ID NO 399
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 399

Lys Pro Ile Tyr Gln Lys Thr Ala Cys Tyr Gly His Phe Gly Arg
1               5                   10                  15

<210> SEQ ID NO 400
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 400

Asp Leu Asp Leu Lys Lys Pro Ile Tyr Gln Lys Thr Ala Cys Tyr Gly
1               5                   10                  15

His Phe Gly Arg
            20

<210> SEQ ID NO 401
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 401

Ser Asp Val Tyr Tyr Phe Ser Pro Ser Gly Lys Lys Phe Arg Ser Lys
1               5                   10                  15

<210> SEQ ID NO 402
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 402

Glu Gly Lys Glu Asp Glu Ala Ser Thr Asp Val Asp Glu Lys Pro Lys
1               5                   10                  15

Glu Thr Met Lys
            20

<210> SEQ ID NO 403
<211> LENGTH: 20
```

```
<212> TYPE: PRT
<213> ORGANISM: Artificial Sequence
<220> FEATURE:
<223> OTHER INFORMATION: Synthetic Peptide

<400> SEQUENCE: 403

Glu Gly Lys Glu Asp Glu Ala Ser Thr Asp Val Asp Glu Lys Pro Lys
1               5                   10                  15

Glu Thr Met Lys
            20

<210> SEQ ID NO 404
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 404

Trp Leu Pro Val Gly Pro His Ile Met Gly Lys Ala Val Lys
1               5                   10

<210> SEQ ID NO 405
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 405

Trp Leu Pro Val Gly Pro His Ile Met Gly Lys Ala Val Lys
1               5                   10

<210> SEQ ID NO 406
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 406

Val Phe Ala Asn Pro Glu Asp Cys Ala Gly Phe Gly Lys Gly Glu Asn
1               5                   10                  15

Ala Lys Lys

<210> SEQ ID NO 407
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 407

Val Phe Ala Asn Pro Glu Asp Cys Ala Gly Phe Gly Lys Gly Glu Asn
1               5                   10                  15

Ala Lys Lys

<210> SEQ ID NO 408
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 408
```

Glu Leu Gln Lys Ala Asn Gln Glu Gln Tyr Ala Glu Gly Lys
1               5                   10

<210> SEQ ID NO 409
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 409

Leu Cys Asp Pro Ser Glu Gln Ala Leu Tyr Gly Lys Leu Pro Ile Phe
1               5                   10                  15

Gly Gln Tyr Phe Ala Leu Glu Asn Pro Gly Thr Ile Arg
            20                  25

<210> SEQ ID NO 410
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 410

Asp Tyr His Phe Val Ser Arg Gln Ala Phe Glu Ala Asp Ile Ala Ala
1               5                   10                  15

Gly Lys Phe Ile Glu His Gly Leu Phe Glu Lys Asn Leu Tyr Gly Thr
            20                  25                  30

Ser Ile Asp Ser Val Arg
        35

<210> SEQ ID NO 411
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 411

Met Asp Pro Asn Cys Ser Cys Ala Ser Asp Gly Ser Cys Ser Cys Ala
1               5                   10                  15

Gly Ala Cys Lys Cys Lys
            20

<210> SEQ ID NO 412
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 412

Ile His Lys Thr Ser Asn Pro Trp Gln Ser Pro Ser Gly Thr Leu Pro
1               5                   10                  15

Ala Leu Arg

<210> SEQ ID NO 413
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 413

```
Gln Met Asn Asp Glu Lys Thr Ala Ala Asp Tyr Lys
1               5                   10
```

<210> SEQ ID NO 414
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 414

```
Lys Val Gln Phe Ser Gln His Pro Ala Ala Ala Lys Leu Pro Leu Glu
1               5                   10                  15

Gln Ser Glu Asp Pro Ala Gly Leu Ile Arg
            20                  25
```

<210> SEQ ID NO 415
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 415

```
Val Gln Phe Ser Gln His Pro Ala Ala Ala Lys Leu Pro Leu Glu Gln
1               5                   10                  15

Ser Glu Asp Pro Ala Gly Leu Ile Arg
            20                  25
```

<210> SEQ ID NO 416
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 416

```
Gln Gly Gly Leu Gly Pro Met Asn Ile Pro Leu Ile Ser Asp Pro Lys
1               5                   10                  15

Arg
```

<210> SEQ ID NO 417
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 417

```
Gln His Tyr Ile Asp Leu Lys Asp Arg Pro Phe Phe Pro Gly Leu Val
1               5                   10                  15

Lys
```

<210> SEQ ID NO 418
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 418

```
Ala Glu Ser Lys Ala Pro Ala Gly Gly Gln Asn Asn Pro Ser Ser Ser
1               5                   10                  15

Pro Ser Gly Ser Thr Val Ser Gln Ala Ser Lys
```

```
                     20                  25

<210> SEQ ID NO 419
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 419

Ser Phe Asn Gly Ser Leu Lys Lys
1               5

<210> SEQ ID NO 420
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 420

Gly Ala Lys Glu His Gly Ala Val Ala Val Glu Arg
1               5                   10

<210> SEQ ID NO 421
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 421

Ser Thr Gln Thr Ala Pro Ser Ala Pro Ser Thr Gly Gln Lys Ser
1               5                   10                  15

Pro Arg Val Asn Pro Pro Val Pro Lys Ser Gly Ser Ser Gln Ala Lys
            20                  25                  30

Ala Leu Gln Pro Pro Val Thr Glu Lys
        35                  40

<210> SEQ ID NO 422
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 422

Glu Pro Lys Glu Leu Lys Leu Ser Val Pro Met Pro Tyr Met Leu Lys
1               5                   10                  15

<210> SEQ ID NO 423
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 423

Lys Phe Glu Gln Met Lys Gln Asp Arg
1               5

<210> SEQ ID NO 424
<211> LENGTH: 11
<212> TYPE: PRT
<213> ORGANISM: Artificial Sequence
<220> FEATURE:
```

<223> OTHER INFORMATION: Synthetic Peptide

<400> SEQUENCE: 424

Glu Glu Val Gly Ala Leu Ala Lys Val Leu Arg
1               5                   10

<210> SEQ ID NO 425
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 425

Ser Lys Pro Val Leu Gly Ser Ile Ile Lys Ser Leu Arg
1               5                   10

<210> SEQ ID NO 426
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 426

Thr Ile Gln Glu Leu Asp Arg Phe Ala Asn Gln Ile Leu Ser Tyr Gly
1               5                   10                  15

Ala Glu Leu Asp Ala Asp His Pro Gly Phe Lys Asp Pro Val Tyr Arg
            20                  25                  30

<210> SEQ ID NO 427
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 427

Ala Gly Glu Ile Lys Gly Phe Thr Gly Ile Asp Ser Asp Tyr Glu Lys
1               5                   10                  15

Pro Glu Thr Pro Glu Cys Val Leu Lys
            20                  25

<210> SEQ ID NO 428
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 428

Trp Met Ser Glu Glu Asp Phe Glu Lys Ala Phe Asn Ala Arg
1               5                   10

<210> SEQ ID NO 429
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 429

Trp Met Ser Glu Glu Asp Phe Glu Lys Ala Phe Asn Ala Arg
1               5                   10

```
<210> SEQ ID NO 430
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 430

Ser Glu Ala Thr Ala Ala Ala Glu His Lys Gly Lys
1               5                  10

<210> SEQ ID NO 431
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 431

Gln Gln Asn Gln His Pro Glu Lys Pro Arg
1               5                  10

<210> SEQ ID NO 432
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 432

Glu Ala Ala Leu Asn Asp Lys Lys Pro Gly Pro Gly Met Asn Gly Ala
1               5                   10                  15

Val Glu Pro Cys Ala Gln Pro Arg
            20

<210> SEQ ID NO 433
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 433

Ala Glu Thr Ala Ala Lys His Gly Glu Ala Gln Val Lys
1               5                   10

<210> SEQ ID NO 434
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 434

Glu Lys Gln Ala Ala Leu Glu Glu Glu Gln Ala Arg
1               5                   10

<210> SEQ ID NO 435
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 435

Gly Ala Ile Gln Leu Gly Ile Gly Tyr Thr Val Gly Asn Leu Ser Ser
1               5                   10                  15
```

Lys Pro Glu Arg
            20

<210> SEQ ID NO 436
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 436

Arg Ser Met Ser Ser Trp Lys Leu Ser Lys
1               5                   10

<210> SEQ ID NO 437
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 437

Ala Ala Ala Gln Tyr Ser Ser Gln Lys Ser Val Glu Glu Arg
1               5                   10

<210> SEQ ID NO 438
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 438

Met Thr Ile Met Glu Gln Lys Tyr Glu Gly Glu Tyr Arg
1               5                   10

<210> SEQ ID NO 439
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 439

Glu Gly Gly Trp Asp Ser Val Gln Asp Trp Met Asp Val Leu Ser Gly
1               5                   10                  15

Gly Glu Lys Gln Arg
            20

<210> SEQ ID NO 440
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 440

Leu Gln Pro Ile Ala Leu Ser Cys Val Leu Asn Ile Gly Ala Cys Lys
1               5                   10                  15

Leu Lys

<210> SEQ ID NO 441
<211> LENGTH: 19
<212> TYPE: PRT
<213> ORGANISM: Artificial Sequence

```
<220> FEATURE:
<223> OTHER INFORMATION: Synthetic Peptide

<400> SEQUENCE: 441

Ser Ser Phe Phe Val Asn Gly Leu Thr Leu Gly Gly Gln Lys Cys Ser
1               5                   10                  15

Val Ile Arg

<210> SEQ ID NO 442
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 442

Ser Val His Lys Val Glu Pro Ile Thr Lys His Ile Gly Leu Val Tyr
1               5                   10                  15

Ser Gly Met Gly Pro Asp Tyr Arg
            20

<210> SEQ ID NO 443
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 443

Ala Arg Tyr Glu Ala Ala Asn Trp Lys Tyr Lys
1               5                   10

<210> SEQ ID NO 444
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 444

Ala Thr Ala Gly Ala Tyr Ile Ala Ser Gln Thr Val Lys Lys
1               5                   10

<210> SEQ ID NO 445
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 445

Tyr Ile Ile Asn Val Lys Gln Phe Ala Lys
1               5                   10

<210> SEQ ID NO 446
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 446

Ile Ile Asn Ala Asp Ser Glu Asp Pro Lys Tyr Ile Ile Asn Val Lys
1               5                   10                  15

Gln Phe Ala Lys
```

```
                        20

<210> SEQ ID NO 447
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 447

Asp Ala Phe Ala Leu Ala Lys Glu Lys
1               5

<210> SEQ ID NO 448
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 448

Asp Ala Phe Ala Leu Ala Lys Glu Lys Ala Pro Ser Ile Ile Phe Ile
1               5                   10                  15

Asp Glu Leu Asp Ala Ile Gly Thr Lys
            20                  25

<210> SEQ ID NO 449
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 449

Ser Glu Asn Asp Leu Lys Ala Leu Gln Ser Val Gly Gln Ile Val Gly
1               5                   10                  15

Glu Val Leu Lys
            20

<210> SEQ ID NO 450
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 450

Ala Val Ala Ser Gln Leu Asp Cys Asn Phe Leu Lys Val Val Ser Ser
1               5                   10                  15

Ser Ile Val Asp Lys
            20

<210> SEQ ID NO 451
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 451

Ala Val Ala Ser Gln Leu Asp Cys Asn Phe Leu Lys Val Val Ser Ser
1               5                   10                  15

Ser Ile Val Asp Lys Tyr Ile Gly Glu Ser Ala Arg
            20                  25
```

<210> SEQ ID NO 452
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 452

Ser Ser Asp Glu Ala Val Ile Leu Cys Lys Thr Ala Ile Gly Ala Leu
1               5                   10                  15

Lys

<210> SEQ ID NO 453
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 453

Ile Ile Ala Phe Val Gly Ser Pro Val Glu Asp Asn Glu Lys Asp Leu
1               5                   10                  15

Val Lys

<210> SEQ ID NO 454
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 454

Asn Phe Lys Val Met Ile Tyr Gln Asp Glu Val Lys
1               5                   10

<210> SEQ ID NO 455
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 455

Tyr Glu Tyr Gly Ile Phe Asn Gln Lys Ile Arg
1               5                   10

<210> SEQ ID NO 456
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 456

Ala Trp Asn Thr Met Val Leu Lys Asn Ile Ala Ala Ser Gly Lys
1               5                   10                  15

<210> SEQ ID NO 457
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 457

```
Ala Trp Asn Thr Met Val Leu Lys Asn Ile Ala Ala Ser Gly Lys
1               5                   10                  15

<210> SEQ ID NO 458
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 458

Thr Ala Ser Asn Val Glu Glu Ala Phe Ile Asn Thr Ala Lys Glu Ile
1               5                   10                  15

Tyr Glu Lys

<210> SEQ ID NO 459
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 459

Lys Glu Asn Pro Leu Gln Phe Lys Phe Arg
1               5                   10

<210> SEQ ID NO 460
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 460

Ile Ala Gln Asp Leu Glu Met Tyr Gly Val Asn Tyr Phe Glu Ile Lys
1               5                   10                  15

Asn Lys Lys

<210> SEQ ID NO 461
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 461

Lys Lys Pro Ile Gln Glu Pro Glu Val Pro Gln Met Asp Ala Pro Ser
1               5                   10                  15

Val Lys

<210> SEQ ID NO 462
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 462

Leu Asp Pro Glu Thr Gly Lys Arg
1               5

<210> SEQ ID NO 463
<211> LENGTH: 13
<212> TYPE: PRT
<213> ORGANISM: Artificial Sequence
```

```
<220> FEATURE:
<223> OTHER INFORMATION: Synthetic Peptide

<400> SEQUENCE: 463

Leu Gly Pro Gly Gln Leu Thr Trp Lys Asn Ser Glu Arg
1               5                   10

<210> SEQ ID NO 464
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 464

Met Lys Gln Glu Pro Val Lys Pro Glu Glu Gly Arg
1               5                   10

<210> SEQ ID NO 465
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 465

Glu Lys Thr Pro Pro Arg Pro Gln Gly Gln Arg Pro Glu Pro Glu Asn
1               5                   10                  15

Arg

<210> SEQ ID NO 466
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 466

Asp Ser Val Lys Asp Lys Glu Lys Gly Lys His Asp Asp Gly Arg
1               5                   10                  15

<210> SEQ ID NO 467
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 467

Leu Lys Thr Pro Pro Arg Pro Gln Gly Gln Arg Pro Ala Pro Glu Ser
1               5                   10                  15

Arg

<210> SEQ ID NO 468
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 468

Glu Lys Thr Cys Pro Leu Cys Arg Thr Val Ile Ser Glu Cys Ile Asn
1               5                   10                  15

Lys
```

```
<210> SEQ ID NO 469
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 469

Ile Thr Val Lys Leu Thr Ile Gln Asn Arg
1               5                   10

<210> SEQ ID NO 470
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 470

Lys Ser Ala Glu Phe Leu Leu His Met Leu Lys Asn Ala Glu Ser Asn
1               5                   10                  15

Ala Glu Leu Lys
            20

<210> SEQ ID NO 471
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 471

Glu Asn Lys Thr Ala Val Val Val Gly Thr Val Thr Asp Asp Val Arg
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 472

Lys Glu Glu Ile Ile Lys Thr Leu Ser Lys Glu Glu Glu Thr Lys Lys
1               5                   10                  15

<210> SEQ ID NO 473
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 473

Thr Leu Ser Lys Glu Glu Glu Thr Lys Lys
1               5                   10

<210> SEQ ID NO 474
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 474

Thr Leu Ser Lys Glu Glu Glu Thr Lys Lys
```

```
<210> SEQ ID NO 475
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 475

Ala Pro Ala Lys Ala Gln Ala Ser Ala Pro Ala Gln Ala Pro Lys
1               5                   10                  15

<210> SEQ ID NO 476
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 476

Ala Gln Ala Ser Ala Pro Ala Gln Ala Pro Lys Gly Ala Gln Ala Pro
1               5                   10                  15

Lys

<210> SEQ ID NO 477
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 477

Ile Gly Gln Gly Tyr Leu Ile Lys Asp Gly Lys
1               5                   10

<210> SEQ ID NO 478
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 478

Leu Ile Lys Asn Asn Ala Ser Thr Asp Tyr Asp Leu Ser Asp Lys
1               5                   10                  15

<210> SEQ ID NO 479
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 479

Ile Leu Lys Ser Pro Glu Ile Gln Arg
1               5

<210> SEQ ID NO 480
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 480
```

```
Leu Asn Pro Tyr Ala Lys Thr Met Arg
1               5

<210> SEQ ID NO 481
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 481

Lys Leu Glu Ala Ala Ala Thr Ala Leu Ala Thr Lys Ser Glu Lys
1               5                   10                  15

<210> SEQ ID NO 482
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 482

Thr Ile Leu Ser Asn Gln Thr Val Asp Ile Pro Glu Asn Val Glu Ile
1               5                   10                  15

Thr Leu Lys Gly Arg
            20

<210> SEQ ID NO 483
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 483

Tyr Val Ala Ser Tyr Leu Leu Ala Ala Leu Gly Gly Asn Ser Ser Pro
1               5                   10                  15

Ser Ala Lys Asp Ile Lys
            20

<210> SEQ ID NO 484
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 484

Leu Lys Thr Glu Gly Ser Asp Leu Cys Asp Arg Val Ser Glu Met Gln
1               5                   10                  15

Lys

<210> SEQ ID NO 485
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 485

Ser Ala Val Pro Pro Gly Ala Asp Lys Lys
1               5                   10

<210> SEQ ID NO 486
<211> LENGTH: 11
```

<212> TYPE: PRT
<213> ORGANISM: Artificial Sequence
<220> FEATURE:
<223> OTHER INFORMATION: Synthetic Peptide

<400> SEQUENCE: 486

Arg Ser Ala Val Pro Pro Gly Ala Asp Lys Lys
1               5                   10

<210> SEQ ID NO 487
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 487

Ser Ala Val Pro Pro Gly Ala Asp Lys Lys Ala Glu Ala Gly Ala Gly
1               5                   10                  15

Ser Ala Thr Glu Phe Gln Phe Arg
            20

<210> SEQ ID NO 488
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 488

Ser Ala Val Pro Pro Gly Ala Asp Lys Lys Ala Glu Ala Gly Ala Gly
1               5                   10                  15

Ser Ala Thr Glu Phe Gln Phe Arg
            20

<210> SEQ ID NO 489
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 489

Arg Ser Ala Val Pro Pro Gly Ala Asp Lys Lys
1               5                   10

<210> SEQ ID NO 490
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 490

Ser Ala Val Pro Pro Gly Ala Asp Lys Lys Ala Glu Ala Gly Ala Gly
1               5                   10                  15

Ser Ala Thr Glu Phe Gln Phe Arg
            20

<210> SEQ ID NO 491
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 491

Asp Val Ile Glu Glu Tyr Phe Lys Cys Lys Lys
1               5                   10

<210> SEQ ID NO 492
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 492

Val Ile Ile Glu Lys Tyr Tyr Thr Arg
1               5

<210> SEQ ID NO 493
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 493

Ile Gly Lys Pro His Thr Val Pro Cys Lys
1               5                   10

<210> SEQ ID NO 494
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 494

Ala Glu Asp Lys Glu Trp Ile Pro Val Thr Lys
1               5                   10

<210> SEQ ID NO 495
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 495

Ser Leu Glu Lys Val Cys Ala Asp Leu Ile Arg
1               5                   10

<210> SEQ ID NO 496
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 496

Phe Asn Gly Gln Phe Lys Thr Tyr Gly Ile Cys Gly Ala Ile Arg
1               5                   10                  15

<210> SEQ ID NO 497
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 497

Asn Thr Lys Gly Gly Asp Ala Pro Ala Ala Gly Glu Asp Ala
1               5                   10

<210> SEQ ID NO 498
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 498

Lys Pro Leu Pro Asp His Val Ser Ile Val Glu Pro Lys Asp Glu Ile
1               5                   10                  15

Leu Pro Thr Thr Pro Ile Ser Glu Gln Lys
            20                  25

<210> SEQ ID NO 499
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 499

Ile Gly Pro Lys Lys Pro Leu Pro Asp His Val Ser Ile Val Glu Pro
1               5                   10                  15

Lys Asp Glu Ile Leu Pro Thr Thr Pro Ile Ser Glu Gln Lys
            20                  25                  30

<210> SEQ ID NO 500
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 500

Gly Gly Lys Pro Glu Pro Pro Ala Met Pro Gln Pro Val Pro Thr Ala
1               5                   10                  15

<210> SEQ ID NO 501
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 501

Asn Ile Gly Lys Thr Leu Val Thr Arg
1               5

<210> SEQ ID NO 502
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 502

Ile Val Lys Pro Asn Gly Glu Lys Pro Asp Glu Phe Glu Ser Gly Ile
1               5                   10                  15

Ser Gln Ala Leu Leu Glu Leu Glu Met Asn Ser Asp Leu Lys
            20                  25                  30

<210> SEQ ID NO 503
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 503

Ile Val Lys Pro Asn Gly Glu Lys Pro Asp Glu Phe Glu Ser Gly Ile
1               5                   10                  15

Ser Gln Ala Leu Leu Glu Leu Glu Met Asn Ser Asp Leu Lys
            20                  25                  30

<210> SEQ ID NO 504
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 504

Ile Val Lys Pro Asn Gly Glu Lys Pro Asp Glu Phe Glu Ser Gly Ile
1               5                   10                  15

Ser Gln Ala Leu Leu Glu Leu Glu Met Asn Ser Asp Leu Lys
            20                  25                  30

<210> SEQ ID NO 505
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 505

Lys Val Ala Lys Val Glu Pro Ala Val Ser Ser Ile Val Asn Ser Ile
1               5                   10                  15

Gln Val Leu Ala Ser Lys
            20

<210> SEQ ID NO 506
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 506

Val Glu Pro Ala Val Ser Ser Ile Val Asn Ser Ile Gln Val Leu Ala
1               5                   10                  15

Ser Lys Ser Ala Ile Leu Glu Ala Thr Pro Lys
            20                  25

<210> SEQ ID NO 507
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 507

Lys Gly Glu Gly Ala Gln Asn Gln Gly Lys Lys Gly Glu Gly Ala Gln
1               5                   10                  15

Asn Gln Ala Lys
            20

```
<210> SEQ ID NO 508
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 508

Lys Gly Glu Gly Ala Gln Asn Gln Ala Lys Lys Gly Glu Gly Ala Gln
1               5                   10                  15

Asn Gln Ala Lys
            20

<210> SEQ ID NO 509
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 509

Lys Gly Glu Gly Ala Gln Asn Gln Ala Lys Lys Gly Glu Gly Gly Gln
1               5                   10                  15

Asn Gln Ala Lys
            20

<210> SEQ ID NO 510
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 510

Lys Gly Glu Gly Gly Gln Asn Gln Ala Lys Lys Gly Glu Gly Ala Gln
1               5                   10                  15

Asn Gln Gly Lys
            20

<210> SEQ ID NO 511
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 511

Lys Gly Glu Gly Ala Gln Asn Gln Gly Lys Lys Gly Glu Gly Ala Gln
1               5                   10                  15

Asn Gln Gly Lys
            20

<210> SEQ ID NO 512
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 512

Lys Gly Glu Gly Ala Gln Asn Gln Ala Lys Lys Gly Glu Gly Val Gln
1               5                   10                  15

Asn Gln Ala Lys
            20
```

<210> SEQ ID NO 513
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 513

Ile Glu Gly Ala Gln Asn Gln Gly Lys Lys Pro Glu Gly Thr Ser Asn
1               5                   10                  15

Gln Gly Lys

<210> SEQ ID NO 514
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 514

Lys Ile Glu Gly Ala Gln Asn Gln Gly Lys Lys Pro Glu Gly Thr Ser
1               5                   10                  15

Asn Gln Gly Lys
            20

<210> SEQ ID NO 515
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 515

Lys Gly Glu Gly Pro Gln Asn Gln Ala Lys Lys Gly Glu Gly Ala Gln
1               5                   10                  15

Asn Gln Gly Lys
            20

<210> SEQ ID NO 516
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 516

Thr Asp Thr Val Ala Asn Gln Gly Thr Lys Gln Glu Gly Val Ser Asn
1               5                   10                  15

Gln Val Lys

<210> SEQ ID NO 517
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 517

Lys Thr Asp Thr Val Ala Asn Gln Gly Thr Lys Gln Glu Gly Val Ser
1               5                   10                  15

Asn Gln Val Lys
            20

```
<210> SEQ ID NO 518
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 518

Ala Ser Met Val Gln Ser Gln Glu Ala Pro Lys Gln Asp Ala Pro Ala
1               5                   10                  15

Lys

<210> SEQ ID NO 519
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 519

Ala Ser Met Val Gln Ser Gln Glu Ala Pro Lys Gln Asp Ala Pro Ala
1               5                   10                  15

Lys

<210> SEQ ID NO 520
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 520

Glu Met Tyr Ser Ala Ser Lys Pro Leu Lys Gly Ala Arg
1               5                   10

<210> SEQ ID NO 521
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 521

Gly Ile Ser Glu Glu Thr Thr Thr Gly Val His Asn Leu Tyr Lys Met
1               5                   10                  15

Met Ser Asn Gly Ile Leu Lys
            20

<210> SEQ ID NO 522
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 522

Gly Ile Ser Glu Glu Thr Thr Thr Gly Val His Asn Leu Tyr Lys Met
1               5                   10                  15

Met Ser Asn Gly Ile Leu Lys
            20

<210> SEQ ID NO 523
<211> LENGTH: 23
<212> TYPE: PRT
```

<213> ORGANISM: Artificial Sequence
<220> FEATURE:
<223> OTHER INFORMATION: Synthetic Peptide

<400> SEQUENCE: 523

Gly Ile Ser Glu Glu Thr Thr Thr Gly Val His Asn Leu Tyr Lys Met
1               5                   10                  15

Met Ser Asn Gly Ile Leu Lys
            20

<210> SEQ ID NO 524
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 524

Gly Ile Ser Glu Glu Thr Thr Thr Gly Val His Asn Leu Tyr Lys Met
1               5                   10                  15

Met Ser Asn Gly Ile Leu Lys Val Pro Ala Ile Asn Val Asn Asp Ser
            20                  25                  30

Val Thr Lys
        35

<210> SEQ ID NO 525
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 525

Gly Ile Ser Glu Glu Thr Thr Thr Gly Val His Asn Leu Tyr Lys Met
1               5                   10                  15

Met Ser Asn Gly Ile Leu Lys Val Pro Ala Ile Asn Val Asn Asp Ser
            20                  25                  30

Val Thr Lys
        35

<210> SEQ ID NO 526
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 526

Gly Ile Ser Glu Glu Thr Thr Thr Gly Val His Asn Leu Tyr Lys Met
1               5                   10                  15

Met Ser Asn Gly Ile Leu Lys Val Pro Ala Ile Asn Val Asn Asp Ser
            20                  25                  30

Val Thr Lys
        35

<210> SEQ ID NO 527
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 527

```
Gly Ile Ser Glu Glu Thr Thr Thr Gly Val His Asn Leu Tyr Lys Met
1               5                   10                  15

Met Ser Asn Gly Ile Leu Lys
            20
```

<210> SEQ ID NO 528
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 528

```
Gly Ile Ser Glu Glu Thr Thr Thr Gly Val His Asn Leu Tyr Lys Met
1               5                   10                  15

Met Ser Asn Gly Ile Leu Lys Val Pro Ala Ile Asn Val Asn Asp Ser
            20                  25                  30

Val Thr Lys
        35
```

<210> SEQ ID NO 529
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 529

```
Val Pro Ala Ile Asn Val Asn Asp Ser Val Thr Lys Ser Lys
1               5                   10
```

<210> SEQ ID NO 530
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 530

```
Ser Lys Phe Asp Asn Leu Tyr Gly Cys Arg
1               5                   10
```

<210> SEQ ID NO 531
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 531

```
Met Leu Glu Leu Val Ala Gln Lys Gln Arg
1               5                   10
```

<210> SEQ ID NO 532
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 532

```
Val Gly Asp Leu Ser Pro Lys Gln Glu Glu Ala Leu Ala Lys
1               5                   10
```

<210> SEQ ID NO 533

```
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 533

Asp Gln Val Lys Gln Gln Tyr Glu His Thr Val Gln Val Ser Arg
1               5                   10                  15

<210> SEQ ID NO 534
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 534

Ala Gln Gly Lys Pro Val Ser Gly Gln Glu Ser Ser Gln Ser Pro Tyr
1               5                   10                  15

Glu Arg

<210> SEQ ID NO 535
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 535

Gln Tyr Asp Ile Ser Asn Pro Gln Lys Pro Arg
1               5                   10

<210> SEQ ID NO 536
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 536

Asn Thr Ser Leu Thr Asp Ile Gln Asp Leu Ser Ser Ile Thr Tyr Asp
1               5                   10                  15

Gln Asp Gly Tyr Phe Lys Glu Thr Ser Tyr Lys Thr Pro Lys Leu Lys
            20                  25                  30

<210> SEQ ID NO 537
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 537

Ala Ile Gly Ile Asp Pro Gly Tyr Ser Lys Ala Tyr Gly Arg
1               5                   10

<210> SEQ ID NO 538
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 538

Lys Val Pro Pro Ala Asp Leu Lys Met Met Cys Leu Glu Glu Asp Ala
```

```
1               5                   10                  15

Ser Glu Arg

<210> SEQ ID NO 539
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 539

Arg Gln Pro Pro Val Ser Gln Gly Leu Leu Glu Thr Leu Lys Ala Arg
1               5                   10                  15

<210> SEQ ID NO 540
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 540

Leu Lys Asp Ala Val Ile Gln Asn Thr Arg
1               5                   10

<210> SEQ ID NO 541
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 541

Val Gly Met Ala Ala Val Lys Leu Ala Pro Gly Lys
1               5                   10

<210> SEQ ID NO 542
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 542

Glu Gly Phe Asp Val Gly Ile Ile Ala Asp Pro Leu Tyr Ile Leu Asp
1               5                   10                  15

Asn Lys Ala Gln Thr Phe Arg
            20

<210> SEQ ID NO 543
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 543

Thr Glu Asp Thr Gln His Cys Gly Glu Gly Lys Gly Phe Leu Gln Lys
1               5                   10                  15

<210> SEQ ID NO 544
<211> LENGTH: 19
<212> TYPE: PRT
<213> ORGANISM: Artificial Sequence
<220> FEATURE:
<223> OTHER INFORMATION: Synthetic Peptide
```

<400> SEQUENCE: 544

Gly Phe Leu Gln Lys Ser Pro Ser Lys Glu Pro His Phe Thr Asp Phe
1               5                   10                  15

Glu Gly Lys

<210> SEQ ID NO 545
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 545

Ser Pro Ser Lys Glu Pro His Phe Thr Asp Phe Glu Gly Lys
1               5                   10

<210> SEQ ID NO 546
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 546

Ala Ala Leu Lys Val Glu Glu Ser Glu Leu Lys
1               5                   10

<210> SEQ ID NO 547
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 547

Leu Thr Glu Lys Glu Ser Glu Cys Thr Asp Val Cys Arg
1               5                   10

<210> SEQ ID NO 548
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 548

Lys Phe Thr Asp Glu Gly Asn Pro Glu Pro Val Asn Asn Asn Gly Tyr
1               5                   10                  15

Ser Cys Val Pro Ser Asp Glu Lys Asn Ser Glu Thr Pro Leu
            20                  25                  30

<210> SEQ ID NO 549
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 549

Ser Ser Leu Thr Thr Ile Glu Lys
1               5

<210> SEQ ID NO 550
<211> LENGTH: 11

```
<212> TYPE: PRT
<213> ORGANISM: Artificial Sequence
<220> FEATURE:
<223> OTHER INFORMATION: Synthetic Peptide

<400> SEQUENCE: 550

Thr Thr Val Lys Ser Ser Glu Leu Gln Gln Leu
1               5                   10

<210> SEQ ID NO 551
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 551

Gln Asp Asp Leu Gly Lys Gly Gly Asn Glu Ser Thr Lys Thr Gly
1               5                   10                  15

Asn Ala Gly Ser Arg
            20

<210> SEQ ID NO 552
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 552

Ser Ala Gly Gly Asp Glu Asn Lys Glu Asn Glu Arg Pro Ser Ala Gly
1               5                   10                  15

Ser Lys

<210> SEQ ID NO 553
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 553

Tyr Gln Ser Asn Pro Lys Val Met Asn Leu Ile Ser Lys
1               5                   10

<210> SEQ ID NO 554
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 554

Glu His Tyr Asp Ser Leu Thr Glu Leu Val Asp Tyr Leu Lys Gly Lys
1               5                   10                  15

<210> SEQ ID NO 555
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 555

Ile Pro Phe Leu Glu Phe Ser Cys Pro Gly Val Pro Pro Gly Leu Glu
1               5                   10                  15
```

Thr Leu Lys Glu Thr Pro Ala Pro Arg
            20                  25

<210> SEQ ID NO 556
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 556

Ser Pro Trp Ile Glu Thr Asp Ile Gly Tyr Ser Ala Leu Ile Asn Lys
1               5                   10                  15

Glu Gly Pro Arg
            20

<210> SEQ ID NO 557
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 557

Met Ala Ser Pro Glu Pro Leu Arg Gly Gly Asp Gly Ala Arg Ala Ser
1               5                   10                  15

Arg Glu Pro His Thr Glu Ala Ser Phe Pro Leu Gln Glu Ser Glu Ser
            20                  25                  30

Pro Lys Glu Ala Lys
        35

<210> SEQ ID NO 558
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 558

Gln Ser Ser Leu Thr Met Asp Gly Gly Asp Val Pro Leu Leu Glu Asp
1               5                   10                  15

Met Ala Ser Gly Ile Val Glu Leu Phe Gln Lys Lys
            20                  25

<210> SEQ ID NO 559
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 559

Ala Leu Ala Gly Cys Asp Phe Leu Thr Ile Ser Pro Lys Leu Leu Gly
1               5                   10                  15

Glu Leu Leu Lys
            20

<210> SEQ ID NO 560
<211> LENGTH: 11
<212> TYPE: PRT
<213> ORGANISM: Artificial Sequence
<220> FEATURE:
<223> OTHER INFORMATION: Synthetic Peptide

```
<400> SEQUENCE: 560

Leu Leu Gly Glu Leu Leu Lys Asp Asn Ser Lys
1               5                   10

<210> SEQ ID NO 561
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 561

Leu Ala Pro Ala Leu Ser Val Lys Ala Ala Gln Thr Ser Asp Ser Glu
1               5                   10                  15

Lys Ile His Leu Asp Glu Lys
            20

<210> SEQ ID NO 562
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 562

Glu Leu Ser Ala Thr Ser Ser Thr Gln Lys Ile Thr Lys
1               5                   10

<210> SEQ ID NO 563
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 563

Gly Ile Thr Gly Ile Glu Asp Lys Glu Ala Trp His Gly Lys Pro Leu
1               5                   10                  15

Pro Lys

<210> SEQ ID NO 564
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 564

Asn Met Ala Glu Gln Ile Ile Gln Glu Ile Tyr Ser Gln Val Gln Ser
1               5                   10                  15

Lys Lys

<210> SEQ ID NO 565
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 565

Ser Gln Thr Glu Glu His Glu Glu Ala Gly Pro Leu Pro Thr Lys Val
1               5                   10                  15

Asn Leu Ala His Ser Glu Ile
            20
```

<210> SEQ ID NO 566
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 566

Ile Ala Trp Thr His Ile Thr Ile Pro Glu Ser Leu Lys Gln Gly Gln
1               5                   10                  15

Val Glu Asp Glu Trp Tyr Ser Leu Ser Gly Arg
            20                  25

<210> SEQ ID NO 567
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 567

Asn Gln Leu Glu Lys Tyr Ile Ser Glu Arg Thr Ser Gln Asp Ser Asn
1               5                   10                  15

Tyr Gly Gly Lys Ile Pro Ile Val Cys Phe Ala Gln Gly Gly Gly Arg
            20                  25                  30

Glu Thr Leu Lys
        35

<210> SEQ ID NO 568
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 568

Asn Glu Val Gly Glu Arg His Gly His Gly Lys Ala Arg
1               5                   10

<210> SEQ ID NO 569
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 569

Thr Leu Lys Leu Thr Thr Pro Thr Tyr Gly Asp Leu Asn His Leu Val
1               5                   10                  15

Ser Ala Thr Met Ser Gly Val Thr Thr Cys Leu Arg
            20                  25

<210> SEQ ID NO 570
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 570

Leu Tyr Ser Met Lys Phe Gln Gly Pro Asp Asn Gly Gln Gly Pro Lys
1               5                   10                  15

```
<210> SEQ ID NO 571
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 571

Lys Pro Leu Leu Glu Ser Gly Thr Leu Gly Thr Lys Gly Asn Val Gln
1               5                   10                  15

Val Val Ile Pro Phe Leu Thr Glu Ser Tyr Ser Ser Gln Asp Pro
            20                  25                  30

Pro Glu Lys
        35

<210> SEQ ID NO 572
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 572

Gly Asn Val Gln Val Val Ile Pro Phe Leu Thr Glu Ser Tyr Ser Ser
1               5                   10                  15

Ser Gln Asp Pro Pro Glu Lys Ser Ile Pro Ile Cys Thr Leu Lys
            20                  25                  30

<210> SEQ ID NO 573
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 573

Ser Ile Pro Ile Cys Thr Leu Lys Asn Phe Pro Asn Ala Ile Glu His
1               5                   10                  15

Thr Leu Gln Trp Ala Arg
            20

<210> SEQ ID NO 574
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 574

Gly Ile Lys Leu Val Val Ala Asp Thr Arg
1               5                   10

<210> SEQ ID NO 575
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 575

Ile Tyr Lys Thr Asp Arg Asp Lys Tyr Asn Arg
1               5                   10

<210> SEQ ID NO 576
<211> LENGTH: 11
```

```
<212> TYPE: PRT
<213> ORGANISM: Artificial Sequence
<220> FEATURE:
<223> OTHER INFORMATION: Synthetic Peptide

<400> SEQUENCE: 576

Ile Tyr His Pro Asn Val Asp Lys Leu Gly Arg
1               5                   10

<210> SEQ ID NO 577
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 577

Ile Cys Leu Asp Ile Leu Lys Asp Lys Trp Ser Pro Ala Leu Gln Ile
1               5                   10                  15

Arg

<210> SEQ ID NO 578
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 578

Ile Cys Leu Asp Ile Leu Lys Asp Lys Trp Ser Pro Ala Leu Gln Ile
1               5                   10                  15

Arg

<210> SEQ ID NO 579
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 579

Lys Ser Glu Asp Asp Gly Ile Gly Lys Glu Asn Leu Ala Ile Leu Glu
1               5                   10                  15

Lys Ile Lys

<210> SEQ ID NO 580
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 580

Val Asp Glu Asn Gly Lys Ile Ser Arg
1               5

<210> SEQ ID NO 581
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 581

Tyr Tyr Lys Val Asp Glu Asn Gly Lys Ile Ser Arg
```

```
1               5                   10

<210> SEQ ID NO 582
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 582

Cys Cys Leu Thr Tyr Cys Phe Asn Lys Pro Glu Asp Lys
1               5                   10

<210> SEQ ID NO 583
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 583

Glu Lys Glu Glu Phe Ala Val Pro Glu Asn Ser Ser Val Gln Gln Phe
1               5                   10                  15

Lys Glu Glu Ile Ser Lys Arg
            20

<210> SEQ ID NO 584
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 584

Val Lys Ile Tyr Thr Phe Asn Gln Ser Arg
1               5                   10

<210> SEQ ID NO 585
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 585

Ala His Val Tyr Val Glu Glu Val Pro Trp Lys Arg
1               5                   10

<210> SEQ ID NO 586
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 586

Asp Ile Val Leu Gln Lys Phe Ala Gly Pro Tyr Asp Lys Gly Glu Tyr
1               5                   10                  15

Ser Pro Ser Val Gln Lys
            20

<210> SEQ ID NO 587
<211> LENGTH: 23
<212> TYPE: PRT
<213> ORGANISM: Artificial Sequence
<220> FEATURE:
```

<223> OTHER INFORMATION: Synthetic Peptide

<400> SEQUENCE: 587

Ser Arg Pro Gly Ser Val Val Pro Ala Asn Leu Phe Gln Gly Ile Lys
1               5                   10                  15

Thr Val Asn Pro Thr Phe Arg
            20

<210> SEQ ID NO 588
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 588

Tyr Val Asp Lys Leu Glu Lys Ile Phe Gln Asn Ala Pro Thr Asp Pro
1               5                   10                  15

Thr Gln Asp Phe Ser Thr Gln Val Ala Lys
            20                  25

<210> SEQ ID NO 589
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 589

Tyr Val Asp Lys Leu Glu Lys Ile Phe Gln Asn Ala Pro Thr Asp Pro
1               5                   10                  15

Thr Gln Asp Phe Ser Thr Gln Val Ala Lys
            20                  25

<210> SEQ ID NO 590
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 590

Lys Tyr Val Asp Lys Leu Glu Lys Ile Phe Gln Asn Ala Pro Thr Asp
1               5                   10                  15

Pro Thr Gln Asp Phe Ser Thr Gln Val Ala Lys
            20                  25

<210> SEQ ID NO 591
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 591

Phe Ala Ser Phe Pro Asp Tyr Leu Val Ile Gln Ile Lys Lys
1               5                   10

<210> SEQ ID NO 592
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 592

Ser Gly Lys Pro Pro Ile Ser Asp Met Phe Ser Asp Leu Lys Asp Gly
1               5                   10                  15

Arg

<210> SEQ ID NO 593
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 593

His Phe Cys Asn Lys Leu Trp Asn Ala Thr Lys
1               5                   10

<210> SEQ ID NO 594
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 594

Leu Gly Asp Val Ile Ser Ile Gln Pro Cys Pro Asp Val Lys Tyr Gly
1               5                   10                  15

Lys Arg

<210> SEQ ID NO 595
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 595

Ile Val Ser Gln Leu Leu Thr Leu Met Asp Gly Leu Lys Gln Arg
1               5                   10                  15

<210> SEQ ID NO 596
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 596

Glu Leu Gln Glu Leu Val Gln Tyr Pro Val Glu His Pro Asp Lys Phe
1               5                   10                  15

Leu Lys

<210> SEQ ID NO 597
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 597

Lys Ser Pro Val Ala Lys Asp Val Asp Leu Glu Phe Leu Ala Lys
1               5                   10                  15

<210> SEQ ID NO 598
<211> LENGTH: 17

```
<212> TYPE: PRT
<213> ORGANISM: Artificial Sequence
<220> FEATURE:
<223> OTHER INFORMATION: Synthetic Peptide

<400> SEQUENCE: 598

Asn Val Asn Ala Gly Gly His Lys Leu Gly Leu Gly Leu Glu Phe Gln
1               5                   10                  15

Ala

<210> SEQ ID NO 599
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 599

Ile Glu Gly Asp Pro Gln Gly Val Gln Gln Ala Lys Arg
1               5                   10

<210> SEQ ID NO 600
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 600

Ile His Val Lys Ser Gly Asp His Met Lys Gly Ala Arg Met Leu Ile
1               5                   10                  15

Arg Val Ala Asn Asn Ile Ser Lys
            20

<210> SEQ ID NO 601
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 601

Asn Tyr Gln Gln Asn Tyr Gln Asn Ser Glu Ser Gly Glu Lys Asn Glu
1               5                   10                  15

Gly Ser Glu Ser Ala Pro Glu Gly Gln Ala Gln Gln Arg
            20                  25

<210> SEQ ID NO 602
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 602

Glu Val Lys Glu Asp Asp Lys Ala Pro Gly Glu Leu Glu Gly Gln Leu
1               5                   10                  15

Ser Glu Asp Gly Ser Ala Pro Glu Lys Gly Glu Val Lys Gly Asn Ala
            20                  25                  30

Ser Leu Arg
        35
```

ANALYSIS OF UBIQUITINATED POLYPEPTIDES

RELATED APPLICATIONS

This Application is a divisional of U.S. Ser. No. 12/967,824 filed Dec. 14, 2010, which claims benefit from U.S. provisional patent application Ser. No. 61/286,486, filed Dec. 15, 2009, the entire disclosures of which are hereby incorporated by reference. The entire disclosures of U.S. Ser. No. 11/823,775 filed Jun. 28, 2007, U.S. Ser. No. 10/777,893, filed Feb. 12, 2004, now U.S. Pat. No. 7,300,753, U.S. Ser. No. 10/175,486, filed Jun. 19, 2002, now U.S. Pat. No. 7,198,896, U.S. Ser. No. 60/299,893, filed Jun. 21, 2001, and U.S. Ser. No. 60/337,012, filed Nov. 8, 2001, are hereby incorporated by reference.

FIELD OF THE INVENTION

This invention provides methods, reagents and kits for analyzing polypeptides and their modifications from biological samples. In particular, the invention provides compositions, kits and methods for detecting ubiquitinated polypeptides and ubiquitination sites in proteins.

BACKGROUND OF THE INVENTION

Personalized medicine is the application of genomic and molecular data to better target the delivery of health care to specific patients, facilitate the discovery and clinical testing of new products, and help determine a person's predisposition to a particular disease or condition.

On a technical level, personalized medicine depends on the identification and detection of proteins, genes and genetic variation ("biomarkers") that play a role in a given disease. Rodland, Clin Biochem. 2004 July; 37(7):579-83. The presence or absence of certain biomarkers is then correlated with the incidence of a particular disease or disease predisposition. However, currently available methods for biomarker analysis are associated with long waiting periods, high cost and numerous technical hurdles.

The current standard for protein detection and/or quantification is based on immunoreactive detection (Western analysis). However, this technique requires the availability of an appropriately specific antibody. In addition, many antibodies only recognize proteins in an unfolded (denatured) form, cross-reactivity can be severely limiting, and quantification is generally relative.

The development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997). However, while these approaches accelerate protein identification, quantities of the analyzed proteins cannot be easily determined, and these methods have not been shown to substantially alleviate the dynamic range problem also encountered by the 2DE/MS/NIS approach. Therefore, low abundance proteins in complex samples are also difficult to analyze by the microcapillary LC/MS/MS method without their prior enrichment.

Protein ubiquitination is the one of the most common of all post-translational modifications. Ubiquitin is a highly conserved 76 amino acid protein which is linked to a protein target after a cascade of transfer reactions. Ubiquitin is activated through the formation of a thioester bond between its C-terminal glycine and the active site cysteine of the ubiquitin activating protein, E1 (Hershko, 1991, Trends Biochem. Sci. 16(7): 265-8). In subsequent trans-thiolation reactions, Ubiquitin is transferred to a cysteine residue on a ubiquitin conjugating enzyme, E2 (Hershko, et al., 1983, J. Biol. Chem. 267: 8807-8812). In conjunction with E3, a ubiquitin polypeptide ligase, E2 then transfers ubiquitin to a specific polypeptide target (see, e.g., Scheffner, et al., 1995, Nature 373(6509): 81-3), forming an isopeptide bond between the C-terminal glycine of ubiquitin and the δ-amino group of a lysine present in the target (See FIG. 1).

The covalent attachment of ubiquitin to cellular polypeptides, in most cases, marks them for degradation by a multi-polypeptide complex called a proteosome. The ubiquitinproteosome system is the principal mechanism for the turnover of short-lived polypeptides, including regulatory polypeptides (Weissman, 2001, Nat. Rev. Mol. Cell. Biol. 2: 169-78). Some known targets of ubiquitination include: cyclins, cyclin-dependent kinases (CDK's), NFKB, cystic fibrosis transduction receptor, p53, ornithine decarboxylase (ODC), 7-membrane spanning receptors, Cdc25 (phosphotyrosme phosphatase), Rb, Gα, c-Jun and c-Fos. Polypeptides sharing consensus sequences such as PEST sequences, destruction boxes, and F-boxes generally are also targets for ubiquitin-mediated degradation pathways (see, e.g., Rogers, et al., 1986, Science 234: 364-368; Yamano, et al., 1998, The EMBO Journal 17: 5670-5678; Bai, et al., 1996, Cell 86: 263-274).

Ubiquitin has been implicated in a number of cellular processes including: signal transduction, cell-cycle progression, receptor-mediated endocytosis, transcription, organelle biogenesis, spermatogenesis, response to cell stress, DNA repair, differentiation, programmed cell death, and immune responses (e.g., inflammation). Ubiquitin also has been implicated in the biogenesis of ribosomes, nucleosomes, peroxisomes and myofibrils. Thus, ubiquitin can function both as signal for polypeptide degradation and as a chaperone for promoting the formation of organelles (see, e.g., Fujimuro, et al., 1997, Eur. J. Biochem. 249: 427-433).

Deregulation of ubiquitination has been implicated in the pathogenesis of many different diseases. For example, abnormal accumulations of ubiquitinated species are found in patients with neurodegenerative diseases such as Alzheimer's as well as in patients with cell proliferative diseases, such as cancer (see, e.g., Hershko and Ciechanover, 1998, Annu Rev. Biochem. 67: 425-79; Layfield, et al., 2001, Neuropathol. Appl. Neurobiol. 27:171-9; Weissman, 1997, Immunology Today 18(4): 189).

While the importance of its biological role is well appreciated, the ubiquitin pathway is inherently difficult to study. Generally, studies of ubiquitination have focused on particular polypeptides. For example, site-directed mutagenesis has been used to evaluate critical amino acids which form the "destruction boxes", or "D-boxes", of cyclin, sites which are rapidly poly-ubiquitinated when cyclin is triggered for destruction. See, e.g., Yamano, et al., 1998, The EMBO Journal 17: 5670-5678; Amon et al., 1994, Cell 77: 1037-1050; Glotzer, et al., 1991, Nature 349: 132-138; King, et al., 1996, Mol. Biol. Cell 7:1343. Corsi, et al., 1997, J. Biol. Chem. 272(5): 2977-2883, which describe a Western blotting approach to identify ubiquitination sites. In this technique, crude radiolabeled α-spectrin fractions were ubiquitinated in vitro, digested with proteases, and electrophoresed on gels.

Ubiquitinated peptides were identified by their differences in mass from peptides generated by digestion of non-ubiquitinated α-spectrin.

Although mass spectrometry offers a powerful tool for identifying ubiquitin substrates, a number of unresolved issues remain. Despite many advances, MS data is inherently biased toward more abundant substrates. The effects of ubiquitin epitope tags used to enriched ubiquinated proteins remain incompletely understood, including whether purification biases exist and whether ubiquitin pathway enzymes utilize tagged and wild-type ubiquitin with equal efficiency. It is also not clear if ubiquitin-binding proteins or ubiquitin antibodies may work efficiently as affinity reagents in order to lessen the need for epitope. Kirkpatrick et al., Nat Cell Biol. 2005 August; 7(8): 750-757.

SUMMARY OF THE INVENTION

One aspect of the invention relates to a method for determining the presence of at least one ubiquitinated polypeptide in a biological sample comprising: Contacting the sample with at least one hydrolyzing agent, wherein the hydrolyzing agent is capable of cleaving a ubiquitinated polypeptide to produce at least one ubiquitin remnant peptide, to obtain a hydrolyzed sample; Contacting the hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the hydrolyzed sample from the substrate in a manner such that the at least one ubiquitin remnant peptide would remain bound to the immobilized binding partner; Contacting the substrate with an elution solution, wherein the least one ubiquitin remnant peptide would dissociate from the immobilized binding partner into the elution solution; and Determining the presence of a least one ubiquitinated polypeptide in the biological sample when the elution solution contains the at least one least ubiquitin remnant peptide.

In one embodiment of this aspect of the invention the determining is performed by LC, MS and preferably LC-MS/MS. In a further embodiment, the amino acid sequence of at least one ubiquitin remnant peptide present in the elution solution, is determined. In yet another embodiment, the sequence is compared to the sequence of the ubiquitinated polypeptide and the site of ubiquitination in the ubiquitinated polypeptide is thereby determined. In still a further embodiment, the elution solution further comprises at least one standard peptide, wherein the at least one standard peptide has the substantially the same amino acid sequence as the at least one distinct peptide but a different measured accurate mass.

Another aspect of the invention relates to an isolated antibody that preferentially binds a ubiquitin remnant peptide over a peptide having the same amino acid sequence as the ubiquitin remnant peptide but lacking a ubiquitin remnant. In one embodiment, the antibody is a monoclonal antibody. In another embodiment, the antibody is a polyclonal antibody. In still yet another embodiment, the antibody is selected from the group consisting of single chain Fvs (scFvs), Fab fragments, Fab' fragments, F(ab') 2, disulfide linked Fvs (sdFvs), Fvs, and fragments thereof. In yet another embodiment, the antibody comprises a polypeptide of SEQ ID NO: 1. In a further embodiment, the antibody comprises a polypeptide of SEQ ID NO: 2. In yet another embodiment, the antibody comprises a light chain polypeptide of SEQ ID NO: 2 and a heavy chain polypeptide of SEQ ID NO: 1. In still another embodiment, the antibody comprises an antigen binding site comprising the variable region of the heavy chain set forth in SEQ ID NO: 1. In still a further embodiment, the antibody comprises an antigen binding site comprising the variable region of the light chain set forth in SEQ ID NO: 2.

Another aspect of the invention relates to an isolated nucleic acid encoding an antibody that preferentially binds a ubiquitin remnant peptide over a peptide having the same amino acid sequence as the ubiquitin remnant peptide but lacking a ubiquitin remnant.

A further aspect of the invention relates to a cell comprising a nucleic acid, preferably in the form of a vector, that encodes an antibody that preferentially binds a ubiquitin remnant peptide over a peptide having the same amino acid sequence as the ubiquitin remnant peptide but lacking a ubiquitin remnant.

Another aspect of the invention relates to the isolated ubiquitin remnant peptides listed in Table 4 and fragments and variants thereof.

Another aspect of the invention relates to nucleic acids encoding the ubiquitin remnant peptides listed in Table 4 and fragments and variants thereof.

Yet a further aspect of the invention relates to a method for determining whether a patient is has or is likely to have or develop a disease associated with a least one ubiquitinated polypeptide comprising: obtaining a biological sample from the patient; Contacting the sample with at least one hydrolyzing agent, wherein the hydrolyzing agent is capable of cleaving a ubiquitinated polypeptide to produce at least one ubiquitin remnant peptide, to obtain a hydrolyzed sample; Contacting the hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the hydrolyzed sample from the substrate in a manner such that the at least one ubiquitin remnant peptide would remain bound to the immobilized binding partner; Contacting the substrate with an elution solution, where in the least one ubiquitin remnant peptide would dissociate from the immobilized binding partner into the elution solution; and Determining the presence of a least one ubiquitinated polypeptide in the biological sample when the elution solution contains the at least one least ubiquitin remnant peptide; Determining that the patient is has or is likely to have or develop the disease associated with a least one ubiquitinated polypeptide if the least one ubiquitinated polypeptide is present in the biological sample.

Another aspect of the invention relates to a method for determining whether a disease is associated with at least one ubiquitinated polypeptide comprising Obtaining a biological sample from a patient having the disease; Contacting the sample with at least one hydrolyzing agent, wherein the hydrolyzing agent is capable of cleaving a ubiquitinated polypeptide to produce at least one ubiquitin remnant peptide, to obtain a hydrolyzed sample; Contacting the hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the hydrolyzed sample from the substrate in a manner such that the at least one ubiquitin remnant peptide would remain bound to the immobilized binding partner; Contacting the substrate with an elution solution, where in the least one ubiquitin remnant peptide would dissociate from the immobilized binding partner into the elution solution; Determining the presence of a least one ubiquitinated polypeptide in the biological sample when the elution solution contains the at least one least ubiquitin remnant peptide; and Determining that the disease is associated with the presence of the at least one ubiquitinated polypeptide if the least one ubiquitinated polypeptide is absent in the biological sample of a healthy individual.

Still another aspect of the invention relates to a method for determining whether a disease is associated with at least one ubiquitin remnant peptide Obtaining a biological sample from a patient having the disease to obtain a disease biological sample; Obtaining a biological sample from a healthy patient to obtains a healthy biological sample; Contacting the disease biological sample with at least one hydrolyzing agent, wherein the hydrolyzing agent is capable of cleaving a ubiquitinated polypeptide to produce the least one ubiquitin remnant peptide, to obtain a disease hydrolyzed sample; Contacting the healthy biological sample with at least one hydrolyzing agent, wherein the hydrolyzing agent is capable of cleaving a ubiquitinated polypeptide to produce the least one ubiquitin remnant peptide, to obtain a healthy hydrolyzed sample; Contacting the disease hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the disease hydrolyzed sample from the substrate in a manner such that the at least one ubiquitin remnant peptide would remain bound to the immobilized binding partner; Contacting the substrate with an elution solution, where in the least one ubiquitin remnant peptide would dissociate from the immobilized binding partner into the elution solution; and Determining the presence of the a least one ubiquitin remnant peptide in the elution solution; Determining that the disease is associated with the presence of the at least one ubiquitin remnant peptide if the least one ubiquitin remnant peptide is absent in the healthy biological sample.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which:

FIG. 2 shows a heat map illustrating the frequency of amino acids found with the BL4936 polyclonal antibody in a study of four mouse tissues. Altogether 1458 non-redundant peptides were included in this frequency map. The map clearly shows there are no strongly preferred amino acids at least seven residues to the amino-terminal side of K(GG) modification sites (−7 to −1 in the figure) or at least seven residues to the carboxyl-terminal side of K(GG) modification sites.

DETAILED DESCRIPTION OF THE INVENTION

Figure 1:
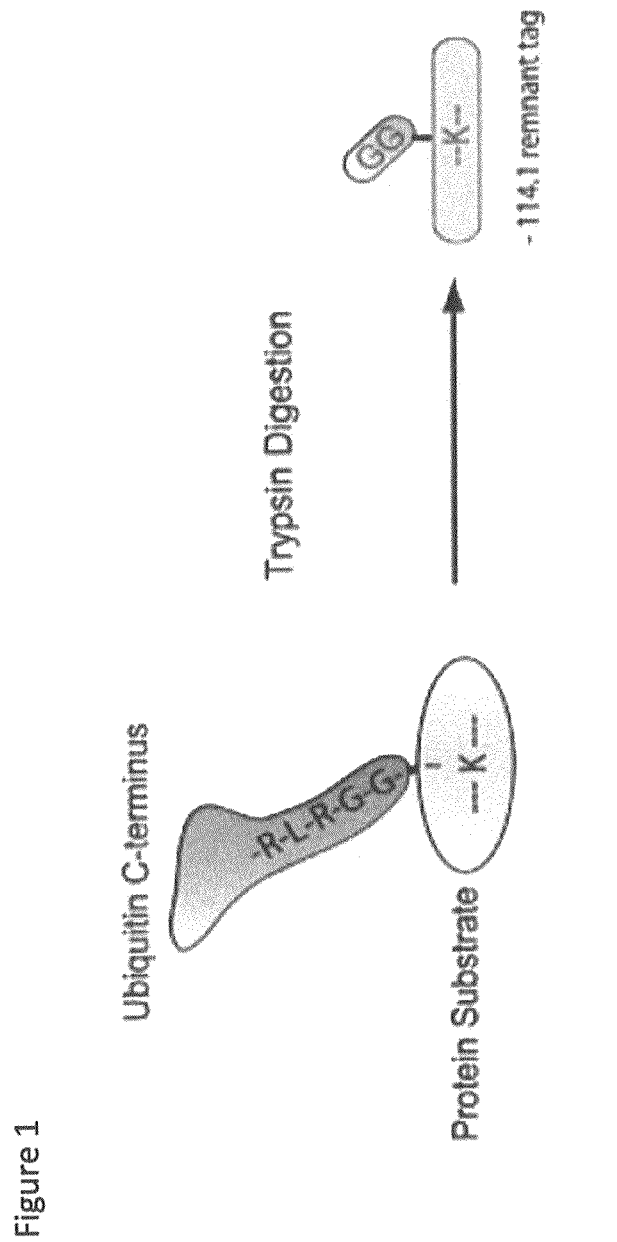
FIG. 1 depicts a cartoon of the formation of a ubiquitin remnant

The inventors have discovered antibody reagents that specifically bind peptides carrying a ubiquitin remnant from a digested or chemically treated biological sample. See also U.S. application Ser. No. 12/455,496 (which is incorporated by reference in its entirety for all purposes and without limitation).

These reagents allow the technician to identify ubiquitinated polypeptides as well as the sites of ubiquitination on them. The reagents are preferably employed in proteomic analysis using mass spectrometry. The antibody reagents (in both polyclonal and monoclonal form) specifically bind the remnant of ubiquitination, i.e., a diglycine modified epsilon amine of lysine left on a peptide which as been generated by digesting or chemically treating ubiquitinated proteins. The inventive antibody reagents' affinity to the ubiquitin remnant does not depend on the remaining amino acid sequences flanking the modified lysine, i.e., they are "context independent". In addition, the antibodies of the invention do not cross react with peptides lacking the ubiquitin remnant. See for example, U.S. Pat. Nos. 6,441,140; 6,982,318; 7,198,896; 7,259,022; 7,300,753; 7,344,714; U.S. Ser. No. 11,484,485, all herein incorporated by reference in their entirety.

Notwithstanding the low abundance of ubiquitinated polypeptides in biological samples, the invention allows for high-throughput MS identification of ubiquitination sites. Immunoaffinity purification (IAP) with the inventive antibodies enrich those ubiquitinated peptides derived from the ubiquitinated portion of polypeptides relative to peptides lacking ubiquitination sites, as well as peptides from proteins which strongly interact with ubiquitin or ubiquitinated proteins, thereby significantly reducing the complexity of the peptide mixture. The purified digest sample can be directly applied to tandem MS for efficient peptide sequence analysis and protein identification to reveal ubiquitinated polypeptides and their sites of ubiquitination.

Prior to describing various embodiments of the current invention, the following definitions are provided:

As used herein the term "peptide" or "polypeptide" refers to a polymer formed from the linking, in a defined order, of preferably, α-amino acids, D-, L-amino acids, and combinations thereof. The link between one amino acid residue and the next is referred to as an amide bond or a peptide bond. Proteins are polypeptide molecules (or having multiple polypeptide subunits). The distinction is that peptides are preferably short and polypeptides/proteins are preferably longer amino acid chains. The term "protein" is intended to also encompass derivatized molecules such as glycoproteins and lipoproteins as well as lower molecular weight polypeptides.

As used herein, the term "ubiquitinated polypeptide" refers to a polypeptide bound to ubiquitin, a ubiquitin-like protein (e.g., NEDD8 or ISG15) or a portion thereof. Preferably, ubiquitination is the formation an isopeptide bond between the C-terminal glycine of ubiquitin (or ubiquitin-like protein see e.g., J Proteome Res. 2008 March; 7(3):1274-87) and the δ-amino group of a lysine present in the target. (See e.g., FIG. 1).

As used herein, a "ubiquitin remnant" or a "ubiquitin tag" is that portion of a ubiquitinated polypeptide which remains attached to the digestion product of the ubiquitinated polypeptide which has been exposed to a hydrolyzing agent such as trypsin. Preferably, the ubiquitin remnant is a diglycine modified epsilon amine of lysine, which adds about 114 daltons to the mass of the lysine residue (see FIG. 1). It is also referred to herein as "K(GG)." Trypsin digestion of neddylated proteins leaves the same K(GG) remnant as trypsin digestion of protein that is attached to ubiquitin.

A "ubiquitin remnant peptide" is the product that results from the digestion of a ubiquitinated polypeptide with a hydrolyzing agent such as trypsin, i.e., a peptide containing at least one ubiquitin remnant. In the preferred embodiment of the invention, a binding partner is used that specifically recognizes and binds to a ubiquitin remnant peptide but does not cross react with other peptides having the same amino acid sequence but which lack the ubiquitin remnant. The preferred binding partner is an antiubiquitin remnant peptide antibody or fragment thereof.

The invention also encompasses the novel ubiquitin remnant peptides disclosed herein in Table 4 as well as fragments and variants thereof.

The term "variant" as used herein relative to ubiquitin remnant peptides, refers to a peptide having a ubiquitin remnant that possesses a similar or identical amino acid sequence as a ubiquitin remnant peptide (e.g., one disclosed in Table 4). A variant having a similar amino acid sequence refers to a peptide comprising, or alternatively
consisting of, an amino acid sequence that is at least 60%, at least 65%, at least 70%, at least 75%, at least 80%, at least 85%, at least 90%, at least 95%, at least 96%, at least 97%, at least 98% or at least 99% identical to the predicate ubiquitin remnant peptide. Peptide variants also include those having a deletion, substitution and/or addition of about 1 to about 2; about 1 to about 3; or about 1 to about 4 amino acids relative to the
predicate ubiquitin remnant peptide.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity number of identical overlapping positions/total number of positions.times.100%). In one embodiment, the two sequences are the same length.

The term "fragment" as used herein refers to a peptide comprising a ubiquitin remnant and an amino acid sequence of at least 3 amino acid residues, at least 5 amino acid residues, at least 7 amino acid residues, at least 10 amino acid residues, at least 15 amino acid residues, at least 20 amino acid residues, at least 25 amino acid residues, at least 30 amino acid residues of a ubiquitin remnant peptide.

The invention also includes nucleic acids that encode for the ubiquitin remnant peptides disclosed herein in Table 4 as well as fragments and variants thereof.

As used herein, the term "biological sample" refers to a readily obtainable mixture of a plurality of polypeptides present in varying concentrations. Preferred biological samples have about 5,000 to about 20,000 different polypeptides. More preferably, biological samples have about 7,500 to about 15,000 different polypeptides. Most preferably, biological samples have about 10,000 different polypeptides. Generally, such samples are environmental, industrial, veterinary or medical in origin and from an animal, plant, a bacterium, a fungus, a protist or a virus. The preferred biological samples include but are not limited to saliva, mucous, tears, blood, serum, lymph/interstitial fluids, buccal cells, mucosal cells, cerebrospinal fluid, semen, feces, plasma, urine, a suspension of cells, or a suspension of cells and viruses. The most preferred biological samples are mammalian, more preferably human, serum and urine.

Where the biological sample is blood, serum or lymph/interstitial fluid, the invention envisages an optional step of depleting the biological sample of common and dispropor-tionally over-represented background proteins not suspected of being associated with ubiquitinated polypeptides. Such proteins include but are not limited to albumin, IgG, IgA, transferrin, haptoglobin, and anti-trypsin; or combinations thereof. The skilled artisan will recognized that such a step is carried out by basic affinity chromatography techniques. As used here in the term "depleted" or "depleting" means markedly lessening the concentration of a particular species in a solution, e.g., by more than or about 50%; more than or about 60%; more than or about 65%; more than or about 70%; more than or about 75%; more than or about 80%; more than or about 85%; more than or about 90%; more than or about 92%; more than or about 95%; more than or about 97%; more than or about 98%; more than or about 99%. Alternatively the biological sample may be a subcellular fraction of a cell line or tissue, enriched for specific cellular organelles such as nuclei, cytoplasm, plasma membranes, mitochondria, internal membrane structures, Golgi apparatus, endoplasmic reticulum, etc. or specific tissue organelles such as post-synaptic densities from brain, islets from pancreas, etc.

As used herein, the term "hydrolyzing agent" refers to any one or combination of a large number of different enzymes, including but not limited to trypsin, Lysine-C endopeptidase (LysC), arginine-C endopeptidase (ArgC), Asp-N, glutamic acid endopeptidase (GluC) and chymotrypsin, V8 protease and the like, as well as chemicals, such as cyanogen bromide. In the subject invention one or a combination of hydrolyzing agents cleave peptide bonds in a protein or polypeptide, in a sequence-specific manner, generating a predictable collection of shorter peptides (a "digest"). A portion of the biological samples are contacted with hydrolyzing agent(s) to form a digest of the biological sample. Given that the amino acid sequences of certain polypeptides and proteins in biological samples are often known and that the hydrolyzing agent(s) cuts in a sequence-specific manner, the shorter peptides in the digest are generally of a predicable amino acid sequence. Preferably, the treatment of a polypeptide with a hydrolyzing agents results in about 2 to about 20, more preferably about 5 to about 15 and most preferably about 10 peptides. If the polypeptide in a biological sample is a ubiquitinated polypeptide, at least one of the resulting peptides in the digest will be a ubiquitin remnant peptide. The preferred hydrolyzing agent is a protease, or chemical which cleaves ubiquitinated proteins in a manner that results in the formation of at least one ubiquitin remnant peptide. Most preferably, the protease is trypsin.

The term "mass spectrometer" means a device capable of detecting specific molecular species and measuring their accurate masses. The term is meant to include any molecular detector into which a polypeptide or peptide may be eluted for detection and/or characterization. In the preferred MS procedure, a sample, e.g., the elution solution, is loaded onto the MS instrument, and undergoes vaporization. The components of the sample are ionized by one of a variety of methods (e.g., by electrospray ionization or "ESI"), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. The preferred mass measurement error of a mass spectrometer of the invention is 10 ppm or less, more preferable is 7 ppm or less; and most preferably 5 ppm or less.

Fragment ions in the MS/MS and MS$^3$ spectra are generally highly specific and diagnostic for peptides of interest. In contrast, to prior art methods, the identification of peptide diagnostic signatures provides for a way to perform highly selective analysis of a complex protein mixture, such as a cellular lysate in which there may be greater than about 100, about 1000, about 10,000, or even about 100,000 different kinds of proteins. Thus, while conventional mass spectroscopy would not be able to distinguish between peptides with different sequences but similar m/z ratios (which would tend to co-elute with any labeled standard being analyzed), the use of peptide fragmentation methods and multistage mass spectrometry in conjunction with LC methods, provide a way to detect and quantify target proteins which are only a small fraction of a complex mixture (e.g., present in less than 2000 copies per cell or less than about 0.001% of total cellular protein) through these diagnostic signatures.

Test peptides are preferably examined by monitoring of a selected reaction in the mass spectrometer. This involves using the prior knowledge gained by the characterization of a standard peptide and then requiring the mass spectrometer to continuously monitor a specific ion in the MS/MS or MS spectrum for both the peptide of interest and the standard peptide. After elution, the areas-under-the-curve (AUC) for both the standard peptide and target peptide peaks may be calculated. The ratio of the two areas provides the absolute quantification that may then be normalized for the number of cells used in the analysis and the protein's molecular weight, to provide the precise number of copies of the protein per cell.

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement about 5 ppm uncertainty is sufficient to uniquely determine the elemental composition.

As used herein the term, "predetermined peptide accurate mass" refers to the experimentally determined or calculated accurate mass of a peptide with a known amino acid sequence (along with any associated post-translational modifications). The accurate mass of any such specific amino acid sequence may be readily calculated by one of skill in the art.

As used herein, "a peptide fragmentation signature" refers to the distribution of mass-to-charge ratios of fragmented peptide ions obtained from fragmenting a peptide, for example, by collision induced disassociation, ECD, LID, PSD, IRNPD, SID, and other fragmentation methods. A peptide fragmentation signature which is "diagnostic" or a "diagnostic signature" of a target protein or target polypeptide is one which is reproducibly observed when a peptide digestion product of a target protein/polypeptide identical in sequence to the peptide portion of a standard peptide, is fragmented and which differs only from the fragmentation pattern of the standard peptide by the mass of the mass-altering label and/or the presence of a ubiquitin remnant. Preferably, a diagnostic signature is unique to the target protein (i.e., the specificity of the assay is at least about 95%, at least about 99%, and preferably, approaches 100%).

The term "substrate" includes any solid support or phase upon which a binding partner may be immobilized. Preferred supports are those well known in the art of affinity chromatography for example but not limited to polymeric and optionally magnetic beads, polystyrene, sepharose or agarose gel matrices, or nitrocellulose membranes.

The term "binding partner" refers to any of a large number of different molecules or aggregates. Preferably, a binding partner functions by binding to a polypeptide or peptide in order to enrich it prior to analysis, e.g., by MS, LC-MS, or LC-MS/MS. Preferably, binding partners bind ubiquitin remnant peptides to enrich in a digest. Proteins, polypeptides, peptides, nucleic acids (oligonucleotides and polynucleotides), antibodies, ligands, polysaccharides, microorganisms, receptors, antibiotics, and test compounds (particularly those produced by combinatorial chemistry) may each be a binding partner.

In the preferred one embodiment, the binding partner is immobilized by being directly or indirectly, covalently or non-covalently bound to the substrate. In another embodiment, the binding partner does not require a substrate and can be used to immuno-precipitate the ubiquitin remnant peptides for example. In a further embodiment, the binding partner can be used to bind ubiquitin remnant peptides in solution. The technician could then enrich for ubiquitin remnant peptides by filtering ubiquitin remnant peptide-binding partner complexes, through size cut-off or size exclusion chromatography for example.

The preferred binding partner is a "ubiquitin remnant peptide specific antibody" or an "anti-ubiquitin remnant antibody" which specifically yet reversibly binds ubiquitin remnant peptides and does not bind (i.e., cross react with) peptides having the same amino acid sequence but which lack the ubiquitin remnant. As such, the preferred ubiquitin remnant peptide-specific antibodies bind ubiquitin remnant peptides in a context independent manner.

Accordingly, the invention provides an isolated antibody or binding partner that preferentially binds a ubiquitin remnant peptide over a peptide having the same amino acid sequence as the ubiquitin remnant peptide but lacks the ubiquitin remnant. In some embodiments, the isolated antibody or binding partner specifically binds a ubiquitin remnant peptide but does not specifically bind a peptide having the same amino acid sequence as the ubiquitin remnant peptide but lacks the ubiquitin remnant. As used herein, by "specifically binds" is meant that a binding partner or an antibody of the invention interacts with its target molecule (e.g., a ubiquitin remnant peptide), where the interaction is dependent upon the presence of a particular structure (e.g., the antigenic determinant or epitope on the peptide); in other words, the reagent is recognizing and binding to a specific polypeptide structure rather than to all polypeptides in general. In some embodiments, the isolated antibodies or isolated binding partners do not specifically bind to a peptide having the same amino acid sequence as the ubiquitin remnant peptide but lacks the ubiquitin remnant.

The isolated antibodies and/or isolated binding partners of the invention can be used in the methods of the invention.

It should be understood that the substrate can have a number many different binding partners having a different binding specificity for a different polypeptide, peptide, subiquitin remnant peptide or epitopes thereof. As such, binding partners might be derived from monoclonal sources or polyclonal sera. Preferably, the substrate has about 2 to about 500, more preferably about 5 to about 400, even more preferably about 10 to about 300 and most preferably about 15 to about 200, yet even more preferably about 20 to about 100, about 25 to about 75 and about 30 to about 60 different binding partners each specifically binding to a different and/or distinct peptide. This allows the technician to simultaneously process and analyze the biological sample for the presence of a large number of polypeptides in a manner not feasible with multiplex PCR or ELISA techniques. Additional methods and reagents for immunoaffinity purification and/or enrichment of peptides containing certain motifs such as the ubiquitin remnant may be found in e.g., in U.S. Pat. Nos. 7,198,896 and 7,300,753.

The term "antibody" as used herein, refers to immunoglobulin molecules and immunologically active portions of immunoglobulin molecules, i.e., molecules that contain an antigen binding site that specifically binds to an antigen. As such, the term antibody encompasses not only whole antibody molecules, but also antibody multimers and antibody fragments, as well as variants (including derivatives) of antibodies, antibody multimers and antibody fragments. The preferred antibody disclosed herein is referred to as D4A7A10.

The basic antibody structural unit is known to comprise a tetramer. Each tetramer is composed of two identical pairs of polypeptide chains, each pair having one "light" (about 25 kilodalton) and one "heavy" chain (about 50-70 kilodalton).

The amino-terminal portion of each chain includes a variable region of about, 80, 85, 90, 95, 100, 105, preferably 100 to 110 or more amino acids primarily responsible for antigen recognition. Herein the terms "heavy chain" and "light chain" refer to the heavy and light chains of an antibody unless otherwise specified. The amino acid sequence of the D4A7A10 heavy chain is set forth in SEQ ID NO: 1. The amino acid sequence of the D4A7A10 light chain is set forth in SEQ ID NO: 2.

The carboxy-terminal portion of each chain preferably defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, Fundamental Immunology Ch. 7 (Paul, W., ed., 2nd ed. Raven Press, N.Y. (1989)) (incorporated by reference in its entirety for all purposes). The variable regions of each light ("VL")/heavy chain ("VH") pair preferably form the antibody binding site. Thus, an intact IgG antibody has two binding sites. Except in bifunctional or bispecific antibodies, the two binding sites are the same. The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, J. Mol. Biol. 196:901-917 (1987); Chothia et al., Nature 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" EMBO J. 10:3655-3659 (1991) and Traunecker et al. "Janusin: new molecular design for bispecific reagents" Int J Cancer Suppl 7:51-52 (1992)). Production of bispecific antibodies can be a relatively labor intensive process compared with production of conventional antibodies and yields and degree of purity are generally lower for bispecific antibodies.

Examples of molecules which are described by the term "antibody" herein include, but are not limited to: single chain Fvs (sdFvs), Fab fragments, Fab' fragments, F(ab')2, disulfide linked Fvs (sdFvs), Fvs, and fragments thereof comprising or alternatively consisting of, either a VL or a VH domain. The term "single chain Fv" or "scFv" as used herein refers to a polypeptide comprising a VL domain of antibody linked to a VH domain of an antibody.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG1, IgG$_2$, IgG$_3$, IgG$_4$, IgA$_1$ and IgA$_2$) or subclass of immunoglobulin molecule. Preferably, an antibody of the invention comprises, or alternatively consists of, a VH domain, VH CDR, VL domain, or VL CDR having an amino acid sequence of any one of the antibodies listed in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms. Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1 carboxylate] and SATA [Nsuccinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the mature J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31. and Frigerio et al., (2000) Plant Physiology 123:1483-94, both of which are hereby incorporated by reference in their entireties.) IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to contain a J chain interaction domain) is not desired, it can be greatly reduced by expressing the antibody molecule in association with a mutant J chain that does not interact well with pIgR (Johansen et al., The Journal of Immunology (2001) 167:5185-5192 which is hereby incorporated by reference in its entirety). ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

Monoclonal and polyclonal context-independent ubiquitin remnant peptide antibodies have been identified. For example, the invention encompasses the monoclonal and polyclonal antibodies listed in Table 1 and the cell lines engineered to express them or capable of expressing them.

Further, the present invention encompasses the polynucleotides encoding the anti-ubiquitin remnant peptide antibodies or portions thereof. Molecules encoding e.g., VH domains, VH CDRs, VL domains, or VL CDRs having an amino acid sequence of the corresponding region of the inventive antibodies expressed by a cell that specifically bind to ubiquitin remnant peptides but not peptides having the same amino acid sequence but lacking the ubiquitin remnant, or fragments or variants thereof are also encompassed by the invention, as are nucleic acid molecules that encode these antibodies and/or molecules. In specific embodiments, the present invention encompasses antibodies, or fragments or variants thereof that bind to an epitope that comprises the ubiquitin remnant.

Methods for identifying the complementarity determining regions (CDRs) of an antibody by analyzing the amino acid sequence of the antibody are well known (see, e.g., Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol. Biol. 275(2):269-94 (Jan. 1998); Chothia et al., Nature 342(6252):877-83 (December 1989); Ponomarenko and Bourne, BMC Structural Biology 7:64 (2007).

As one non-limiting example, the following method can be used to identify the CDRs of an antibody.

For the CDR-L1, the CDR-L1 is approximately 10-17 amino acid residues in length. Generally, the start is at approximately residue 24 (the residue before the 24$^{th}$ residue is typically a cysteine. The CDR-L1 ends on the residue before a tryptophan residue. Typically, the sequence containing the tryptophan is either Trp-Tyr-Gln, Trp-Leu-Gln Trp-Phe-Gln, or Trp-Tyr-Leu, where the last residue within the CDR-L1 domain is the residue before the TRP in all of these sequences.

For the CDR-L2, the CDR-L2 is typically seven residues in length. Generally, the start of the CDR-L2 is approximately sixteen residues after the end of CDR-L1 and typically begins on the on the residue after the sequences of Ile-Tyr, Val-Tyr, Ile-Lys, or Ile-Phe.

For the CDR-L3, the CDR-L3 is typically 7-11 amino acid residues in length. Generally, the domain starts approximately 33 residues after the end of the CDR-L2 domain. The residue before the start of the domain is often a cysteine and the domain ends on the residue before Phe in the sequence Phe-Gly-XXX-Gly (where XXX is the three letter code of any single amino acid.

For the CDR-H1, the CDR-H1 domain is typically 10-12 amino acid residues in length and often starts on approximately residue 26. The domain typically starts four or five residues after a cysteine residue, and typically ends on the residue before a Trp (the Trp is often found in one of the following sequences: Trp-Val, Trp-Ile, or Trp-Ala.

For the CDR-H2, the CDR-H2 domain is typically 16 to 19 residues in length and typically starts 15 residues after the final residue of the CDR-H1 domain. The domain typically ends on the amino acid residue before the sequence Lys/Arg-Leu/Ile/Val/Phe/Thr/Ala-Thr/Ser/Ile/Ala (which includes, for example, the sequences Lys-Leu-Thr and Arg-Ala-Ala).

For the CDR-H3, the CDR-H3 domain is typically 3-25 amino acids in length and typically starts 33 amino acid residues after the final residues of the CDR-H2 domain (which is frequently two amino acid residues after a cysteine residue, e.g., a cysteine in the sequence Cys-Ala-Arg). The domain ends on the amino acid immediately before the Trp in the sequence Trp-Gly-XXX-Gly (where XXX is the three letter code of any single amino acid).

The inventive anti-ubiquitin remnant peptide antibodies may be coupled to a detectable label such as an enzyme, a fluorescent label, a luminescent label, or a bioluminescent label. The present invention also provides anti-ubiquitin remnant peptide antibodies that are coupled to a therapeutic or cytotoxic agent. The present invention also provides anti-PA antibodies which are coupled, directly or indirectly, to a radioactive material.

In further embodiments, the anti-ubiquitin remnant peptide antibodies of the invention have a dissociation constant ($K_D$) of $10^{-7}$ M or less for a ubiquitin remnant peptide. In preferred embodiments, the anti-ubiquitin remnant peptide antibodies of the invention have a dissociation constant ($K_D$) of $10^{-9}$ M or less for a ubiquitin remnant peptide.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides panels of the anti-ubiquitin remnant peptide antibodies (including molecules comprising, or alternatively consisting of, antibody fragments or variants) wherein the panel members correspond to one, two, three, four, five, ten, fifteen, twenty, or more different the anti-ubiquitin remnant peptide antibodies of the invention (e.g., whole antibodies, Fabs, F(ab')$_2$ fragments, Fd fragments, disulfide-linked Fvs (sdFvs), anti-idiotypic (anti-Id) antibodies, and scFvs). The present invention further provides mixtures of the anti-ubiquitin remnant peptide antibodies wherein the mixture corresponds to one, two, three, four, five, ten, fifteen, twenty, or more different the anti-ubiquitin remnant peptide antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more the anti-ubiquitin remnant peptide antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more of the anti-ubiquitin remnant peptide antibodies or fragments or variants thereof. Alternatively, a composition of the invention may comprise, or alternatively consist of, nucleic acid molecules encoding one or more antibodies of the invention.

The present invention also provides for fusion proteins comprising an anti-ubiquitin remnant peptide antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention.

Alternatively, a composition of the invention may comprise, or alternatively consist of, nucleic acid molecules encoding one, two, three, four, five, ten, fifteen, twenty or more fusion proteins of the invention.

The term "elution solution" refers to a solution that when brought into contact with the binding partner, results in the dissociation of the polypeptide or peptide and preferably the ubiquitin remnant peptide from the binding partner into the elution solution. Determining the salt, pH and ionic conditions necessary for such functionality is well with the ordinary skill in the art. Preferably, the elution solution is enriched for polypeptides and peptides which were bound to the binding partners relative to the polypeptides and peptides of the digest. Preferably, the elution solution has about 500 to about 5000, more preferably about 1000 to about 2000 different peptides. Most preferably, the elution solution is enriched for ubiquitin remnant peptides. Preferably, a portion of the elution solution is directly transferred to a mass spectrometer, LC-MS or LC-MS/MS. Alternatively, the elution solution is subject to further manipulation e.g., to concentrate the peptides and/or polypeptides contained therein. Mechanisms for directing solutions from liquid chromatography to mass spectrometers may be found for example in U.S. Pub. No. 20080217254.

The term "vaporizing a portion of the elution solution" means that a portion of the elution solution is preferably transferred to a mass spectrometer for vaporization and ionization.

The term "ionizing" refers to atmospheric pressure chemical ionization (APCI), chemical ionization (CI), electron impact (O), electrospray ionization (ESI), fast atom bombardment (FAB), field desorption/field ionization (FD/FI), matrix assisted laser desorption ionization (MALDI), and thermospray ionization. The preferred method of ionization is ESI as tends to minimize the propensity of macromolecules to fragment when ionized.

Preferably in ESI, liquid containing the peptides of interest is dispersed by electrospray into a fine aerosol. Preferred solvents for electrospray ionization are prepared by mixing water with volatile organic compounds (e.g. methanol, acetonitrile). To decrease the initial droplet size, compounds that increase the conductivity (e.g. acetic acid) are preferably added to the solution. Large-flow electrosprays may provide additional nebulization by an inert gas such as nitrogen. The aerosol is sampled into the first vacuum stage of a mass spectrometer through a capillary, which can be heated to aid further solvent evaporation from the charged droplets. Preferably, the solvent evaporates from a charged droplet until it becomes unstable upon reaching its Rayleigh limit. At this point, the droplet preferably deforms and emits charged jets in a process known as Rayleigh fission. During the fission, the droplet loses a small percentage of its mass along with a relatively large percentage of its charge As used herein, "ionized molecule" refers to molecules in the elution solution that have become charged and are ready to move into the electric fields that will direct them into the mass analyzer of a mass spectrometer. Preferably, the ionized molecules include ionized polypeptides, peptides and/or ubiquitin remnant peptides present in the elution solution. Most preferably, the ionized molecules are ubiquitin remnant peptides.

The term "standard peptide" as used herein, refers to a peptide that is 1) recognized as equivalent to a peptide of interest in the digest generated by a hydrolyzing agent, e.g., the ubiquitin remnant peptide, by the appropriate binding partner; and 2) differs from the peptide of interest in a manner that can be distinguished by a mass spectrometer, e.g., by way of a mass-altering label. Preferably, the standard peptide has the same amino acid sequence as the ubiquitin remnant peptide but is synthesized utilizing elemental isotopes. Preferably, those isotopes are $^{15}$N, $^{13}$C, $^{18}$O or $^{2}$H. Alternatively, a standard peptide can 1) have the same amino acid sequence as a ubiquitin remnant peptide yet lack the ubiquitin remnant; and 2) differ from the ubiquitin remnant peptide in a manner that can be distinguished by a mass spectrometer, e.g., by lacking the ubiquitin remnant. Exemplary standard peptides are described in U.S. Pub. No. 20060154318 and 20060148093. One or more standard peptides may be added to the biological sample before or after treatment with a hydrolyzing agent such that it co-elutes with the peptide of interest into the elution solution. The standard peptide can be added directly to the elution solution.

One aspect of the invention relates to providing methods for determining a site of ubiquitination in a polypeptide. The method comprises obtaining a plurality of ubiquitinated polypeptides; digesting the ubiquitinated polypeptides with a protease, thereby generating a plurality of test peptides; enriching the plurality of test peptides for ubiquitin remnant peptides; and determining the presence of a ubiquitin remnant peptide by mass spectrometry, wherein the presence of the ubiquitin remnant peptide allows the technician to determine a site of ubiquitination of the polypeptide. The test peptide being evaluated can be ionized and/or fragmented prior to the determining step. Preferably, ionizing is performed by electrospray.

In one embodiment of this aspect of the invention, the method for determining a site of ubiquitination comprises obtaining a plurality of ubiquitinated polypeptides; digesting the ubiquitinated polypeptides with a protease; thereby generating a plurality of test peptides; at least some of which comprise a ubiquitin remnant, enriching the plurality of test peptides for ubiquitin remnant peptides; and identifying a mass difference between a test peptide and a standard peptide comprising a known identical amino acid sequence as the test peptide; the mass difference corresponding to the mass of the ubiquitin remnant, wherein detection of the mass difference indicates a site of ubiquitination in the test peptide.

In another aspect, the methods further comprise the step of mapping a sequence of a test peptide comprising a ubiquitin remnant to a polypeptide sequence comprising the same amino acid sequence as the test peptide, thereby determining the site of ubiquitination in the polypeptide sequence. In another embodiment, the ubiquitin remnant comprises GlyGly amino acid residues and has a mass of about 114 daltons. The methods can be used to detect one or more sites of ubiquitination in a polypeptide, as well as the amount of ubiquitination at particular sites in a population of polypeptides.

In a further aspect of the invention, ubiquitination sites are identified for a plurality of polypeptides in a first cell and in a second cell and the sites identified in the first cell are compared to those in the second cell. In one aspect, the first cell is a normal cell (e.g., from a healthy patient), while the second cell is from a patient with a pathological condition (e.g., a neurodegenerative disease, cancer, a disease of the immune system). Preferably, the second cell is the target of the pathology (e.g., a tumor cell from a cancer patient; a neural cell from a patient with a neurodegenerative disease). In another embodiment of this aspect of the invention, the second cell differs from the first cell in expressing one or more recombinant DNA molecules, but is otherwise genetically identical to the first cell. In a further embodiment, the site of ubiquitination is correlated with disease and detection of ubiquitination at the site is associated with risk of the disease. In another embodiment, the disease is a eurodegenerative disease, such as Alzheimer's or Pick's disease. In another aspect, the disease is cancer. In a further aspect, the disease is an abnormal immune response or inflammatory disease.

In another aspect of the invention, the methods disclosed herein are used to identify regulators of ubiquitination pathways. In one embodiment, the methods further comprise contacting a first cell with a compound and comparing ubiquitination sites identified in the first cell with ubiquitination sites in a second cell not contacted with the compound. The compound may be a therapeutic agent for treating a disease associated with an improper state of ubiquitination (e.g., abnormal sites or amounts of ubiquitination). Suitable agents include, but are not limited to, drugs, polypeptides, peptides, antibodies, nucleic acids (genes, cDNA's, RNA's, antisense molecules, siRNA/miRNA constructs, ribozymes, aptamers and the like), toxins, and combinations thereof.

Preferably, the methods further comprise generating a database comprising data files storing information relating to ubiquitination sites for a plurality of polypeptides for a plurality of different cells. Preferably, the data files also include information relating to amount of ubiquitination of a polypeptide in at least one cell. Additionally, the database comprises data relating to the source of the cell (e.g., such as a patient).

The invention further provides a computer memory comprising data files storing information relating to ubiquitination sites for a plurality of polypeptides for a plurality of different cells.

In another aspect of the invention, substantially purified test peptides, preferably ubiquitin remnant peptides, obtained after one or more separation steps are analyzed by a peptide analyzer that evaluates the mass of the peptide or a fragment thereof. Suitable peptide analyzers include, but are not limited to, a mass spectrometer, mass spectrograph, single-focusing mass spectrometer, static field mass spectrometer, dynamic field mass spectrometer, electrostatic analyzer, magnetic analyzer, quadropole analyzer, time of flight analyzer (e.g., a MALDI Quadropole time-of-flight mass spectrometer), Wien analyzer, mass resonant analyzer, double-focusing analyzer, ion cyclotron resonance analyzer, ion trap analyzer, tandem mass spectrometer, liquid secondary ionization MS, and combinations thereof in any order (e.g., as in a multi-analyzer system). Such analyzers are known in the art and are described in, for example, Mass Spectrometry for the Biological Sciences, Burlingame and Can eds., Human Press, Totowa, N.J.)

In general, any analyzer can be used that can separate matter according to its anatomic and molecular mass. Preferably, the peptide analyzer is a tandem MS system (an MS/MS system) since the speed of an MS/MS system enables rapid analysis of low femtomole levels of peptide and can be used to maximize throughput.

In a preferred embodiment of this aspect of the invention, the peptide analyzer comprises an ionizing source for generating ions of a test peptide and a detector for detecting the ions generated. The peptide analyzer further comprises a data system for analyzing mass data relating to the ions generated and for deriving mass data relating to the test peptide.

A sample comprising a test peptide can be delivered to the peptide analyzer using a delivery mechanism as described above. Interfaces between a sample source (e.g., an HPLC column) and ion source can be direct or indirect. For example, there may be an interface that provides for continuous introduction of the sample to the ion source. Alternatively, sample can be intermittently introduced to the ion source (e.g., in response to feedback from the system processor during the separation process, or while the separation system is off-line).

In another embodiment, the ion source is an electrospray which is used to provide droplets to the peptide analyzer, each droplet comprising a substantially purified test peptide obtained from previous separation step(s) (e.g., such as HPLC or reversed phase liquid chromatography). During electrospray, a high voltage is applied to a liquid stream causing large droplets to be subdivided into smaller and smaller droplets until a peptide enters the gas phase as an ion. Ionization generally is accomplished when the test peptide loses or gains a proton at one or more sites on the peptide (e.g., at the amino terminus, and/or at lysine and arginine residues). Ionization in electrospray is constant; MALDI can be used to achieve pulsed ionization. Other methods of ionization, include but are not limited to, plasma desorption ionization, thermospray ionization, and fast atom bombardment ionization as are known in the art.

When MALDI is used, peptides can be delivered to a solid support, e.g., sample plate inserted into the mass spectrometer. The support may comprise a light-absorbent matrix. In another embodiment, a substantially purified ubiquitinated polypeptide is provided on a sample plate and protease digestion occurs on the sample plate prior to ionization. For example, substantially purified ubiquitinated peptides also can be obtained from protease digests as described above and separated by a liquid chromatography method. Preferably, the peptide analyzer further comprises an ion transfer section through which ions are delivered from the ion source to the detector. The ion transfer section comprises an electric and/or magnetic field generator (e.g., an electrode ring) that modulates the acceleration of ions generated by the ionizing source. The electric/magnetic field generator directs ions through the ion transfer section of the peptide analyzer to the ion detector.

Preferably, the peptide analyzer further comprises an ion trap positioned between the ion transfer section of the analyzer and the detector, for performing one or more operations such as ion storage, ion selection and ion collision. The ion trap can be used to fragment ions produced by the ion source (e.g., causing ions to undergo collisional activated dissociation in the presence of a neutral gas ions, such as helium ions). The ion trap also can be used to store ions in stable orbits and to sequentially eject ions based on their mass-to-charge values (m/z) to the detector. An additional separation section can be provided between the ion trap and detector to separate fragments generated in the ion trap (e.g., as in tandem MS). The detector detects the signal strength of each ion (e.g., intensity), which is a reflection of the amount of protonation of the ion.

The peptide analyzer additionally preferably is associated with data system for recording and processing information collected by the detector. The data system can respond to instructions from a processor in communication with the separation system and also can provide data to the processor. Preferably, the data system includes one or more of: a computer; an analog to digital conversion module; and control devices for data acquisition, recording, storage and manipulation. More preferably, the device further comprises a mechanism for data reduction, i.e., a device to transform the initial digital or analog representation of output from the analyzer into a form that is suitable for interpretation, such as a graphical display, a table of masses, a report of abundances of ions, etc.)

The data system can perform various operations such as signal conditioning (e.g., providing instructions to the peptide analyzer to vary voltage, current, and other operating parameters of the peptide analyzer), signal processing, and the like. Data acquisition can be obtained in real time, e.g., at the same time mass data is being generated. However, data acquisition also can be performed after an experiment, e.g., when the mass spectrometer is off line.

The data system can be used to derive a spectrum graph in which relative intensity (i.e., reflecting the amount of protonation of the ion) is plotted against the mass to charge ratio (m/z ratio) of the ion or ion fragment. An average of peaks in a spectrum can be used to obtain the mass of the ion (e.g., peptide) (see, e.g., McLafferty and Turecek, 1993, Interpretation of Mass Spectra, University Science Books, CA).

Mass spectra can be searched against a database of reference peptides of known mass and sequence to identify a reference peptide which matches a test peptide (e.g., comprises a mass which is smaller by the amount of mass attributable to a ubiquitin remnant). The database of standard peptides can be generated experimentally, e.g., digesting non-ubiquitinated peptides and analyzing these in the peptide analyzer. The database also can be generated after a virtual digestion process, in which the predicted mass of peptides is generated using a suite of programs such as PROWL (e.g., available from ProteoMetrics, LLC, New York; N.Y.). A number of database search programs exist which can be used to correlate mass spectra of test peptides with amino acid sequences from polypeptide and nucleotide databases, including, but not limited to: the SEQUEST program (Eng, et al., J. Am. Soc. Mass Spectrum. 5: 976-89; U.S. Pat. No. 5,538,897; Yates, Jr., III, et al., 1996, J. Anal. Chem. 68(17): 534-540A), available from Finnegan Corp., San Jose, Calif.

Data obtained from fragmented peptides can be mapped to a larger peptide or polypeptide sequence by comparing overlapping fragments. Preferably, a Ubiquitinated peptide is mapped to the larger polypeptide from which it is derived to identify the ubiquitination site on the polypeptide. Sequence data relating to the larger polypeptide can be obtained from databases known in the art, such as the nonredundant protein database compiled at the Frederick Biomedical Supercomputing Center at Frederick, Md.

In another aspect of the invention, the amount and location of ubiquitination is compared to the presence, absence and/or quantity of other types of polypeptide modifications. For example, the presence, absence, and/or quantity of phosphorylation, sulfation, glycosylation, and/or acetylation can be determined using methods routine in the art (see, e.g., Rossomando, et al., 1992, Proc. Natl. Acad. Sci. USA 89: 5779-578; Knight et al., 1993, Biochemistry 32: 2031-2035; U.S. Pat. No. 6,271,037). The amount and locations of one or more modifications can be correlated with the amount and locations of ubiquitination sites. Preferably, such a determination is made for multiple cell states.

Knowledge of ubiquitination sites can be used to identify compounds that modulate particular ubiquitinated polypeptides (either preventing or enhancing ubiquitination, as appropriate, to normalize the ubiquitination state of the polypeptide). Thus, in one aspect, the method described above may further comprise contacting a first cell with a compound and comparing ubiquitination sites/amounts identified in the first cell with ubiquitination sites/amounts in a second cell not contacted with the compound. Suitable cells that may be tested include, but are not limited to: neurons, cancer cells, immune cells (e.g., T cells), stem cells (embryonic and adult), undifferentiated cells, pluripotent cells, and the like. In one preferred aspect, patterns of ubiquitination are observed in cultured cells, such as P 19 cells, pluripotent embryonic carcinoma cells capable of differentiating into cardiac cells and skeletal myocytes upon exposure to DMSO (see Montross, et al., J. Cell Sci. 113 (Pt. 10): 1759-70).

Compounds which can be evaluated include, but are not limited to: drugs; toxins; proteins; polypeptides; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers); and combinations thereof. Compounds also can be obtained from synthetic libraries from drug companies and other commercially available sources known in the art (e.g., including, but not limited to the LeadQuest® library) or can be generated through combinatorial synthesis using methods well known in the art. A compound is identified as a modulating agent if it alters the site of ubiquitination of a polypeptide and/or if it alters the amount of ubiquitination by an amount that is significantly different from the amount observed in a control cell (e.g., not treated with compound).

In further aspect of the invention, the ubiquitination states (e.g., sites and amount of ubiquitination) of first and second cells are evaluated. Preferably, the second cell differs from the first cell in expressing one or more recombinant DNA molecules, but is otherwise genetically identical to the first cell. Alternatively, or additionally, the second cell can comprise mutations or variant allelic forms of one or more genes. In one aspect, DNA molecules encoding regulators of the ubiquitin pathway can be introduced into the second cell (e.g., E1, E2, E3, deubiquitinating proteins, fragments thereof, mutant forms thereof, variants, and modified forms thereof, or compounds identified as above) and alterations in the ubiquitination state in the second cell can be determined. DNA molecules can be introduced into the cell using methods routine in the art, including, but not limited to: transfection, transformation, electroporation, electro fusion, microinjection, and germline transfer.

The invention also provides methods for generating a database comprising data files for storing information relating to diagnostic peptide fragmentation signatures. Preferably, data in the data files include one or more peptide fragmentation signatures characteristic or diagnostic of a cell state (e.g., such as a state which is characteristic of a disease, a normal physiological response, a developmental process, exposure to a therapeutic agent, exposure to a toxic agent or a potentially toxic agent, and/or exposure to a condition). Data in the data files also preferably includes values corresponding to level of proteins corresponding to the peptide fragmentation signatures found in a particular cell state.

In one embodiment, for a cell state determined by the differential expression of at least one protein, a data file corresponding to the cell state will minimally comprise data relating to the mass spectra observed after peptide fragmentation of a standard peptide diagnostic of the protein. Preferably, the data file will include a value corresponding to the level of the protein in a cell having the cell state. For example, a tumor cell state is associated with the overexpression of p53 (see, e.g., Kern, et al., 2001, Int. J. Oncol. 21(2): 243-9). The data file will comprise mass spectral data observed after fragmentation of a standard corresponding to a subsequence of p53. Preferably, the data file also comprises a value relating to the level of p53 in a tumor cell. The value may be expressed as a relative value (e.g., a ratio of the level of p53 in the tumor cell to the level of p53 in a normal cell) or as an absolute value (e.g., expressed in nM or as a % of total cellular proteins).

Preferably, the data files also include information relating to the presence or amount of a modified form of a target a polypeptide in at least one cell and to mass spectral data diagnostic of the modified form (i.e., peak data for a fragmented peptide internal standard which corresponds to the modified form). More preferably, the data files also comprise spectral data diagnostic of the unmodified form as well as data corresponding to the level of the unmodified form.

In one embodiment, data relating to ubiquitination sites and amounts of ubiquitination are stored in a database to create a proteome map of ubiquitinated proteins. Preferably, the database comprises a collection of data files relating to all ubiquitinated polypeptides in a particular cell type. The database preferably further comprises data relating to the origin of the cell, e.g., such as data relating to a patient from whom a cell was obtained. More preferably, the database comprises data relating to cells obtained from a plurality of patients. In one aspect, the database comprises data relating to the ubiquitination of a plurality of different cell types (e.g., cells from patients with a pathology, normal patients, cells at various stages of differentiation, and the like). In another aspect, data relating to ubiquitination patterns in cells obtained from patients with a neurological disease are stored in the database. For example, information relating to ubiquitination in cell samples from patients having any of Alzheimer's disease; amyotrophic lateral sclerosis; dementia; depression; Down's syndrome; Huntington's disease; peripheral neuropathy; multiple sclerosis; neurofibromatosis; Parkinson's disease; and schizophrenia, can be included in the database.

In a further embodiment, data relating to ubiquitination patterns in cells from patients with cancer are stored in the database, including, but not limited to patients with: adenocarcinoma; leukemia; lymphoma; melanoma; myeloma; sarcoma; teratocarcinoma; and, in particular, cancers of the adrenal gland; bladder; bone; bone marrow; brain; breast; cervix; gall bladder; ganglia; gastrointestinal; tract; heart; kidney; liver; lung; muscle; ovary; pancreas; parathyroid; prostate; salivary glands; skin; spleen; testes; thymus; thyroid; and uterus.

Additionally, data of ubiquitination patterns in cells from patients with an immune disorder may be included in the database. Such a disorder can include: acquired immunodeficiency syndrome (AIDS); Addison's disease; adult respiratory distress syndrome; allergies; ankylosing spondylitis; amyloidosis; anemia; asthma; atherosclerosis; autoimmune hemolytic anemia; autoimmune thyroiditis; bronchitis; cholecystitis; contact dermatitis; Crohn's disease; atopic dermatitis; dermatomyositis; diabetes mellitus; emphysema; episodic lymphopenia with lymphocytotoxins; erythroblastosis fetalis; erythema nodosum; atrophic gastritis; glomerulonephritis; Goodpasture's syndrome; gout; Graves' disease; Hashimoto's thyroiditis; hypereosinophilia; irritable bowel syndrome; myasthenia gravis; myocardial or pericardial inflammation; osteoarthritis; osteoporosis; pancreatitis; polymyositis; psoriasis; Reiter's syndrome; rheumatoid arthritis; scleroderma; Sjogren's syndrome; systemic anaphylaxis; systemic lupus erythematosus; systemic sclerosis; thrombocytopenic purpura; ulcerative colitis; uveitis; Werner syndrome; and viral, bacterial, fungal, parasitic, protozoal, and helminthic infections.

Data regarding ubiquitination in apoptotic cells and in pathologies associated with the misregulation of apoptosis also can be obtained using methods according to the invention.

In a further embodiment, data regarding ubiquitination in cardiac cells and cells from patients exhibiting a cardiac disease or at risk for a cardiac disease are obtained. In one aspect, the disease is an infarction or a condition relating to ischemia. In another aspect, the disease is cardiomyopathy.

Another aspect of the invention provides for kits for detecting and/or quantifying a polypeptide modification, such as ubiquitination. In one embodiment, the kit comprises a ubiquitin remnant specific binding partner and one or more components, including, but not limited to: a protease, preferably trypsin; a ubiquitinated molecule comprising known ubiquitination sites; acetonitrile; silica resin; heptafluorobutyric acid; urea (e.g., 8M urea); a sample plate for use with a mass spectrometer; a light-absorbent matrix; an ion exchange resin; software for analyzing mass spectra (e.g., such as SEQUEST); fused silica capillary tubing; and access to a computer memory comprising data files storing information relating to ubiquitination sites for a plurality of polypeptides for a plurality of different cells. Access may be in the form of a computer readable program product comprising the memory, or in the form of a URL and/or password for accessing an internet site for connecting a user to such a memory.

EXAMPLES

Example 1

Both polyclonal and monoclonal antibodies capable of recognizing the remnant of ubiquitin left from ubiquitinated proteins after digestion with the protease trypsin were generated. These antibodies were generated using a synthetic peptide library immunogen with the sequence CXXXXXXK (GG)XXXXXX, i.e., a Cysteine residue at the peptide amino-terminus, 6 "X" residues (X=any amino acid selected from all common amino acids excluding cysteine and tryptophan), a lysine residue ("K") that has been modified by addition of a Glycine-Glycine dipeptide to the epsilon-amino group of that lysine residue and 6 more "X" residues.

Polyclonal antibodies were generated by injecting rabbits with the peptide library immunogen described above conjugated either to keyhole limpet hemocyanin (KLH) or blue carrier protein. K(GG)-specific polyclonal antibodies from 6 rabbits: BL3415, BL3416, BL4933, BL4934, BL4935, BL4936.

BL4933, BL4935 were used as starting material for monoclonal antibody development.

A monoclonal antibody from BL4933 was cloned and named recombinant antibody #3925 (D4A7A10). An additional monoclonal antibody was cloned from BL4935 (D24B6G9).

Table 1 shows the different monoclonal and polyclonal anti-ubiquitin remnant antibodies of the invention.

| Monoclonal anti-Ubiquitin Remnant Antibodies | Polyclonal anti-Ubiquitin Remnant Antibodies |
|---|---|
|  | BL3415 |
|  | BL3416 |
| D4A7A10 | BL4933 |
|  | BL4934 |
| D28B6G9 | BL4935 |
|  | BL4936 |

The heavy chain amino acid sequence of the D4A7A10 clone is provided in SEQ ID NO: 1. The light chain amino acid sequence of the D4A7A10 clone is provided in SEQ ID NO: 2. For the D4A7A10 clone (i.e., antibody #3925), using the CDR-defining rules set forth above, the CDR regions for the heavy and light chain are as follows:

```
Heavy Chain:
CDR1
                                    (SEQ ID NO: 3)
GFTISSNYYIYWV

CDR2
                                    (SEQ ID NO: 4)
CIYGGSSGTTLYASWAKG

CDR3
                                    (SEQ ID NO: 5)
DFRGADYSSYDRIWDTRLDL

Light Chain:
CDR1
                                    (SEQ ID NO: 6)
QSSENVYNKNWLS

CDR2
                                    (SEQ ID NOL: 7)
KASTLAS

CDR3
                                    (SEQ ID NO: 8)
AGDYGGTGDAFV
```

The skilled artisan can readily determine the CDRs for the other antibodies disclosed herein including, without limitation, the antibody D24B6G9 cloned from BL4935.

Example 2

Characterization and Screening of Ubiquitin Tag Motif Antibodies. Anti-ubiquitin remnant peptide antibodies were characterized by differential peptide ELISA against antigen peptides CXXXXXXK(GG)XXXXXX (C02-1257) and control peptides CXXXXXXKXXXXXX (173-92A). All antibodies gave strong positive signals with antigen peptides and showed no binding with control peptides. Antibodies were validated by the peptide immunoprecipitation-MS methods described below by identifying ubiquitin-modified peptides in a trypsin-digested Jurkat cell lysate: antibodies passed this validation test when their use resulted in identification of most of the seven known ubiquitination sites in ubiquitin itself. These seven sites are shown in Table 2. Note that the some of the sites are represented in more than one peptide produced by trypsin digestion due to more than one trypsin cleavage sequence near the ubiquitinated site and/or due to more than one ubiquitinatable lysine residue in the peptide. For example, the ubiquitinated site at residue 48 is found in three trypic peptides (see Table 2).

TABLE 2

Known Ubiquitination Sites in Ubiquitin (where the asterisk following the lysing residue (i.e., K*) indicates the ubiquitinated residue)

| Residue Number | Peptide Sequences |
|---|---|
| 6 | MQIFVK*TLTGK (SEQ ID NO: 9) |
| 11 | TLTGK*TITLEVEPSDTIENVK (SEQ ID NO: 10)<br>TLTGK*TITLEVEPSDTIENVKAK (SEQ ID NO: 11) |
| 27 | TITLEVEPSDTIENVK*AKIQDKEGIPPDQQR (SEQ ID NO: 12) |
| 29 | AK*IQDKEGIPPDQQR (SEQ ID NO: 13) AK*IQDK*EGIPPDQQR (SEQ ID NO: 14) |
| 33 | IQDK*EGIPPDQQR (SEQ ID NO: 15)<br>AKIQDK*EGIPPDQQR (SEQ ID NO: 16) AK*IQDK*EGIPPDQQR (SEQ ID NO: 17) |
| 48 | LIFAGK*QLEDGR (SEQ ID NO: 18)<br>LIFAGK*QLEDGRTLSDYNIQK (SEQ ID NO: 19)<br>LIFAGK*QLEDGRTLSDYNIQKESTLHLVLR (SEQ ID NO: 20) |
| 63 | TLSDYNIQK*ESTLHLVLR (SEQ ID NO: 21) |

The antibodies of the invention were designed to recognize any peptide that contains ubiquitinated lysine residues regardless of surrounding peptide sequences. To illustrate the general context-independent recognition properties of one of these antibodies, the heat map shown in FIG. 2 shows the frequency of amino acids found with the BL4936 polyclonal antibody in a study of four mouse tissues. The studies were similar to the study described below in Example 3. Briefly, and by way of example, the cellular proteins are isolated from the tissue and digested with trypsin protease. Peptide purification was carried out, e.g., using Sep-PakC18 columns as described in Rush et al., U.S. Pat. No. 7,300,753). Following purification, peptides are lyophilized and then resuspended in MOPS buffer (50 mM MOPS/NaOH pH 7.2, 10 mM Na$_2$HPO$_4$, 50 mM NaCl) and insoluble material removed by centrifugation at 12,000×g for 10 minutes. The anti-ubiquitin remnant antibodies of the invention were coupled non-covalently to protein G agarose beads (Roche) at 4 mg/ml beads overnight at 4° C. After coupling, antibody-resin was washed twice with PBS and three times with MOPS buffer. Immobilized antibody (40 1[11, 160 iug) was added as a 1:1 slurry in MOPS IP buffer to the solubilized peptide fraction, and the mixture was incubated overnight at 4° C. The immobilized antibody beads were washed three times with MOPS buffer and twice with ddH20. Peptides were eluted twice from beads by incubation with 50 IA of 0.15% TFA for 15 minutes each, and the fractions were combined and analyzed by LC-MS/MS mass spectrometry.

Altogether 1458 non-redundant peptides were included in the frequency map shown in FIG. 2. The map clearly shows there are no strongly preferred amino acids at least seven residues to the amino-terminal side of K(GG) modification sites (−7 to −1 in FIG. 2) or at least seven residues to the carboxyl-terminal side of K(GG) modification sites (1 to 7 in FIG. 2).

Example 3

Numerous experiments were performed using the isolated antibodies of the invention in the methods described in U.S. Pat. Nos. 7,198,896 and 7,300,753. Table 3 lists some of these experiments performed and the number of ubiquitinated peptides observed (both redundant and non-redundant) in each of these experiments.

TABLE 3

| Expt | Antibody | Cell/Tissue Type | Treatment 1 | Treatment 2 | Redundant | Non-Redundant |
|---|---|---|---|---|---|---|
| 3114 | BL4936 | mouse heart | | | 447 | 332 |
| 3115 | BL4936 | mouse liver | | | 790 | 591 |
| 3116 | BL4936 | Embryo mouse | | | 662 | 548 |
| 3117 | BL4936 | Adult mouse brain | | | 735 | 565 |
| 3573 | BL4936 | rat brain sham | mock surgery | | 738 | 553 |
| 3574 | BL4936 | rat brain sham | mock surgery | | 833 | 618 |
| 3575 | BL4936 | rat brain ischemia 30 R | ischemia | Reperfusion | 760 | 554 |
| 3576 | BL4936 | rat brain ischemia 30' R | ischemia | Reperfusion | 809 | 580 |
| 3577 | BL4936 | rat brain ischemia 24 h R | ischemia | Reperfusion | 741 | 551 |
| 3578 | BL4936 | rat brain ischemia 24 h R | ischemia | Reperfusion | 773 | 567 |
| 3970 | BL4936 | rat brain sham | untreated | | 693 | 499 |
| 3971 | BL4936 | rat brain ischemia 30' R | Reperfusion | | 829 | 604 |
| 3972 | BL4936 | rat brain ischemia 24 h R | Reperfusion | | 816 | 620 |
| 4120 | BL4934 | AD control | untreated | | 413 | 271 |
| 4121 | BL4934 | AD control | untreated | | 382 | 249 |
| 4122 | BL4934 | AD control | untreated | | 388 | 265 |
| 4123 | BL4934 | AD control | untreated | | 488 | 326 |
| 4124 | BL4934 | AD control | untreated | | 406 | 278 |
| 4125 | BL4934 | AD control | untreated | | 478 | 321 |
| 4126 | BL4934 | AD+/− | untreated | | 453 | 324 |
| 4127 | BL4934 | AD+/− | untreated | | 508 | 343 |
| 4128 | BL4934 | AD+/− | untreated | | 384 | 258 |
| 4129 | BL4934 | AD+/− | untreated | | 265 | 181 |
| 5338 | BL4934 | Jurkat | pervanadate | calyculin | 217 | 173 |
| 5339 | BL4936 | Jurkat | pervanadate | calyculin | 202 | 161 |
| 5566 | BL4934 | MKN-45 | Su11274 | | 668 | 394 |
| 5567 | BL4934 | MKN-45 | Su11274 | | 565 | 353 |
| 5642 | BL4933 | H2228 silac1 | DMSO | | 615 | 408 |
| 5643 | BL4933 | H2228 silac2 | inhibitor | | 556 | 326 |
| 5644 | BL4933 | H2228 silac3 | inhibitor | | 463 | 298 |
| 5645 | BL4933 | H2228 silac4 | inhibitor | | 415 | 272 |
| 5712 | D24B6G | Jurkat | pervanadate | calyculin | 137 | 105 |
| 5972 | BL49 | H3122 Silac | inhibitor | | 353 | 200 |
| 5973 | BL49 | H3122 Silac | inhibitor | | 247 | 185 |
| 5974 | BL49 | H3122 Silac | inhibitor | | 391 | 245 |
| 6090 | BL49 | H2228 silac Dana Farber | inhibitor | | 193 | 135 |
| 6093 | BL49 | H3122 Silac Dana Farber | inhibitor | | 178 | 140 |
| 6131 | BL49 | H1703 | normal | | 978 | 691 |
| 6362 | D24B | Jurkat | pervanad | calyculin | 431 | 283 |
| 6586 | BL49 | U266 | control | | 793 | 539 |
| 6587 | BL49 | U266 | MG132 | | 791 | 522 |
| 6588 | BL49 | U266 | MG132 | | 1074 | 867 |
| 6589 | BL49 | H929 | control | | 1265 | 764 |
| 6590 | BL49 | H929 | MG132 | | 712 | 468 |
| 6591 | BL49 | H929 | MG132 | | 551 | 467 |
| 6846 | BL49 | H1703 | | | 735 | 484 |
| 6847 | BL49 | H1703 | | | 1143 | 841 |
| 6916 | BL49 | RAW 264.7 | normal | | 1366 | 736 |
| 6917 | BL49 | RAW 264.7 | LPS | | 1396 | 746 |
| 6918 | BL49 | RAW 264.7 | LPS | | 1424 | 771 |
| 6919 | BL49 | RAW 264.7 | MG132 | | 1473 | 871 |
| 6939 | D4A7 | Jurkat | pervanad | calyculin | 286 | 240 |
| 6941 | BL49 | Jurkat | pervanad | calyculin | 130 | 102 |
| 8149 | D4A7 | Jurkat | calyculin | pervanad | 613 | 445 |
| 8158 | D4A7 | mouse muscle | untreated | | 886 | 651 |
| 8159 | D4A7 | mouse spleen | untreated | | 1355 | 1033 |
| 8160 | D4A7 | mouse testis | untreated | | 1096 | 872 |
| 8161 | D4A7 | mouse thymus | untreated | | 827 | 623 |
| 8241 | D4A7 | LNCaP | control | | 940 | 801 |
| 8242 | D4A7 | LNCaP | AAG | | 978 | 826 |
| 8243 | D4A7 | LNCaP | AAG | | 561 | 474 |
| 8244 | D4A7 | LNCaP | | Geldanamycin | 874 | 747 |
| 8245 | D4A7 | LNCaP | | Geldanamycin | 665 | 569 |
| 8246 | D4A7 | LNCaP | | Velcade | | 970 |
| 8247 | D4A7 | LNCaP | | Velcade | | 1056 |

The exemplary results shown below in Table 4 correspond to experiment number 3115 in Table 3. In the experiment, cellular proteins from 500 mg of mouse liver were denatured with urea, reduced with dithiothreitol, alkylated with iodoacetamide digested with the protease trypsin. The resulting peptides were separated from other cellular materials by reversed-phased solid phase extraction, then lyophilized and resuspended. Peptides containing the K(GG) modification were separated from other peptides by treatment with the immobilized polyclonal anti-ubiquitin remnant antibody BL4936. The BL4936 associated beads were washed, and bound K(GG)-peptides were eluted with dilute trifluouroacetic acid. The peptides were concentrated and then analyzed by liquid chromatography-tandem mass spectrometry LC-MS. See for example, U.S. Pat. Nos. 7,198,896 and 7,300,753, the entire disclosures of which are incorporated by reference.

TABLE 4

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 1 | Unassigned | ADRM1 | %34 | MSLK*GTTVTPDKRK | 22 |
| 2 | Unassigned | ADRM1 | %34 | MSLK*GTTVTPDKR | 23 |
| 3 | Unassigned | ADRM1 | %34 | MSLK*GTTVTPDK | 24 |
| 4 | Unassigned | ADRM1 | %34 | M#SLK*GTTVTPDKR | 25 |
| 5 | Unassigned | ADRM1 | %34 | M#SLK*GTTVTPDKRK | 26 |
| 6 | Receptor, channel, transporter or cell surface protein | GLT1 | %517 | MQEDIEMTK*TQSIYDDKNHR | 27 |
| 7 | Chromatin, DNA-binding, DNA repair or DNA replication protein | H1D; H1C | %45; %46 | KASGPPVSELITK*AVAASK | 28 |
| 8 | Chromatin, DNA-binding, DNA repair or DNA replication protein | H1D; H1E; H1C; H1T | %63; %63; %64; %66 | K*ALAAAGYDVEK | 29 |
| 9 | Chromatin, DNA-binding, DNA repair or DNA replication protein | H1D; H1E; H1C; H1T | %63; %63; %64; %66 | K*ALAAAGYDVEKNNSR | 30 |
| 10 | Chromatin, DNA-binding, DNA repair or DNA replication protein | H1D; H1E; H1C; H1T | %74; %74; %75; %77 | ALAAAGYDVEK*NNSR | 31 |
| 11 | Chromatin, DNA-binding, DNA repair or DNA replication protein | H1E | %45 | KTSGPPVSELITK*AVAASK | 32 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 12 | Chromatin, DNA-binding, DNA repair or DNA replication protein | H1E | %45 | TSGPPVSELITK*AVAASK | 33 |
| 13 | Chromatin, DNA-binding, DNA repair or DNA replication protein | H2A.1; H2A0; H2AE | %119; %118; %119 | VTIAQGGVLPNIQAVLLPK*KTESHH K | 34 |
| 14 | Chromatin, DNA-binding, DNA repair or DNA replication protein | H2A.1; H2A0; H2AE | %120; 119; %120 | VTIAQGGVLPNIQAVLLPKK*TESHH K | 35 |
| 15 | Chromatin, DNA-binding, DNA repair or DNA replication protein | H2A.1; H2AX; HIST2H2AB; HIST2H2AC; H2A0; H2A.4; H2AE; H2AL; H2AFJ | %119; %118; 19; 119; %118; %119; %119; %119; %119 | VTIAQGGVLPNIQAVLLPK* K | 36 |
| 16 | Chromatin, DNA-binding, DNA repair or DNA replication protein | H2A.1; H2AX; HIST2H2AB; HIST2H2AC; H2A0; H2A.4; H2AE; H2AL; H2AFJ | %120; %119; 120; 120; 119; 120; %120; %120; %120 | VTIAQGGVLPNIQAVLLPKK * | 37 |
| 17 | Unassigned | H2AE | %120 | VTIAQGGVLPNIQAVLLPKK *TESHH KPK | 38 |
| 18 | Chromatin, DNA-binding, DNA repair or DNA replication protein | H2AFJ | %119 | VTIAQGGVLPNIQAVLLPK*KTESQK | 39 |
| 19 | Chromatin, DNA-binding, DNA repair or DNA | H2AFJ | %120 | VTIAQGGVLPNIQAVLLPKK | 40 |
| 20 | Chromatin, DNA-binding, DNA repair or DNA | H2AFY | %116 | GVTIASGGVLPNIHPELLAK* | 41 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 21 | Chromatin, DNA-binding, DNA repair or DNA | H2AFY | %116 | GVTIASGGVLPNIHPELLAK* | 42 |
| 22 | Chromatin, DNA-binding, DNA repair or DNA replication protein | H2AFY | %117 | GVTIASGGVLPNIHPELLAKK*R | 3 |
| 23 | Chromatin, DNA-binding, DNA repair or DNA replication protein | H2AL | %120 | VTIAQGGVLPNIQAVLLPKK*TETHH K | 4 |
| 24 | Chromatin, DNA-binding, DNA repair or DNA replication protein | H2AX | %119 | K*SSATVGPK | 5 |
| 25 | Chromatin, DNA-binding, DNA repair or DNA replication protein | H2AX; HIST2H2AB | %118; 119 | LLGGVTIAQGGVLPNIQAVLLPK*K | 46 |
| 26 | Chromatin, DNA-binding, DNA repair or DNA replication protein | H2AX; HIST2H2AB | %118; 119 | NDEELNKLLGGVTIAQGGVLPNIQAVLLPK*K | 47 |
| 27 | Chromatin, DNA-binding, DNA repair or DNA replication protein | H2B; H2B1D; H2B1A; H2B1N; H2B2E; H2B1H; H2B1C; Hist3h2ba | %120; %120; %122; %121; %121; %121; %121; %121 | AVTK*YTSSK | 48 |
| 28 | Chromatin, DNA-binding, DNA repair or DNA replication protein | H2B; H2B1D; H2B1A; H2B1N; H2B2E; H2B1L; H2B1H; H2B1C; Hist3h2ba | %46; %46; %48; %47; %47; %47; %47; %47; %47 | VLK*QVHPDTGISSK | 49 |

TABLE 4-continued

Known and Novel Ubiquitination Sites Found in One Analysis of
Proteins 15 from Mouse Liver

| Row | Protein Type | Protein | Ubiquitinated Residue | Peptide Sequence | SEQ ID NO: |
|---|---|---|---|---|---|
| 29 | Chromatin, DNA-binding, DNA repair or DNA replication protein | H2B; H2B1D; H2B1A; H2B1N; H2B2E; H2B1L; H2B1H; H2B1C; Hist3h2ba | %116; %116; %118; %117; %117; %117; %117; %117; %117 | HAVSEGTK*AVTK | 50 |
| 30 | Chromatin, DNA-binding, DNA repair or DNA replication protein | H2B1L | %121 | AVTK*YTSAK | 51 |
| 31 | Unassigned | HIST2H2AB; HIST2H2AC; H2A.4 | 119; 119; %119 | VTIAQGGVLPNIQAVLLPK*KTESHK | 52 |
| 32 | Unassigned | HIST2H2AB; HIST2H2AC; H2A.4 | 125; 125; %125 | VTIAQGGVLPNIQAVLLPKKTESHK* | 53 |
| 33 | Chaperone | HSC70; HSPA1L; HSPA2; HSP70-2; HSP70 | 507; 509; 510; 507; %507 | ITITNDK*GR | 54 |
| 34 | Ubiquitin conjugating system | NEDD8 | %48 | LlYSGK*QMNDEK | 55 |
| 35 | Unassigned | RPS20 | %8 | DTGK*TPVEPEVAIHR | 56 |
| 36 | Unknown function | SPG20 | %360 | SSHPSEPPK*EASGTDVR | 57 |
| 37 | Protein kinase, Ser/Thr (non-receptor) | Titin | %30428 | EAFSSVIIK*EPQIEPTADLTGITNQLITCK | 58 |
| 38 | Cytoskeletal protein | TUBA1B; TUBA3D; TUBA4A; TUBA1A; TUBA1C; TUBA8; TUBA3C | %370; 370; 370; 370; 370; 370; 369 | VGINYQPPTVVPGGDLAK*VQR | 59 |
| 39 | Ubiquitin conjugating system | UBA52; ubiquitin | 11; %11 | TLTGK*TITLEVEPSDTIENV K | 60 |
| 40 | Ubiquitin conjugating system | UBA52; ubiquitin; L0C388720 | 6; %6; 6 | MQIFVK*TLTGK | 61 |
| 41 | Ubiquitin conjugating system | UBA52; ubiquitin; L0C388720; Gm7866 | 29; %29; 29; 106 | AK*IQDKEGIPPDQQR | 62 |

TABLE 4-continued

Known and Novel Ubiquitination Sites Found in One Analysis of
Proteins 15 from Mouse Liver

| Row | Protein Type | Protein | Ubiquitinated Residue | Peptide Sequence | SEQ ID NO: |
|---|---|---|---|---|---|
| 42 | Ubiquitin conjugating system | UBA52; ubiquitin; L0C388720; Gm7866 | 29, 33; %29, %33; 29, 33; 106, 110 | AK*IQDK*EGIPPDQQR | 63 |
| 43 | Ubiquitin conjugating system | UBA52 ubiquitin; L0C388720; Gm7866 | 33; %33; 33; 110 | IQDK*EGIPPDQQR | 64 |
| 44 | Ubiquitin conjugating system | UBA52; ubiquitin; L0C388720; Gm7866 | 33; %33; 33; 110 | AKIQDK*EGIPPDQQR | 65 |
| 45 | Ubiquitin conjugating system | UBA52; ubiquitin; L0C388720; Gm7866 | 48; %48; 48; 125 | LIFAGK*QLEDGR | 66 |
| 46 | Ubiquitin conjugating system | UBA52; ubiquitin; L0C388720; Gm7866 | 48; %48; 48; 125 | LIFAGK*QLEDGRTLSDYNIQK | 67 |
| 47 | Ubiquitin conjugating system | UBA52; ubiquitin; L0C388720; Gm7866 | 48; %48; 48; 125 | LIFAGK*QLEDGRTLSDYNIQKESTL HLVLR | 68 |
| 48 | Ubiquitin conjugating system | UBA52; ubiquitin; L0C388720; OTTMUSGOO 000001634; Gm7866 | 63; %63; 63; 140 | TLSDYNIQK*ESTLHLVLR | 69 |
| 49 | Mitochondrial protein | 1190003J15 Rik | 67 | CPGLLTPSQIKPGTYK*LFFDTER | 70 |
| 50 | Unassigned | 1300002K09 Rik | 223 | SM#LEAHQAKHVK*QLLSKPR | 71 |
| 51 | Adaptor/ scaffold | 14-3-3 eta; 14-3-3 gamma; 14-3-3 zeta; 14-3-3 beta | 49; 49; 49; 50 | NLLSVAYK*NVVGAR | 72 |
| 52 | Enzyme, misc. | 1-Cys PRX | 198 | KGESVM#VVPTLSEEEAK*QCFPK | 73 |
| 53 | Enzyme, misc. | 1-Cys PRX | 198 | KGESVMVVPTLSEEEAK*QCFPK | 74 |
| 54 | Enzyme, misc. | 1-Cys PRX | 208 | GVFTK*ELPSGK | 75 |
| 55 | Receptor, channel, transporter or cell surface protein | ABCA3 | 503 | TVVGK*EEEGSDPEK | 76 |
| 56 | Receptor, channel, transporter or cell surface protein | ABCA3 | 503, 512 | TVVGK*EEEGSDPEK*ALR | 77 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 57 | Receptor, channel, transporter or cell surface protein | ABCA3 | 1620 | SEGK*QDALEEFK | 78 |
| 58 | Unassigned | ABCB11 | 935 | EILEK*AGQITNEALSNIR | 79 |
| 59 | Unassigned | ABCB11 | 935 | MLTGFASQDKEILEK*AGQITNEAL SNIR | 80 |
| 60 | Unassigned | ABCB11 | 935 | M#LTGFASQDKEILEK*AGQITNEAL SNIR | 81 |
| 61 | Receptor, channel, transporter or cell surface protein | ABCC2 | 491 | KIQVQNM#K*NK | 82 |
| 62 | Receptor, channel, transporter or cell surface protein | ABCC2 | 491 | IQVQNMK*NK | 83 |
| 63 | Adhesion or extracellular matrix protein | ABHD2 | 57 | FLLK*SCPLLTK | 84 |
| 64 | Translation | AC078817.18-1; RPL26 | 136; 136 | GKYK*EETIEK | 85 |
| 65 | Enzyme, misc. | ACAA1b; ACAA1 | 292; 292 | RSK*AEELGLPILGVLR | 86 |
| 66 | Enzyme, misc. | ACOX1 | 488 | IQPQQVAVWPTLVDINSLDSLTEAY K*LR | 87 |
| 67 | Enzyme, misc. | ACSL5 | 361 | VYDK*VQNEAK | 88 |
| 68 | Enzyme, misc. | ACSL5 | 616 | NQCVK*EAILEDLQK | 89 |
| 69 | Enzyme, misc. | ACSL5 | 675 | FFQTQIK*SLYESIEE | 90 |
| 70 | Cytoskeletal protein | ACTG2; ACTC1; ACTA1; ACTB; ACTBL2; ACTG1 | 193; 193; 193; 191; 192; 195 | DLTDYLMK*ILTER | 91 |
| 71 | Cytoskeletal protein | ACTG2; ACTC1; ACTA1; ACTB; ACTG1 | 328; 328; 328; 326; 330 | EITALAPSTM#K1K | 92 |
| 72 | Enzyme, misc. | ADCY3 | 297 | HVADEMLKDMKK* | 93 |
| 73 | Mitochondrial protein | ADH1C | 40 | IK*MVATGVCR | 94 |
| 74 | Mitochondrial protein | ADH1C | 105 | ICK*HPESNFCSR | 95 |
| 75 | Mitochondrial protein | ADH1C | 169 | IDGASPLDK*VCLIGCGFSTGYGSA VK | 96 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 76 | Mitochondrial protein | ADH1C | 186 | IDGASPLDKVCLIGCGFSTGYGSAVK*VAK | 97 |
| 77 | Mitochondrial protein | ADH1C | 316 | TWK*GAIFGGFK | 98 |
| 78 | Mitochondrial protein | ADH1C | 339 | LVADFMAK*K | 99 |
| 79 | Kinase (non-protein) | ADK | 110 | AATFFGCIGIDK*FGEILK | 100 |
| 80 | Kinase (non-protein) | ADK | 255 | EQGFETK*DIK | 101 |
| 81 | Kinase (non-protein) | ADK | 357 | TGCTFPEK*PDFH | 102 |
| 82 | Enzyme, misc. | AKR1C1 | 225 | EK*QWVDQSSPVLLDNPVLGSMAK | 103 |
| 83 | Enzyme, misc. | AKR1C1 | 312 | YISGSSFK*DHPDFPFWDEY | 104 |
| 84 | Enzyme, misc. | ALAD | 87 | VPK*DEQGSAADSEDSPTIEAVR | 105 |
| 85 | Enzyme, misc. | ALAD | 87 | CVLIFGVPSRVPK*DEQGSAADSED SPTIEAVR | 106 |
| 86 | Enzyme, misc. | ALAD | 184 | AALLK*HGLGNR | 107 |
| 87 | Receptor, channel, transporter or cell surface protein | albumin | 460 | VGTK*CCTLPEDQR | 108 |
| 88 | Unassigned | ALDH16A1 | 603 | RK*PVLTSQLER | 109 |
| 89 | Enzyme, misc. | ALDH1A1 | 434 | ANNTTYGLAAGLFTK*DLD K | 110 |
| 90 | Enzyme, misc. | ALDH1A1 | 434 | RANNTTYGLAAGLFTK*DL | 111 |
| 91 | Enzyme, misc. | ALDH1A2 | 338 | IFVEESIYEEFVK* | 112 |
| 92 | Unassigned | Aldh1a7 | 435 | ANNTTYGLAAGVFTK*DLD | 113 |
| 93 | Unassigned | Aldh1a7 | 499 | TVAMQISQK*NS | 114 |
| 94 | Enzyme, misc. | Aldh1a7; ALDH1A | 91; 90 | LLNK*LADLMERDR | 115 |
| 95 | Enzyme, misc. | Aldh1a7; ALDH1A | 91; 90 | LLNK*LADLMER | 116 |
| 96 | Enzyme, misc. | Aldh1a7; ALDH1A | 255; 254 | LIK*EAAGK | 117 |
| 97 | Enzyme, misc. | Aldh1a7; ALDH1A | 378; 377 | WGNK*GFFVQPTVFSNVTD | 118 |
| 98 | Enzyme, misc. | Aldh1a7; ALDH1A | 378; 377 | WGNK*GFFVQPTVFSNVTD | 119 |
| 99 | Enzyme, misc. | Aldh1a7; ALDH1A | 398; 397 | IAK*EEIFGPVQQIMK | 120 |
| 100 | Enzyme, misc. | ALDH3A2 | 296 | LQSLLK*GQK | 121 |
| 101 | Enzyme, misc. | ALDH7A1 | 424 | FQDEEEVFEWNNEVK*QGLSSSIFT K | 122 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 102 | Enzyme, misc. | ALDOB | 47 | IK*VENTEENRR | 123 |
| 103 | Enzyme, misc. | ALDOB | 107 | GIVVGIK*LDQGGAPLAGTN | 124 |
| 104 | Enzyme, misc. | ALDOB | 107 | GIVVGIK*LDQGGAPLAGTN KETTIQ GLDGLSER | 125 |
| 105 | Enzyme, misc. | ALDOB | 120 | LDQGGAPLAGTNK*ETTIQG LDGLS ER | 126 |
| 106 | Enzyme, misc. | ALDOB | 329 | ATQEAFMK*R | 127 |
| 107 | Adhesion or extracellular matrix protein | AMFR | 573 | FSK*SADER | 128 |
| 108 | Adhesion or extracellular matrix protein | AMFR | 600 | FLNK*SSEDDGASER | 129 |
| 109 | Calcium-binding protein | ANXA6 | 477 | AINEAYK*EDYHK | 130 |
| 110 | Unassigned | Apoc1 | 60 | AAIEHIK*QK | 131 |
| 111 | Unassigned | ApoE | 105 | LGK*EVQAAQAR | 132 |
| 112 | Unassigned | ApoE | 252 | SK*MEEQTQQIR | 133 |
| 113 | Unassigned | APOL3 | 232 | GMK*EVLDQSGPR | 134 |
| 114 | Unassigned | Apol9b | 184 | IVNK*IPQATR | 135 |
| 115 | Enzyme, misc. | ARG1 | 26 | GGVEK*GPAALR | 136 |
| 116 | Enzyme, misc. | ARG1 | 205 | YFSMTEVDK*LGIGK | 137 |
| 117 | Unassigned | ARIH1 | 314 | QFCFNCGENWHDPVK*CK | 138 |
| 118 | Enzyme, misc. | ASL | 43 | HLWNVDVQGSK*AYSR | 139 |
| 119 | Endoplasmic reticulum or golgi | ASS1 | 112 | EGAK*YVSHGATGK | 140 |
| 120 | Endoplasmic reticulum or golgi | ASS1 | 121 | YVSHGATGK*GNDQVR | 141 |
| 121 | Endoplasmic reticulum or golgi | ASS1 | 340 | HCIQK*SQERVEGK | 142 |
| 122 | Endoplasmic reticulum or golgi | ASS1 | 340 | HCIQK*SQER | 143 |
| 123 | Chromatin, DNA-binding, DNA repair or DNA | ASXL2 | 325 | KVELWK*EQFFENYYGOSS LSLE DSQK | 144 |
| 124 | Unknown function | AUP1 | 250 | VQQLVAK*ELGQIGTR | 145 |
| 125 | Unknown function | BAT3 | 56 | EH IAASVSIPSEK*QR | 146 |
| 126 | Unassigned | BC066028 | 365, 368 | THGRAK*SYK*CGECGK | 147 |

TABLE 4-continued

Known and Novel Ubiquitination Sites Found in One Analysis of
Proteins 15 from Mouse Liver

| Row | Protein Type | Protein | Ubiquitinated Residue | Peptide Sequence | SEQ ID NO: |
|---|---|---|---|---|---|
| 127 | Transcriptional regulator | BCoR-like 1; BCoR | 1491; 1464 | LIVNK*NAGETLLQR | 148 |
| 128 | Enzyme, misc. | BHMT; BHMT2 | 283; 274 | WDIQK*YAR | 149 |
| 129 | Ubiquitin conjugating system | BRAP | 380 | LVASK*TDGK | 150 |
| 130 | Unassigned | C4orf34 | 83 | GSSLPGK*PSSPHSGQDPPAPPVD | 151 |
| 131 | Enzyme, misc. | CA3 | 39 | D I K*H DPSLQPWSASYDPGSAK | 152 |
| 132 | Enzyme, misc. | CA3 | 57 | D I KH DPSLQPWSASYDPGSAK*TIL NNGK | 153 |
| 133 | Endoplasmic reticulum or golgi | catalase | 242 | TDQGIK*NLPVGEAGR | 154 |
| 134 | Enzyme, misc. | CBS | 386 | FLSDK*WMLQK | 155 |
| 135 | Chaperone | CCT-alpha | 126 | LACK*EAVR | 156 |
| 136 | Chaperone | CCT-alpha | 541 | DDK*HGSYENAVHSGALDD | 157 |
| 137 | Chaperone | CCT-theta | 533 | VDQIIMAKPAGGPK*PPSGK DWD DDQND | 158 |
| 138 | Chaperone | CCT-theta | 538 | PAGGPKPPSGK*KDWDDDQ | 159 |
| 139 | Chaperone | CCT-theta | 539 | VDQIIMAKPAGGPKPPSGKK DWD DDQND | 160 |
| 140 | Unassigned | CHIC1 | 179 | SIQK*LLEWENNR | 161 |
| 141 | Unknown function | CIRH1A | 642, 645, 648 | RTTHGFK*MSK*IYK* | 162 |
| 142 | Cytoskeletal protein | claudin 3 | 216 | STGPGTGTGTAYDRK*DYV | 163 |
| 143 | Unassigned | CLIC4 | 202 | LH IVKVVAK* | 164 |
| 144 | Vesicle | CLTC | 629 | AH IAQLCEK*AGLLQR | 165 |
| 145 | Vesicle | CLTC | 1450 | AVNYFSK*VK | 166 |
| 146 | Vesicle | CLTC | 1452 | VK*QLPLVKPYLR | 167 |
| 147 | Mitochondrial protein | CPS1 | 307 | EPLFG ISTGN I ITG LAAGAK*SYK | 168 |
| 148 | Mitochondrial protein | CPS1 | 310 | SYK*MSMANR | 169 |
| 149 | Mitochondrial protein | CPS1 | 560 | QLFSDKLNEINEK*IAPSFAVE SMED ALK | 170 |
| 150 | Mitochondrial protein | CPS1 | 772 | TSACFEPSLDYMVTK*IPR | 171 |
| 151 | Mitochondrial protein | CPS1 | 1100 | SIFSAVLDELK*VAQAPWK | 172 |
| 152 | Mitochondrial protein | CPS1 | 1183 | EVEMDAVGK*EGR | 173 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 153 | Mitochondrial protein | CPS1 | 1269 | SFPFVSK*TLGVDFIDVATK | 174 |
| 154 | Enzyme, misc. | CPT1A | 195 | YLESVRPLMK*EGDFQR | 175 |
| 155 | Enzyme, misc. | CRAD2 | 64 | VLAACLTEK*GAEQLR | 176 |
| 156 | Enzyme, misc. | CRAD2 | 224 | LSHSIEK*LWDQTSSEVKEV YDKNF LDSYIK | 177 |
| 157 | Cell cycle regulation | CTH | 47 | AVVLPISLATTFK*QDFPGQS SGFE YSR | 178 |
| 158 | Cell cycle regulation | CTH | 72 | NCLEK*AVAALDGAK | 179 |
| 159 | Adhesion or extracellular matrix protein | CTNNB1 | 671 | M#SEDKPQDYK*K | 180 |
| 160 | Adhesion or extracellular matrix protein | CTNNB1 | 671 | MSEDKPQDYK*K | 181 |
| 161 | Adaptor/scaffold | CTNND1 | 517 | MEIVDHALHALTDEVIIPHS GWERE PNEDCK*PR | 182 |
| 162 | Adaptor/scaffold | CTNND1 | 517 | M#EIVDHALHALTDEVIIPHS GWER EPNEDCK*PR | 183 |
| 163 | Adaptor/scaffold | CTNND1 | 710 | SALRQEK*ALSAIAELLTSEH ER | 184 |
| 164 | Receptor, channel, transporter or cell surface protein | Cx32 | 244 | LSPEYK*QNEINK | 185 |
| 165 | Receptor, channel, transporter or cell surface protein | Cx32 | 276 | SPGTGAGLAEK*SDR | 186 |
| 166 | Receptor, channel, transporter or cell surface protein | Cx32 | 276 | RSPGTGAGLAEK*SDR | 187 |
| 167 | Adhesion or extracellular matrix protein | CXADR | 271 | YEK*EVHHDIR | 188 |
| 168 | Unassigned | CYB5A | 38 | VYDLTK*FLEEHPGGEEVLR | 189 |
| 169 | Enzyme, misc. | CYB5R3 | 240 | LWYTVDK*APDAWDYSQG FVNEE M#IR | 190 |
| 170 | Enzyme, misc. | CYP1A1; CYP1A2 | 97; 94 | IGSTPVVLSGLNTIK*QALV R | 191 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 171 | Enzyme, misc. | CYP1A2 | 250 | YLPNPALK*R | 192 |
| 172 | Enzyme, misc. | CYP1A2 | 276 | TVQEHYQDFNK*NSIQDITSALFK | 193 |
| 173 | Enzyme, misc. | CYP1A2 | 294 | HSENYK*DNGGLIPEEK | 194 |
| 174 | Enzyme, misc. | CYP1A2 | 401 | DTSLNGFHIPK*ER | 195 |
| 175 | Enzyme, misc. | Cyp2a12 | 250 | DSHKLEDFMIQK*VK | 196 |
| 176 | Enzyme, misc. | Cyp2a12 | 252 | VK*QNQSTLDPNSPR | 197 |
| 177 | Endoplasmic reticulum or golgi | CYP2A7 | 32 | LSGK*LPPGPTPLPFVGNFLQLNTE QM#YNSLM#K | 198 |
| 178 | Endoplasmic reticulum or golgi | CYP2A7 | 32 | LSGK*LPPGPTPLPFVGNFLQLNTE QMYNSLM#K | 199 |
| 179 | Endoplasmic reticulum or golgi | CYP2A7 | 32 | LSGK*LPPGPTPLPFVGNFLQLNTE QMYNSLMK | 200 |
| 180 | Endoplasmic reticulum or golgi | CYP2A7; Cyp2a5 | 239; 239 | HLPGPQQQAFK*ELQGLEDFITK | 201 |
| 181 | Endoplasmic reticulum or golgi | CYP2A7; Cyp2a5 | 342; 342 | NRQPK*YEDR | 202 |
| 182 | Endoplasmic reticulum or golgi | CYP2A7; Cyp2a5 | 348; 348 | MK*MPYTEAVIHEIQR | 203 |
| 183 | Endoplasmic reticulum or golgi | CYP2A7; Cyp2a5 | 409; 409 | FFSNPK*DFNPK | 204 |
| 184 | Endoplasmic reticulum or golgi | CYP2A7; Cyp2a5; Cyp2a21-ps | 250; 250; 35 | ELQGLEDFITK*K | 205 |
| 185 | Enzyme, misc. | CYP2B1; Cyp2b9; Cyp2b13 | 346; 345; 345 | TK*MPYTDAVIHEIQR | 206 |
| 186 | Enzyme, misc. | CYP2C19; Cyp2c29; CYP2C9; Cyp2c54; Cyp2c50 | 432; 331; 432; 432; 432 | KSDYFMPFSTGK*R | 207 |
| 187 | Enzyme, misc. | CYP2C19; Cyp2c29; CYP2C9; Cyp2c54; Cyp2c50 | 432; 331; 432; 432; 432 | SDYFMPFSTGK*R | 208 |
| 188 | Enzyme, misc. | CYP2C19; Cyp2c50 | 84; 84 | KPTVVLHGYEAVK*EALVDHGEEFA GR | 209 |
| 189 | Unassigned | Cyp2c29 | 298 | GTTVITSLSSVLHDSK*EFPNPEM# FDPGHFLNGNGNFK | 210 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 190 | Enzyme, misc. | Cyp2c39 | 399 | GTTVVTSLTSVLHDSK*EFP NPELF DPGHFLDANGNFK | 211 |
| 191 | Enzyme, misc. | Cyp2c39; Cyp2c29; CYP2C9 | 270; 169; 270 | DFIDYYLIK*QK | 212 |
| 192 | Enzyme, misc. | Cyp2c40 | 375 | YIDLGPNGVVHEVTCDTK*FR | 213 |
| 193 | Enzyme, misc. | Cyp2c40; LOC100048323 | 110; 110 | GK*GIGFSHGNVWK | 214 |
| 194 | Enzyme, misc. | Cyp2c40; LOC100048323 | 154; 154 | VQEEAQWLM#K*ELKK | 215 |
| 195 | Enzyme, misc. | Cyp2c40; LOC100048323 | 154; 154 | VQEEAQWLMK*ELKK | 216 |
| 196 | Enzyme, misc. | Cyp2c40; LOC100048323 | 154; 154 | VQEEAQWLMK*ELK | 217 |
| 197 | Enzyme, misc. | Cyp2c40; LOC100048323 | 154; 154 | VQEEAQWLM#K*ELK | 218 |
| 198 | Enzyme, misc. | Cyp2c40; LOC100048323 | 157; 157 | VQEEAQWLM#KELK* | 219 |
| 199 | Enzyme, misc. | Cyp2c40; LOC100048323 | 157; 157 | VQEEAQWLMKELK*K | 220 |
| 200 | Enzyme, misc. | Cyp2c40; LOCI000483 23 | 249; 249 | IK*EHEESLDVTNPR | 221 |
| 201 | Enzyme, misc. | Cyp2c54 | 84 | KPTVVLHGYEAVK*EALVD HGDVF AGR | 222 |
| 202 | Unassigned | Cyp2c70 | 234 | FLK*DVTQQK | 223 |
| 203 | Unassigned | Cyp2c70 | 234 | FLK*DVTQQKK | 224 |
| 204 | Unassigned | Cyp2c70 | 252 | HQK*SLDLSNPQDFIDYFLIK | 225 |
| 205 | Unassigned | Cyp2d10 | 414 | GSILIPNM#SSVLKDETVWEK *PLR | 226 |
| 206 | Enzyme, misc. | CYP2D2 | 414 | GTTLIPNLSSVLKDETVWEK* PLR | 227 |
| 207 | Unassigned | Cyp2d40 | 252 | GTTLICNLSSVLKDETVWEK *PLR | 228 |
| 208 | Endoplasmic reticulum or golgi | CYP2E1 | 59 | SLTK*LAK | 229 |
| 209 | Endoplasmic reticulum or golgi | CYP2E1 | 84 | IVVLHGYK*AVK | 230 |
| 210 | Endoplasmic reticulum or golgi | CYP2E1 | 84 | RIVVLHGYK*AVK | 231 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 211 | Endoplasmic reticulum or golgi | CYP2E1 | 87 | AVK*EVLLNHKNEFSGR | 232 |
| 212 | Endoplasmic reticulum or golgi | CYP2E1 | 94 | EVLLNHK*NEFSGR | 233 |
| 213 | Endoplasmic reticulum or golgi | CYP2E1 | 110 | GDIPVFQEYK*NK | 234 |
| 214 | Endoplasmic reticulum or golgi | CYP2E1 | 112 | NK*GlIFNNGPTWK | 235 |
| 215 | Endoplasmic reticulum or golgi | CYP2E1 | 123 | GlIFNNGPTWK*DVR | 236 |
| 216 | Endoplasmic reticulum or golgi | CYP2E1 | 140 | DWGM#GK*QGNEAR | 237 |
| 217 | Endoplasmic reticulum or golgi | CYP2E1 | 140 | DWGMGK*QGNEAR | 238 |
| 218 | Endoplasmic reticulum or golgi | CYP2E1 | 159 | EAHFLVEELK*K | 239 |
| 219 | Endoplasmic reticulum or golgi | CYP2E1 | 162 | TK*GQPFDPTFLIGCAPCNVI ADILF NK | 240 |
| 220 | Endoplasmic reticulum or golgi | CYP2E1 | 255 | AKEHLK*SLDINCPR | 241 |
| 221 | Endoplasmic reticulum or golgi | CYP2E1 | 255 | EHLK*SLDINCPR | 242 |
| 222 | Endoplasmic reticulum or golgi | CYP2E1 | 275 | DVTDCLLIEMEK*EK | 243 |
| 223 | Endoplasmic reticulum or golgi | CYP2E1 | 428 | YSDYFK*AFSAGK | 244 |
| 224 | Endoplasmic reticulum or golgi | CYP2E1 | 428 | YSDYFK*AFSAGKR | 245 |
| 225 | Endoplasmic reticulum or golgi | CYP2E1 | 467 | SLVDPK*DIDLSPVTIGFGSIP R | 246 |
| 226 | Receptor, channel, transporter or cell surface protein | CYP3A4 | 35 | K*QGIPGPTPLPFLGTVLNYY K | 247 |
| 227 | Receptor, channel, transporter or cell surface protein | CYP3A4 | 380 | FCKK*DVELNGVYIPK | 248 |

TABLE 4-continued

Known and Novel Ubiquitination Sites Found in One Analysis of
Proteins 15 from Mouse Liver

| Row | Protein Type | Protein | Ubiquitinated Residue | Peptide Sequence | SEQ ID NO: |
|---|---|---|---|---|---|
| 228 | Receptor, channel, transporter or cell surface protein | CYP3A4 | 425 | ENK*GSIDPYLYMPFGIGPR | 249 |
| 229 | Receptor, channel, transporter or cell surface protein | CYP3A4 | 425 | ENK*GSIDPYLYM#PFGIGPR | 250 |
| 230 | Receptor, channel, transporter or cell surface protein | CYP3A4 | 425 | FSKENK*GSIDPYLYMPFGIGPR | 251 |
| 231 | Receptor, channel, transporter or cell surface protein | CYP3A4 | 477 | VMQNFSFQPCQETQIPLK*LS R | 252 |
| 232 | Receptor, channel, transporter or cell surface protein | CYP3A43; CYP3A5; CYP3A7; UVRAG; KIAA1802; Cyp3a44; CYP3A4 | 421; 422; 422; 558; 657; 422; 422 | FSK*ENK | 253 |
| 233 | Unassigned | Cyp3a44 | 422 | FSK*ENKGSIDPYVYLPFGIGPR | 254 |
| 234 | Unassigned | Cyp3a44 | 488 | QGILQPEK*PIVLK | 255 |
| 235 | Unassigned | Cyp3a44 | 493 | QGILQPEKPIVLK*VVPR | 256 |
| 236 | Receptor, channel, transporter or cell surface protein | Cyp3a44; CYP3A4; L00673748 | 116; 116; 16 | EFGPVGIMSK*AISISKDEEWKR | 257 |
| 237 | Receptor, channel, transporter or cell surface protein | CYP3A5; CYP3A4 | 96; 96 | NVLVK*ECFSVFTNRR | 258 |
| 238 | Receptor, channel, transporter or cell surface protein | CYP3A5; CYP3A4 | 141; 141 | ALLSPTFTSGK*LK | 259 |
| 239 | Receptor, channel, transporter or cell surface protein | CYP3A5; CYP3A4 | 488; 488 | QGLLQPEK*PIVLK | 260 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 240 | Enzyme, misc. | CYP3A5; CYP3A7 | 35; 35 | K*QGIPGPKPLPFLGTVLNYY K | 261 |
| 241 | Enzyme, misc. | CYP3A5; CYP3A7 | 42; 42 | QGIPGPK*PLPFLGTVLNYYK | 262 |
| 242 | Receptor, channel, transporter or cell surface protein | CYP3A5; CYP3A7; CYP3A4 | 96; 96; 96 | NVLVK*ECFSVFTNR | 263 |
| 243 | Enzyme, misc. | CYP3A5; CYP3A7; Cyp3a44 | 158. 158: 158 | LKEM#FPVIEQYGDILVK*YLR | 264 |
| 244 | Enzyme, misc. | CYP3A5; CYP3A7; Cyp3a44 | 158; 158: 158 | EM#FPVIEQYGDILVK*YLR | 265 |
| 245 | Enzyme, misc. | CYP3A5; CYP3A7; Cyp3a44 | 158; 158; 158 | LKEMFPVIEQYGDILVK*YLR | 266 |
| 246 | Receptor, channel, transporter or cell surface protein | CYP3A5; CYP3A7; Cyp3a44; CYP3A4 | 143; 143; 143; 143 | LK*EM#FPVIEQYGDILVK | 267 |
| 247 | Receptor, channel, transporter or cell surface protein | CYP3A5; CYP3A7; Cyp3a44; CYP3A4 | 143; 143; 143; 143 | LK*EMFPVIEQYGDILVK | 268 |
| 248 | Receptor, channel, transporter or cell surface protein | CYP3A5; CYP3A7; Cyp3a44; CYP3A4 | 250; 250; 250; 250 | DSIEFFK*K | 269 |
| 249 | Receptor, channel, transporter or cell surface protein | CYP3A7; CYP3A4 | 59; 59 | GLWK*FDMECYEK | 270 |
| 250 | Endoplasmic reticulum or golgi | CYP4A11 | 252 | LAK*QACQLAHDHTDGVIK | 271 |
| 251 | Enzyme, misc. | CYP51A1 | 436 | YLQDNPASGEK*FAYVPFGAGR | 272 |
| 252 | Enzyme, misc. | CYP51A1 | 436 | LDFNPDRYLQDNPASGEK*F AYVP FGAGR | 273 |
| 253 | Endoplasmic reticulum or golgi | Cyp7a1 | 127 | SIDPSDGNTTENINK*TFNK | 274 |
| 254 | Enzyme, misc. | CYP8B1 | 366 | VVQEDYVLK*MASGQEYQ IR | 275 |
| 255 | Lipid binding protein | DBI | 50 | QATVGDVNTDRPGLLDLK*GK | 276 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 256 | Adhesion or extracellular matrix protein | desmoplakin | 152 | QMGQPCDAYQK*R | 277 |
| 257 | Adhesion or extracellular matrix protein | desmoplakin | 166 | ALYK*AISVPR | 278 |
| 258 | Adhesion or extracellular matrix protein | desmoplakin | 249 | WQLDK*IK | 279 |
| 259 | Enzyme, misc. | Diminuto | 446 | VK*HFEAR | 280 |
| 260 | Unassigned | DNAJA2 | 158 | SGAVQK*CSACR | 281 |
| 261 | Enzyme, misc. | DPYD | 875 | VAELMGQK*LPSFGPYLEQR | 282 |
| 262 | Adhesion or extracellular matrix protein | DSC2 | 838 | LGDK*VQFCHTDDNQK | 283 |
| 263 | Receptor, channel, transporter or cell surface protein | DYSF | 1612 | ISIGK*K | 284 |
| 264 | Translation | eEF-2 | 271 | YFDPANGK*FSK | 285 |
| 265 | Translation | eEF-2 | 274 | FSK*SANSPDGK | 286 |
| 266 | Translation | eIF3C | 860 | TEPTAQQNLALQLAEK*LGSLVENN ER | 287 |
| 267 | Translation | eIF3-theta | 420 | EQPEK*EPELQQYVPQLQNN | 288 |
| 268 | Translation | eIF3-theta | 775 | QSVYEEK*LKQFEER | 289 |
| 269 | Vesicle protein | epsin 1 | 107 | ENMYAVQTLK*DFQYVDR DGKDQ GVNVR | 290 |
| 270 | Enzyme, misc. | esterase D | 17 | CFGGLQK*VFEHSSVELK | 291 |
| 271 | Lipid binding protein | FABP1 | 20 | YQLQSQENFEPFMK*AIGLP EDLIQ K | 292 |
| 272 | Lipid binding protein | FABP1 | 31 | AIGLPEDLIQK*GK | 293 |
| 273 | Lipid binding protein | FABP1 | 36 | GKDIK*GVSEIVHEGK | 294 |
| 274 | Lipid binding protein | FABP1 | 36 | DIK*GVSEIVHEGK | 295 |
| 275 | Lipid binding protein | FABP1 | 46 | GVSEIVHEGK*K | 296 |
| 276 | Lipid binding protein | FABP1 | 80 | VK*AVVKLEGDNK | 297 |

TABLE 4-continued

Known and Novel Ubiquitination Sites Found in One Analysis of
Proteins 15 from Mouse Liver

| Row | Protein Type | Protein | Ubiquitinated Residue | Peptide Sequence | SEQ ID NO: |
|---|---|---|---|---|---|
| 277 | Lipid binding protein | FABP1 | 84 | AVVK*LEGDNK | 298 |
| 278 | Lipid binding protein | FABP1 | 99 | M#VTTFKGIK* | 299 |
| 279 | Receptor, channel, transporter or cell surface protein | FADS2 | 28 | WEEIQK*HNLR | 300 |
| 280 | Receptor, channel, transporter or cell surface protein | FADS2 | 87 | FLK*PLLIGELAPEEPSLDR | 301 |
| 281 | Enzyme, misc. | FAH | 186 | RPMGQMRPDNSK*PPVYGACR | 302 |
| 282 | Enzyme, misc. | FBXL11 | 808 | AKIRGSYLTVTLQRPTK* | 303 |
| 283 | Enzyme, misc. | FDPS | 293 | QILEENYGQK*DPEKVAR | 304 |
| 284 | Enzyme, misc. | FDPS | 297 | QILEENYGQKDPEK*VAR | 305 |
| 285 | Enzyme, misc. | FMO3 | 209 | VLVIGLGNSGCDIAAELSHVAQK*VTISSR | 306 |
| 286 | Enzyme, misc. | Fmo5 | 259 | NNYMEK*QMNQR | 307 |
| 287 | Unassigned | FUND2 | 123 | SK*AEEVVSFVKKNVLVTGGFFGGFLLGMAS | 308 |
| 288 | Apoptosis | G6PI | 226 | TFTTQETITNAETAK*EWFLEAAKDPSAVAK | 309 |
| 289 | Mitochondrial protein | GAPDH; Gm10291; Gm13882; EG622339; L00638833 | 212; 213; 195; 219; 231 | GAAQNIIPASTGAAK*AVGK | 310 |
| 290 | Mitochondrial protein | GAPDH; LOC676923; Gm13882; LOCI00043839; L00638833; L00675602 | 256; 331; 239; 259; 275; 476 | LEKPAKYDDIK*K | 311 |
| 291 | Enzyme, misc. | GDA | 133 | TLK*NGTTTACYFGTIHTDSSLILAEITDKFGQR | 312 |
| 292 | G protein or regulator | G-gamma(12) | 33 | VSK*ASADLMSYCEEHAR | 313 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 293 | Enzyme, misc. | GLUL | 95 | KDPNK*LVLCEVFK | 314 |
| 294 | Enzyme, misc. | GNMT | 96 | YALK*ER | 315 |
| 295 | Enzyme, misc. | GSTA2; GSTA5; GSTA3 | 141; 141; 141 | VLK*SHGQDYLVGNR | 316 |
| 296 | Enzyme, misc. | GSTA3 | 64 | SDGSLM#FQQVPMVEIDGM#K*LVQTK | 317 |
| 297 | Enzyme, misc. | GSTA3 | 64 | SDGSLMFQQVPM#VEIDGM#K*LVQTK | 318 |
| 298 | Enzyme, misc. | GSTA3 | 64 | SDGSLMFQQVPM#VEIDGMK*LVQTK | 319 |
| 299 | Enzyme, misc. | GSTM1 | 198 | ISAYMK*SSR | 320 |
| 300 | Enzyme, misc. | GSTM1; GSTM5; GSTM4 | 51; 51; 52 | FK*LGLDFPNLPYLIDGSHK | 321 |
| 301 | Enzyme, misc. | GSTM1; GSTM5; GSTM4 | 68; 68; 69 | LGLDFPNLPYLIDGSHK*ITQSNAIL R | 322 |
| 302 | Enzyme, misc. | GSTP1 | 127 | ALPGHLK*PFETLLSQNQGG K | 323 |
| 303 | Unassigned | Gstt3 | 218, 229 | AK*DM#PPLMDPALK* | 324 |
| 304 | Enzyme, misc. | Gulo | 332 | AMLEAHPK*VVAHYPVEVR | 325 |
| 305 | Enzyme, misc. | Gulo | 332 | AM#LEAHPK*VVAHYPVEV R | 326 |
| 306 | Chromatin, DNA-binding, DNA repair or DNA replication protein | H1F0 | 59 | SHYK*VGENADSQIK | 327 |
| 307 | Unassigned | H2AE | 126 | VTIAQGGVLPNIQAVLLPKK TESHH K*PK | 328 |
| 308 | Chromatin, DNA-binding, DNA repair or DNA replication protein | H2AX | 127 | KSSATVGPK*APAVGK | 329 |
| 309 | Chromatin, DNA-binding, DNA repair or DNA replication protein | H2B; H2B2E; H2B1C | 5; 6; 6 | PEPAK*SAPAPK | 330 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 310 | Receptor, channel, transporter or cell surface protein | HBA1 | 12 | SNIK*AAWGK | 331 |
| 311 | Receptor, channel, transporter or cell surface protein | HBA1 | 17 | AAWGK*IGGHGAEYGAEALER | 332 |
| 312 | Receptor, channel, transporter or cell surface protein | HBA1 | 41 | M#FASFPTTK*TYFPHFDVSHGSAQ VK | 333 |
| 313 | Receptor, channel, transporter or cell surface protein | HBA1 | 41 | MFASFPTTK*TYFPHFDVSHGSAQ VK | 334 |
| 314 | Receptor, channel, transporter or cell | HBA1 | 57 | TYFPHFDVSHGSAQVK*GHG | 335 |
| 315 | Receptor, channel, transporter or cell surface protein | HBA1 | 91 | VADALASAAGHLDDLPGALSALSD LHAHK*LR | 336 |
| 316 | Receptor, channel, transporter or cell surface protein | HBA1 | 91 | KVADALASAAGHLDDLPGALSALS DLHAHK*LR | 337 |
| 317 | Receptor, channel, transporter or cell surface protein | HBB | 17 | SAVSCLWAK*VNPDEVGGEALGR | 338 |
| 318 | Receptor, channel, transporter or cell | HBB | 59 | YFDSFGDLSSASAIMGNPK* | 339 |
| 319 | Receptor, channel, transporter or cell surface | HBB | 82 | NLDNLK*GTFASLSELHCDKLHVDP ENFR | 340 |
| 320 | Receptor, channel, transporter or cell | HBD | 17 | AAVSCLWGK*VNSDEVGGE | 341 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 321 | Receptor, channel, transporter or cell | HBD | 59 | YFDSFGDLSSASAIM#GNAK* | 342 |
| 322 | Receptor, channel, transporter or cell | HBD | 82 | VITAFNDGLNHLDSLK*GTF ASLSEL HCDKLHVDPENFR | 343 |
| 323 | Enzyme, misc. | HGD | 71 | ILPSVSHK*PFESIDQGHVTH NWDE VGPDPNQLR | 344 |
| 324 | Enzyme, misc. | HGD | 252 | FQGK*LFACK | 345 |
| 325 | RNA processing | hnRNP A/B | 88 | MFVGGLSWDTSK*K | 346 |
| 326 | RNA processing | hnRNP A/B | 89 | MFVGGLSWDTSKK* | 347 |
| 327 | RNA processing | hnRNP A/B | 237 | VAQPK*EVYQQQQYGSGGR | 348 |
| 328 | Enzyme, misc. | HPD | 62 | EVVSHVIK*QGK | 349 |
| 329 | Enzyme, misc. | HPD | 126 | IVREPWVEQDK*FGK | 350 |
| 330 | Enzyme, misc. | HPD | 129 | IVREPWVEQDKFGK*VK | 351 |
| 331 | Enzyme, misc. | HPD | 131 | VK*FAVLQTYGDTTHTLVEK | 352 |
| 332 | Enzyme, misc. | HPD | 131 | IVREPWVEQDKFGKVK* | 353 |
| 333 | Enzyme, misc. | HPD | 236 | SIVVTNYEESIK*MPINEPAPG R | 354 |
| 334 | Enzyme, misc. | HPD | 247 | K*KSQIQEYVDYNGGAGVQ HIALK | 355 |
| 335 | Enzyme, misc. | HPD | 248 | KK*SQIQEYVDYNGGAGVQ HIALK | 356 |
| 336 | Enzyme, misc. | HPD | 269 | SQIQEYVDYNGGAGVQHIAL K*TED IITAIR | 357 |
| 337 | Enzyme, misc. | HPD | 296 | ERGTEFLAAPSSYYK*LLR | 358 |
| 338 | Enzyme, misc. | HPD | 368 | HNHQGFGAGNFNSLFK*AF EEEQA LR | 359 |
| 339 | Enzyme, misc. | HRSP12 | 66 | NLGEILK*AAGCDFNNVVK | 360 |
| 340 | Chaperone | HSC70 | 108 | VQVEYK*GETK | 361 |
| 341 | Chaperone | HSC70 | 512 | LSK*EDIER | 362 |
| 342 | Chaperone | HSC70 | 524 | MVQEAEK*YKAEDEK | 363 |
| 343 | Chaperone | HSC70 | 524 | MVQEAEK*YKAEDEKQR | 364 |
| 344 | Chaperone | HSC70 | 524 | M#VQEAEK*YKAEDEKQR | 365 |
| 345 | Chaperone | HSC70 | 583 | ILDKCNEIISWLDK*NQTAE KEEFEH QQK | 366 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 346 | Chaperone | HSC70 | 583 | ILDKCNEIISWLDK*NQTAE KEEFEH QQKELEK | 367 |
| 347 | Chaperone | HSC70; HSPA2 | 345; 348 | IPK*IQK | 368 |
| 348 | Endoplasmic reticulum or golgi | HSD11B1 | 73 | SEEGLQK*VVSR | 369 |
| 349 | Receptor, channel, transporter or cell surface protein | IFITM3 | 24 | IK*EEYEVAEMGAPHGSASVR | 370 |
| 350 | Receptor, channel, transporter or cell surface protein | IFITM3 | 24 | IK*EEYEVAEM#GAPHGSASVR | 371 |
| 351 | Kinase (non-protein) | IPPK | 42, 43, 64 | K*K*TSEEILQHLQNIVDFGKNVMK* | 372 |
| 352 | G protein or regulator | IQGAP2 | 1024 | AWVNQLETQTGEASK*LPY DVTTE QALTYPEVK | 373 |
| 353 | G protein or regulator | IQGAP2 | 1354 | TPEEGK*QSQAVIEDAR | 374 |
| 354 | RNA processing | IREB1 | 79 | NIEVPFK*PAR | 375 |
| 355 | Ubiquitin conjugating system | ITCH | 192 | VSTNGSEDPEVAASGENK*R | 376 |
| 356 | Ubiquitin conjugating system | ITCH | 407 | FIYGNQDLFATSQNKEFDPL GPLPP GWEK*R | 377 |
| 357 | Unassigned | ITM2B | 13 | VTFNSALAQK*EAK | 378 |
| 358 | Unassigned | JOSD1 | 180 | GK*NCELLLVVPEEVEAHQS WR | 379 |
| 359 | Enzyme, misc. | KHK | 159 | IEEHNAK*QPLPQK | 380 |
| 360 | Unknown function | KIAA1033 | 1089 | AVAK*QQNVOSTSQDEK | 381 |
| 361 | Cytoskeletal protein | lamin A/C | 270 | TYSAK*LDNAR | 382 |
| 362 | Cytoskeletal protein | Lamin B1 | 124, 134 | K*ESDLSGAQIK*LR | 383 |
| 363 | Vesicle protein | LAPTM4A | 224 | IPEK*EPPPPYLPA | 384 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 364 | Calcium-binding protein | LETM1 | 715 | VIDLVNKEDVQISTTQVAEIVATLEK*EEK | 385 |
| 365 | Receptor, channel, transporter or cell surface protein | LISCH | 538 | LLEEALK*K | 386 |
| 366 | Unassigned | LOC1000444 94; Gm12508 | 63, 73; 176, 186 | MQANNAK*AVSARTEAIK*ALVK | 387 |
| 367 | Unassigned | LOCI000483 23 | 247 | SYLLEK*IKEHEESLDVTNPR | 388 |
| 368 | Unassigned | LOCI000483 23 | 343 | K*HMPYTNAMVHEVQR | 389 |
| 369 | Unassigned | LOC1000483 23 | 375 | YVDLGPTSLVHEVTCDTK*F R | 390 |
| 370 | Unknown function | LOC144100 | 742 | DQPQHLEK*ITCQQR | 391 |
| 371 | G protein or regulator | LOC435565; EG240327; ligp1 | 406; 400; 407 | TLLK*EICLRN | 392 |
| 372 | Cytoskeletal protein | MARCKS | 10 | TAAK*GEATAERPGEAAVASSPSK | 393 |
| 373 | Enzyme, misc. | MAT1A | 54 | QDPNAK*VACETVCK | 394 |
| 374 | Enzyme, misc. | MAT1A | 89 | DTIK*HIGYDDSAK | 395 |
| 375 | Enzyme, misc. | MAT1A | 98 | HIGYDDSAK*GFDFK | 396 |
| 376 | Enzyme, misc. | MAT1A | 352 | ELLEVVNK*NFDLRPGVIVR | 397 |
| 377 | Enzyme, misc. | MAT1A | 368 | DLDLK*KPIYQK | 398 |
| 378 | Enzyme, misc. | MAT1A | 374 | KPIYQK*TACYGHFGR | 399 |
| 379 | Enzyme, misc. | MAT1A | 374 | DLDLKKPIYQK*TACYGHFG R | 400 |
| 380 | Unassigned | MBD2 | 193 | SDVYYFSPSGKKFRSK* | 401 |
| 381 | Unassigned | MCT1 | 467 | EGKEDEASTDVDEK*PKETM | 402 |
| 382 | Unassigned | MCT1 | 469 | EGKEDEASTDVDEKPK*ETM | 403 |
| 383 | Enzyme, misc. | Mettl7b | 241 | WLPVGPHIM#GK*AVK | 404 |
| 384 | Enzyme, misc. | Mettl7b | 241 | WLPVGPHIMGK*AVK | 405 |
| 385 | Enzyme, misc. | MGST1 | 59 | VFANPEDCAGFGKGENAK* K | 406 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 386 | Enzyme, misc. | MGST1 | 60 | VFANPEDCAGFGKGENAKK* | 407 |
| 387 | Transcriptional regulator | MORF4L1 | 117 | ELQK*ANQEQYAEGK | 408 |
| 388 | Mitochondrial protein | MOSC1 | 313 | LCDPSEQALYGK*LPIFGQY FALEN PGTIR | 409 |
| 389 | Adaptor/ scaffold | MPP5 | 553 | DYHFVSRQAFEADIAAGKFI EHGEF EK*NLYGTSIDSVR | 410 |
| 390 | Receptor, channel, transporter or cell surface protein | MT2A | 20 | MDPNCSCASDGSCSCAGAC K*CK | 411 |
| 391 | Mitochondrial protein | MTX1 | 41 | IHK*TSNPWQSPSGTLPALR | 412 |
| 392 | Ubiquitin conjugating system | NEDD8 | 54 | QMNDEK*TAADYK | 413 |
| 393 | Enzyme, misc. | NGLY1 | 130 | KVQFSQHPAAAK*LPLEQSE DPAG LIR | 414 |
| 394 | Enzyme, misc. | NGLY1 | 130 | VQFSQHPAAAK*LPLEQSE DPAGLI R | 415 |
| 395 | Enzyme, misc. | NKEF-A | 109 | QGGLGPMNIPLISDPK*R | 416 |
| 396 | Kinase (non-protein) | NME2 | 56 | QHYIDLK*DRPFFPGLVK | 417 |
| 397 | Adaptor/ scaffold | NOSTRIN | 417 | AESK*APAGGQNNPSSSPSG STVS QASK | 418 |
| 398 | Enzyme, misc. | NQ02 | 23 | SFNGSLK*K | 419 |
| 399 | Vesicle protein | NSFL1C | 127 | GAK*EHGAVAVER | 420 |
| 400 | Receptor, channel, transporter or cell surface protein | NUP214 | 686 | STQTAPSSAPSTGQK*SPRV NPPV PKSGSSQAKALQPPVTEK | 421 |
| 401 | Enzyme, misc. | p67phox | 354 | EPKELKLSVPM#PYM#LK* | 422 |
| 402 | RNA processing | PABP 1 | 284 | KFEQMK*QDR | 423 |
| 403 | Enzyme, misc. | PAH | 49 | EEVGALAK*VLR | 424 |
| 404 | Enzyme, misc. | PAH | 95 | SKPVLGSIIK*SLR | 425 |
| 405 | Enzyme, misc. | PAH | 149 | TIQELDRFANQILSYGAELD ADHPG FK*DPVYR | 426 |
| 406 | Enzyme, misc. | PAPSS2 | 174 | AGEIK*GFTGIDSDYEKPET PECVL K | 427 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 407 | Kinase (non-protein) | PCK1 | 124 | WMSEEDFEK*AFNAR | 428 |
| 408 | Kinase (non-protein) | PCK1 | 124 | WM#SEEDFEK*AFNAR | 429 |
| 409 | Kinase (non-protein) | PCK1 | 471 | SEATAAAEHK*GK | 430 |
| 410 | Cell cycle regulation | PCM-1 | 1089 | QQNQHPEK*PR | 431 |
| 411 | Adaptor/scaffold | PDZK1 | 118 | EAALNDKK*PGPGMNGAVE PCAQP R | 432 |
| 412 | Phosphatase | PGAM1 | 105 | AETAAK*HGEAQVK | 433 |
| 413 | Vesicle protein | PICALM | 324 | EK*QAALEEEQAR | 434 |
| 414 | Kinase (non-protein) | PIP5KG | 97 | GAIQLGIGYTVGNLSSK*PER | 435 |
| 415 | Protein kinase, Ser/Thr (non-receptor) | PKG2 | 428 | RSMSSWKLSK* | 436 |
| 416 | Adhesion or extracellular matrix protein | plakophilin 2 | 134 | AAAQYSSQK*SVEER | 437 |
| 417 | Receptor, channel, transporter or cell | PMP70 | 260 | MTIMEQK*YEGEYR | 438 |
| 418 | Receptor, channel, transporter or cell | PMP70 | 576 | EGGWDSVQDWMDVLSGGE | 439 |
| 419 | Enzyme, misc. | PP ID; LOCI000452 51 | 285; 263 | LQPIALSCVLNIGACKLK* | 440 |
| 420 | Cytoskeletal protein | profilin 1 | 69 | SSFFVNGLTLGGQK*CSVIR | 441 |
| 421 | Protease | PSMA2 | 69 | SVHKVEPITK*HIGLVYSGM #GPDY R | 442 |
| 422 | Protease | PSMA6 | 102 | ARYEAANWK*YK | 443 |
| 423 | Protease | PSMB5 | 91 | ATAGAYIASQTVK*K | 444 |
| 424 | Protease | PSMC2 | 116 | YIINVK*QFAK | 445 |
| 425 | Protease | PSMC2 | 116 | IINADSEDPKYIINVK*QFAK | 446 |
| 426 | Transcriptional regulator | PSMC3 | 279 | DAFALAK*EK | 447 |
| 427 | Transcriptional regulator | PSMC3 | 279 | DAFALAK*EKAPSIIFIDELDAI GTK | 448 |
| 428 | Protease | PSMC6 | 48 | SENDLK*ALQSVGQIVGEVL | 449 |

TABLE 4-continued

Known and Novel Ubiquitination Sites Found in One Analysis of
Proteins 15 from Mouse Liver

| Row | Protein Type | Protein | Ubiquitinated Residue | Peptide Sequence | SEQ ID NO: |
|---|---|---|---|---|---|
| 429 | Protease | PSMC6 | 197 | AVASQLDCNFLK*VVSSSIVD | 450 |
| 430 | Protease | PSMC6 | 197 | AVASQLDCNFLK*VVSSSIVD KYIGE SAR | 451 |
| 431 | Protease | PSMD13 | 115 | SSDEAVILCK*TAIGALK | 452 |
| 432 | Protease | PSMD4 | 122 | IIAFVGSPVEDNEK*DLVK | 453 |
| 433 | Transcriptional regulator | PTRF | 163 | NFKVM#IYQDEVK* | 454 |
| 434 | Enzyme, | PYGL | 169 | YEYGIFNQK*IR | 455 |
| 435 | Enzyme, | PYGL | 803 | AWNTM#VLK*NIAASGK | 456 |
| 436 | Enzyme, | PYGL | 803 | AWNTMVLK*NIAASGK | 457 |
| 437 | G protein or regulator | Rab2 | 165 | TASNVEEAFINTAK*EIYEK | 458 |
| 438 | Cytoskeletal protein | radixin | 79 | KENPLQFK*FR | 459 |
| 439 | Cytoskeletal protein | radixin | 211 | IAQDLEMYGVNYFEIKNK*K | 460 |
| 440 | G protein or regulator | RALBP1 | 186 | KKPIQEPEVPQM#DAPSVK* | 461 |
| 441 | Unassigned | RGN | 233 | LDPETGK*R | 462 |
| 442 | Unassigned | Rhbdd3 | 268 | LGPGQLTWK*NSER | 463 |
| 443 | G protein or regulator | RhoA | 135 | MK*QEPVKPEEGR | 464 |
| 444 | Unknown function | RNF185 | 105 | EK*TPPRPQGQRPEPENR | 465 |
| 445 | Ubiquitin conjugating system | RNF20 | 610 | DSVKDKEK*GKHDDGR | 466 |
| 446 | Ubiquitin conjugating system | RNF5 | 93 | LK*TPPRPQGQRPAPESR | 467 |
| 447 | Unassigned | Rnft1 | 382 | EKTCPLCRTVISECINK* | 468 |
| 448 | Translation | RPL12; EG633570 | 61; 30 | ITVK*LTIQNR | 469 |
| 449 | Translation | RPL17 | 95 | KSAEFLLHMLK*NAESNAELK | 470 |
| 450 | Unassigned | RPL18 | 78 | ENK*TAVVVGTVTDDVR | 471 |
| 451 | Translation | RPL19 | 186 | KEEIIK*TLSKEEETKK | 472 |
| 452 | Translation | RPL19 | 190 | TLSK*EEETKK | 473 |
| 453 | Translation | RPL19 | 195 | TLSKEEETK*K | 474 |
| 454 | Unassigned | RPL29; LOCI000444 94; Gm1250 | 134; 134; 247; 148 | APAK*AQASAPAQAPK | 475 |
| 455 | Unassigned | RPL29; LOCI000444 94; Gm1250 | 151; 151; 264; 165 | AQASAPAQAPKGAQAPK* | 476 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 456 | Translation | RPL3 | 293 | IGQGYLIK*DGK | 477 |
| 457 | Translation | RPL3 | 299 | LIK*NNASTDYDLSDK | 478 |
| 458 | Translation | RPL4 | 294 | ILK*SPEIQR | 479 |
| 459 | Translation | RPL4 | 333 | LNPYAK*TMR | 480 |
| 460 | Translation | RPL4 | 364 | KLEAAATALATK*SEK | 481 |
| 461 | Unassigned | RPL9; Gm10117 | 21; 21 | TILSNQTVDIPENVEITLK*GR | 482 |
| 462 | Unassigned | RPLP2 | 24 | YVASYLLAALGGNSSPSAKD | 483 |
| 463 | Enzyme, misc. | RPN1 | 539 | LK*TEGSDLCDRVSEMQK | 484 |
| 464 | Translation | RPS10 | 138 | SAVPPGADK*K | 485 |
| 465 | Translation | RPS10 | 138 | RSAVPPGADK*K | 486 |
| 466 | Translation | RPS10 | 138 | SAVPPGADK*KAEAGAGSATEFQF R | 487 |
| 467 | Translation | RPS10 | 138, 139 | SAVPPGADK*K*AEAGAGSTEFQF R | 488 |
| 468 | Translation | RPS10 | 139 | RSAVPPGADKK* | 489 |
| 469 | Translation | RPS10 | 139 | SAVPPGADKK*AEAGAGSATEFQF R | 490 |
| 470 | Translation | RPS12 | 129 | DVIEEYFK*CKK | 491 |
| 471 | Translation | RPS17 | 18 | VIIEK*YYTR | 492 |
| 472 | Translation | RPS2; Gm8841; EG625055; Gm5978 | 176; 158; 67; 171 | IGK*PHTVPCK | 493 |
| 473 | Translation | RPS2; Gm8841; Gm5978 | 58; 58; 54 | AEDK*EWIPVTK | 494 |
| 474 | Unassigned | RPS20 | 34 | SLEK*VCADLIR | 495 |
| 475 | Translation | RPS21 | 51 | FNGQFK*TYGICGAIR | 496 |
| 476 | Translation | RPS25 | 114 | NTK*GGDAPAAGEDA | 497 |
| 477 | Translation | RPS3 | 214 | KPLPDHVSIVEPK*DEILPTTPISEQ K | 498 |
| 478 | Translation | RPS3 | 214 | IGPKKPLPDHVSIVEPK*DEILPTTPI SEQK | 499 |
| 479 | Translation | RPS3 | 230 | GGK*PEPPAMPQPVPTA | 500 |
| 480 | Translation | RPS3a | 45 | NIGK*TLVTR | 501 |
| 481 | Translation | RPS7 | 10 | IVK*PNGEKPDEFESGISQALLELE M#NSDLK | 502 |
| 482 | Translation | RPS7 | 15 | IVKPNGEK*PDEFESGISQALLELE M#NSDLK | 503 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 483 | Translation | RPS7 | 15 | IVKPNGEK*PDEFESGISQA LLELE MNSDLK | 504 |
| 484 | Translation | RRBP1 | 145 | K*VAKVEPAVSSIVNSIQVLA SK | 505 |
| 485 | Translation | RRBP1 | 166 | VEPAVSSIVNSIQVLASK*SA ILEATP K | 506 |
| 486 | Translation | RRBP1 | 219, 249, 289 | KGEGAQNQGK*KGEGAQNQ AK | 507 |
| 487 | Translation | RRBP1 | 229, 299, 359, 500 | KGEGAQNQAK*KGEGAQNQ AK | 508 |
| 488 | Translation | RRBP1 | 259, 339, 480 | KGEGAQNQAK*KGEGGQNQ | 509 |
| 489 | Translation | RRBP1 | 269 | KGEGGQNQAK*KGEGAQNQ | 510 |
| 490 | Translation | RRBP1 | 279, 601, 611, 621, 631, 641, 651, 681, | KGEGAQNQGK*KGEGAQNQ | 511 |
| 491 | Translation | RRBP1 | 369, 510 | KGEGAQNQAK*KGEGVQNQ | 512 |
| 492 | Translation | RRBP1 | 440, 581 | IEGAQNQGK*KPEGTSNQGK | 513 |
| 493 | Translation | RRBP1 | 440, 581 | KIEGAQNQGK*KPEGTSNQG | 514 |
| 494 | Translation | RRBP1 | 671 | KGEGPQNQAK*KGEGAQNQ | 515 |
| 495 | Translation | RRBP1 | 752 | TDTVANQGTK*QEGVSNQV | 516 |
| 496 | Translation | RRBP1 | 752 | KTDTVANQGTK*QEGVSNQ | 517 |
| 497 | Translation | RRBP1 | 823 | ASM#VQSQEAPK*QDAPAK | 518 |
| 498 | Translation | RRBP1 | 823 | ASMVQSQEAPK*QDAPAK | 519 |
| 499 | Enzyme, misc. | SAHH | 46 | EMYSASKPLK*GAR | 520 |
| 500 | Enzyme, misc. | SAHH | 166 | GISEETTTGVHNLYK*M#MS NGILK | 521 |
| 501 | Enzyme, misc. | SAHH | 166 | GISEETTTGVHNLYK*MMSN GILK | 522 |
| 502 | Enzyme, misc. | SAHH | 166 | GISEETTTGVHNLYK*MM#S NGILK | 523 |
| 503 | Enzyme, misc. | SAHH | 166 | GISEETTTGVHNLYK*M#MS NGILK VPAINVNDSVTK | 524 |
| 504 | Enzyme, misc. | SAHH | 166 | GISEETTTGVHNLYK*MMS NGILKV PAINVNDSVTK | 525 |
| 505 | Enzyme, misc. | SAHH | 166 | GISEETTTGVHNLYK*M#M #SNGIL KVPAINVNDSVTK | 526 |
| 506 | Enzyme, misc. | SAHH | 174 | GISEETTTGVHNLYKM#MSN GILK* | 527 |
| 507 | Enzyme, misc. | SAHH | 174 | GISEETTTGVHNLYKMM#S NGILK* VPAINVNDSVTK | 528 |
| 508 | Enzyme, misc. | SAHH | 186 | VPAINVNDSVTK*SK | 529 |
| 509 | Enzyme, misc. | SAHH | 188 | SK*FDNLYGCR | 530 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 510 | Adaptor/scaffold | SAKS1 | 105 | MLELVAQK*QR | 531 |
| 511 | Lipid binding protein | SEC14L2 | 11 | VGDLSPK*QEEALAK | 532 |
| 512 | Lipid binding protein | SEC14L2 | 275 | DQVK*QQYEHTVQVSR | 533 |
| 513 | Vesicle protein | SEC31L1 | 791 | AQGK*PVSGQESSQSPYER | 534 |
| 514 | Unassigned | SELENBP1; SELENBP2 | 342; 342 | QYDISNPQK*PR | 535 |
| 515 | Protein kinase, Ser/Thr (non-receptor) | SgK307 | 1148, 1153 | NTSLTDIQDLSSITYDQDGYFK*ETS YK*TPKLK | 536 |
| 516 | Chaperone | SGTA | 161 | AIGIDPGYSK*AYGR | 537 |
| 517 | Unassigned | SLC22A1 | 319 | KVPPADLK*MMCLEEDASER | 538 |
| 518 | Receptor, channel, transporter or cell surface protein | SLC26A1 | 32 | ROPPVSQGLLETLK*AR | 539 |
| 519 | Endoplasmic reticulum or golgi | SLC27A5 | 163 | LK*DAVIQNTR | 540 |
| 520 | Endoplasmic reticulum or golgi | SLC27A5 | 599 | VGMAAVK*LAPGK | 541 |
| 521 | Endoplasmic reticulum or golgi | SLC27A5 | 667 | EGFDVGIIADPLYILDNK*AQTFR | 542 |
| 522 | Unassigned | Slc38a3 | 45 | TEDTQHCGEGK*GFLQK | 543 |
| 523 | Unassigned | Slc38a3 | 50 | GFLQK*SPSKEPHFTDFEGK | 544 |
| 524 | Unassigned | Slc38a3 | 54 | SPSK*EPHFTDFEGK | 545 |
| 525 | Unassigned | Slc40a1 | 240 | AALK*VEESELK | 546 |
| 526 | Receptor, channel, transporter or cell surface protein | SLCO1A1 | 647 | LTEK*ESECTDVCR | 547 |
| 527 | Receptor, channel, transporter or cell surface protein | SLCO1B3 | 683 | KFTDEGNPEPVNNNGYSCVPSDE K*NSETPL | 548 |
| 528 | Unassigned | SLCO2A1 | 61 | SSLTTIEK* | 549 |
| 529 | Unassigned | SLCO2B1 | 676 | TTVK*SSELQQL | 550 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 530 | Apoptosis | SOD1 | 136 | QDDLGKGGNEESTK*TGNAGSR | 551 |
| 531 | Endoplasmic reticulum or golgi | SRP68 | 38 | SAGGDENK*ENERPSAGSK | 552 |
| 532 | Adaptor/scaffold | ST13 | 355 | YQSNPK*VMNLISK | 553 |
| 533 | Receptor, channel, transporter or cell surface protein | STEAP4 | 97 | EHYDSLTELVDYLK*GK | 554 |
| 534 | Enzyme, misc. | SULT1A1 | 93 | IPFLEFSCPGVPPGLETLK*ETPAPR | 555 |
| 535 | Enzyme, misc. | SULT2A1 | 90 | SPWIETDIGYSALINK*EGPR | 556 |
| 536 | Unassigned | SYNC1 | 37 | M#ASPEPLRGGDGARASREPHTE ASFPLQESESPKEAK* | 557 |
| 537 | Adaptor/scaffold | SYNE2 | 5243 | QSSLTM#DGGDVPLLEDMASGIVE LFQK*K | 558 |
| 538 | Enzyme, misc. | TALDO1 | 258 | ALAGCDFLTISPK*LLGELLK | 559 |
| 539 | Enzyme, misc. | TALDO1 | 265 | LLGELLK*DNSK | 560 |
| 540 | Enzyme, misc. | TALDO1 | 277 | LAPALSVK*AAQTSDSEKIHLDEK | 561 |
| 541 | Protein kinase, Ser/Thr (non-receptor) | Titin | 855 | ELSATSSTQK*ITK | 562 |
| 542 | Enzyme, | TKT | 260 | GITGIEDKEAWHGK*PLPK | 563 |
| 543 | Enzyme, | TKT | 281 | NMAEQIIQEIYSQVQSK*K | 564 |
| 544 | Unassigned | TMEM59 | 315 | SQTEEHEEAGPLPTK*VNLAH | 565 |
| 545 | Vesicle protein | TOLLIP | 143 | lAWTHITIPESLK*QGQVEDEWYSL SGR | 566 |
| 546 | Unassigned | TRPM8 | 283, 298 | NQLEK*YISERTSQDSNYGGK*IPIV CFAQGGGRETLK | 567 |
| 547 | Cell cycle regulation | TSGA2 | 35 | NEVGERHGHGK*AR | 568 |
| 548 | Cytoskeletal protein | TUBB2C; TUBB; TUBB2A; TUBB2B; TUBB4 | 216; 216; 216; 216; 216 | TLK*LTTPTYGDLNHLVSATMSGVT TCLR | 569 |
| 549 | Enzyme, misc. | TXNL1 | 180 | LYSMK*FQGPDNGQGPK | 570 |
| 550 | Ubiquitin conjugating system | UBE1 | 604 | KPLLESGTLGTK*GNVQVVIPFLTE SYSSSQDPPEK | 571 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 551 | Ubiquitin conjugating system | UBE1 | 627 | GNVQVVIPFLTESYSSSQDPPEK*S IPICTLK | 572 |
| 552 | Ubiquitin conjugating system | UBE1 | 635 | SIPICTLK*NFPNAIEHTLQWAR | 573 |
| 553 | Ubiquitin conjugating system | Ube1y1; UBE1 | 184; 185 | GIK*LVVADTR | 574 |
| 554 | Ubiquitin conjugating system | UBE2D3; UBE2D4 | 128; 128 | IYK*TDRDKYNR | 575 |
| 555 | Chromatin, DNA-binding, DNA repair or DNA replication protein | UBE2N | 82 | IYHPNVDK*LGR | 576 |
| 556 | Chromatin, DNA-binding, DNA repair or DNA replication protein | UBE2N | 92 | ICLDILK*DKWSPALQIR | 577 |
| 557 | Chromatin, DNA-binding, DNA repair or DNA replication protein | UBE2N | 94 | ICLDILKDK*WSPALQIR | 578 |
| 558 | Ubiquitin conjugating system | UBE2Q1 | 216, 232, 234 | K*SEDDGIGKENLAILEK*IK* | 579 |
| 559 | Ubiquitin conjugating system | ubiquitin; L0C388720 | 113; 113 | VDENGK*ISR | 580 |
| 560 | Ubiquitin conjugating system | ubiquitin; L0C388720 | 113; 113 | YYKVDENGK*ISR | 581 |
| 561 | Ubiquitin conjugating system | ubiquitin; L0C388720 | 152; 152 | CCLTYCFNK*PEDK | 582 |
| 562 | Ubiquitin conjugating system | UBQLN1 | 53 | EKEEFAVPENSSVQQFK*EEISKR | 583 |
| 563 | Enzyme, misc. | UGP2 | 183 | VK*IYTFNQSR | 584 |
| 564 | Mitochondrial protein | uricase | 118 | AHVYVEEVPWK*R | 585 |
| 565 | Mitochondrial protein | uricase | 220 | DIVLQK*FAGPYDKGEYSPSVQK | 586 |
| 566 | Protease | USP33 | 227 | SRPGSVVPANLFQGIK*TVNPTFR | 587 |

TABLE 4-continued

Known and Novel Ubiquitination Sites Found in One Analysis of Proteins 15 from Mouse Liver

| Row | Protein Type | Protein | Ubiquitinated Residue | Peptide Sequence | SEQ ID NO: |
|---|---|---|---|---|---|
| 567 | Protease | USP5 | 357 | YVDK*LEKIFQNAPTDPTQDFSTQV AK | 588 |
| 568 | Protease | USP5 | 360 | YVDKLEK*IFQNAPTDPTQDFSTQV AK | 589 |
| 569 | Protease | USP5 | 360 | KYVDKLEK*IFQNAPTQDFSTQ VAK | 590 |
| 570 | Protease | USP5 | 575 | FASFPDYLVIQIKK* | 591 |
| 571 | Cytoskeletal protein | utrophin | 50 | SGK*PPISDM#FSDLKDGR | 592 |
| 572 | Enzyme, misc. | VARS | 951 | HFCNK*LWNATK | 593 |
| 573 | Chromatin, DNA-binding, DNA repair or DNA replication protein | VCP | 109 | LGDVISIQPCPDVK*YGKR | 594 |
| 574 | Chromatin, DNA-binding, DNA repair or DNA replication protein | VCP | 336 | IVSQLLTLMDGLK*QR | 595 |
| 575 | Chromatin, DNA-binding, DNA repair or DNA replication protein | VCP | 505 | ELQELVQYPVEHPDKFLK* | 596 |
| 576 | Chromatin, DNA-binding, DNA repair or DNA replication protein | VCP | 668 | KSPVAK*DVDLEFLAK | 597 |
| 577 | Receptor, channel, transporter or cell surface protein | VDAC-1 | 287 | NVNAGGHK*LGLGLEFQA | 598 |
| 578 | RNA processing | vigilin | 494 | IEGDPQGVQQAK*R | 599 |
| 579 | Unknown function | WDR19 | 1171, 1185 | IHVKSGDHMK*GARM#LIR VANNIS K* | 600 |
| 580 | Transcriptional regulator | YB-1 | 168 | NYQQNYQNSESGEK*NEGS ESAP EGQAQQR | 601 |
| 581 | Transcriptional regulator | ZNF318 | 1246, 1250, 1268 | EVK*EDDK*APGELEEQLSEDGSAP EK*GEVKGNASLR | 602 |

% in Ubiquitinated Residue Number indicates ubiquitination sites described in scientific literature K* in Peptide Sequence indicates lysine residues modified with Gly-Gly from ubiquitin or ubiquitin-like proteins, i.e., Lys-epsilon-Gly-Gly This experiment resulted in the identification of 581 peptides that had been modified by ubiquitin or ubiquitin-like protein and allowed for the localization of the specific sites of ubiquitination within the predicate polypeptide. The experiment identified 6 of 7 known ubiquitination sites in ubiquitin itself. (See rows 39-48 of Table 4; Ikeda F, Dikic I. Atypical ubiquitin chains: new molecular signals. 'Protein Modifications: beyond the Usual Suspects' review series. EMBO Rep. 2008 June; 9(6):536-42.

Additionally, novel ubiquitination sites in enzymes responsible for linking ubiquitin to other proteins as part of the ubiquitin conjugating system were discovered (see rows 550-562 in Table 4).

Neddylation sites in ubiquitin-like molecules such as NEDD8 (see row 392 in Table 4) were also identified as trypsin digestion of neddylated proteins leaves the same K(GG) remnant as trypsin digestion of ubiquitinated proteins. Thus, the invention contemplates the use of the antibodies described herein in, for example, the methods described herein to identify neddylated proteins following digestion of such neddylated proteins with a hydrolyzing agent such as trypsin. NEDD8 is about 60% identical to ubiquitin and like ubiquitin can form polyneddylation chains (Jones J, Wu K, Yang Y, Guerrero C, Nillegoda N, Pan Z Q, Huang L. A targeted proteomic analysis of the ubiquitin-like modifier nedd8 and associated proteins. J Proteome Res. 2008 March; 7(3):1274-87). Several known ubiquitination sites in histones (e.g., H2A and H$_2$B; see rows 13-26 and 27-30, respectfully, in Table 4) were identified. Ubiquitination of these histones is thought to regulate many nuclear processes such as transcription, silencing, and DNA repair (Weake V M, Workman J L. Histone ubiquitination: triggering gene activity. Mol. Cell. 2008 Mar. 28; 29(6):653-63).

The invention also contemplates the use of the antibodies described herein in, for example, the methods described herein to identify proteins modified by the Interferon-induced 17 kDa protein, also called the I5G15 protein because it is encoded by the I5G15 gene (see Blomstrom et al., J Biol Chem 261 (19): 8811-8816, 1986). Following digestion of such I5G15-modified proteins with a hydrolyzing agent such as trypsin, the antibodies of the invention will specifically bind to and recognize the modified lysine residues in the hydrolyzed ISG15-modified proteins (see, e.g., Zhao et al., Proc. Natl. Acad. Sci. 107(5): 2253-2258, 2010).

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited above are incorporated herein by reference in their entirety to the extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

---

What is claimed is:

1. An isolated antibody that preferentially binds a ubiquitin remnant peptide over a peptide having the same amino acid sequence as the ubiquitin remnant peptide but lacking a ubiquitin remnant, wherein the antibody comprises a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

2. The isolated antibody of claim 1, wherein the antibody comprises a heavy chain sequence comprising SEQ ID NO: 1.

3. The isolated antibody of claim 1, wherein the antibody comprises a light chain sequence comprising SEQ ID NO: 2.

4. An isolated antibody that preferentially binds a ubiquitin remnant peptide over a peptide having the same amino acid sequence as the ubiquitin remnant peptide but lacking a ubiquitin remnant, wherein the antibody comprises the variable region of the heavy chain set forth in SEQ ID NO: 1.

5. An isolated antibody that preferentially binds a ubiquitin remnant peptide over a peptide having the same amino acid sequence as the ubiquitin remnant peptide but lacking a ubiquitin remnant, wherein the antibody comprises the variable region of the light chain set forth in SEQ ID NO: 2.

6. The isolated antibody of claim 2, wherein the antibody comprises a light chain sequence comprising SEQ ID NO: 2.

7. The isolated antibody of claim 4, wherein the antibody comprises the variable region of the light chain set forth in SEQ ID NO: 2.

* * * * *